(12) United States Patent
Ostrovsky et al.

(10) Patent No.: US 12,349,897 B2
(45) Date of Patent: Jul. 8, 2025

(54) ENDOSCOPIC SUTURING DEVICE WITH CIRCULAR NEEDLE

(71) Applicant: EnVision Endoscopy, Inc., Somerville, MA (US)

(72) Inventors: Isaac Ostrovsky, Wellesley, MA (US); Azadeh Khanicheh, Somerville, MA (US)

(73) Assignee: EnVision Endoscopy, Inc., Somerville, MA (US)

( * ) Notice: Subject to any disclaimer, the term of this patent is extended or adjusted under 35 U.S.C. 154(b) by 581 days.

(21) Appl. No.: 17/717,975

(22) Filed: Apr. 11, 2022

(65) Prior Publication Data

US 2022/0233182 A1 Jul. 28, 2022

Related U.S. Application Data

(63) Continuation of application No. 16/433,710, filed on Jun. 6, 2019, now Pat. No. 11,298,122.

(Continued)

(51) Int. Cl.
*A61B 17/04* (2006.01)
*A61B 1/00* (2006.01)
*A61B 17/00* (2006.01)

(52) U.S. Cl.
CPC ...... *A61B 17/0469* (2013.01); *A61B 1/00087* (2013.01); *A61B 2017/00367* (2013.01);
(Continued)

(58) Field of Classification Search
CPC ............ A61B 17/0469; A61B 17/0482; A61B 2017/047; A61B 2017/0367; A61B 2017/00407; A61B 2017/0474
See application file for complete search history.

(56) References Cited

U.S. PATENT DOCUMENTS 6,719,763 B2 4/2004 Chung et al.
6,755,843 B2 6/2004 Chung et al.
(Continued)

FOREIGN PATENT DOCUMENTS

AU 670461 B2 7/1996
CA 2139986 A1 7/1995
(Continued)

OTHER PUBLICATIONS

European Patent Office, Partial Supplementary European Search Report for European Application No. 21828283.8, dated Sep. 17, 2024, 15 pages.

(Continued)

*Primary Examiner* — Tuan V Nguyen
(74) *Attorney, Agent, or Firm* — Nutter McClennen & Fish LLP

(57) ABSTRACT

A method of suturing provides an endoscopic suture system. The endoscopic suture system has a needle coupled with a suture. The needle is configured to rotate in a first rotational direction. The system has a cable configured to move in a first direction and a second direction. The cable and the needle are configured to movably couple and uncouple. When the cable and the needle are coupled, movement of the cable in the first direction causes rotation of the needle in the first rotational direction. The method pulls the cable in the second direction, without rotating the needle, to cause coupling of the cable with the needle. The method pulls the cable in the first direction, after the needle and the cable are coupled, to rotate the needle.

19 Claims, 36 Drawing Sheets

Related U.S. Application Data

(60) Provisional application No. 62/681,783, filed on Jun. 7, 2018.

(52) U.S. Cl.
CPC ............... *A61B 2017/00818* (2013.01); *A61B 2017/047* (2013.01)

(56) References Cited

U.S. PATENT DOCUMENTS

| | | | |
|---|---|---|---|
| 6,869,395 | B2 | 3/2005 | Page et al. |
| 6,988,987 | B2 | 1/2006 | Ishikawa et al. |
| 7,144,401 | B2 | 12/2006 | Yamamoto et al. |
| 7,156,857 | B2 | 1/2007 | Pasricha et al. |
| 7,338,054 | B2 | 3/2008 | Pint |
| 7,530,985 | B2 | 5/2009 | Takemoto et al. |
| 7,618,425 | B2 | 11/2009 | Yamamoto et al. |
| 7,736,372 | B2 | 6/2010 | Reydel et al. |
| 7,927,271 | B2 | 4/2011 | Dimitriou et al. |
| 8,021,376 | B2 | 9/2011 | Takemoto et al. |
| 8,287,556 | B2 | 10/2012 | Gilkey et al. |
| 8,540,735 | B2 | 9/2013 | Mitelberg et al. |
| 8,641,728 | B2 | 2/2014 | Stokes et al. |
| 8,679,136 | B2 | 3/2014 | Mitelberg |
| 8,882,785 | B2 | 11/2014 | DiCesare et al. |
| 9,089,325 | B2 | 7/2015 | Mitelberg et al. |
| 9,198,562 | B2 | 12/2015 | Mitelberg et al. |
| 11,298,122 | B2 | 4/2022 | Ostrovsky et al. |
| 2004/0158125 | A1 | 8/2004 | Aznoian et al. |
| 2006/0282089 | A1 | 12/2006 | Stokes et al. |
| 2006/0282090 | A1 | 12/2006 | Stokes et al. |
| 2006/0282095 | A1 | 12/2006 | Stokes et al. |
| 2006/0282098 | A1 | 12/2006 | Shelton et al. |
| 2007/0167978 | A1 | 7/2007 | Yamamoto et al. |
| 2007/0239177 | A1 | 10/2007 | Stokes et al. |
| 2008/0132919 | A1 | 6/2008 | Chui et al. |
| 2010/0152751 | A1* | 6/2010 | Meade ............... A61B 34/30 606/144 |
| 2011/0270026 | A1 | 11/2011 | Chu |
| 2012/0014248 | A1 | 1/2012 | Drevo |
| 2012/0022560 | A1 | 1/2012 | Ferreira |
| 2012/0143248 | A1 | 6/2012 | Brecher et al. |
| 2012/0204865 | A1 | 8/2012 | Filipi et al. |
| 2013/0041387 | A1 | 2/2013 | Skinlo et al. |
| 2014/0171970 | A1 | 6/2014 | Martin et al. |
| 2018/0242967 | A1 | 8/2018 | Meade |
| 2019/0374218 | A1 | 12/2019 | Ostrovsky et al. |
| 2021/0322004 | A1 | 10/2021 | Khanicheh et al. |
| 2021/0393255 | A1 | 12/2021 | Khanicheh et al. |

FOREIGN PATENT DOCUMENTS

| | | |
|---|---|---|
| CN | 101049253 A | 10/2007 |
| CN | 101785687 A | 7/2010 |
| CN | 1879556 B | 12/2010 |
| CN | 103989494 A | 8/2014 |
| EP | 0588659 B1 | 11/1995 |
| JP | 2002159498 A | 6/2002 |
| JP | 2003070793 A | 3/2003 |
| JP | 2003-284722 A | 10/2003 |
| JP | 3585951 B2 | 11/2004 |
| JP | 2007-185517 A | 7/2007 |
| JP | 2009-507578 A | 2/2009 |
| JP | 5409828 B2 | 2/2014 |
| JP | 2014-531916 A | 12/2014 |
| JP | 2016-500298 A | 1/2016 |
| KR | 101531659 B1 | 6/2015 |
| WO | 2019/236911 A1 | 12/2019 |

OTHER PUBLICATIONS

International Search Report and Written Opinion for International Application No. PCT/US2021/038541, mailed Oct. 7, 2021, 14 pages.
International Preliminary Report on Patentability for International Application No. PCT/US2021/038541 mailed Jan. 5, 2023, 8 pages.
Chinese Office Action for Chinese Patent Application No. 201980052495.3, dated Jul. 22, 2024, 20 pages.
Japanese Office Action for Japanese Patent Application No. 2023-123046, dated Jun. 4, 2024, 5 pages.
European Patent Office, Extended European Search Report for Application No. 19816026.9, dated Jan. 28, 2022, 12 pages.
International Search Report and Written Opinion for International Application No. PCT/US19/53877 dated Oct. 3, 2019, 11 pages.
Chinese Office Action for Chinese Patent Application No. 201980052495.3, dated Jan. 17, 2024, 16 pages.

\* cited by examiner

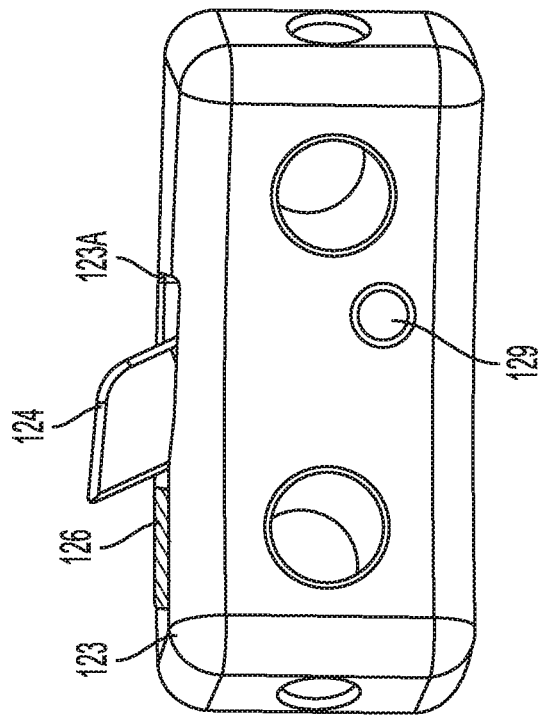
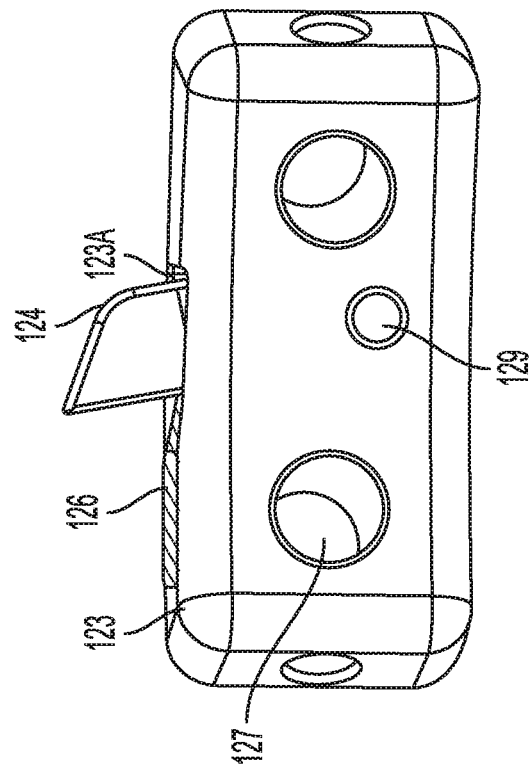

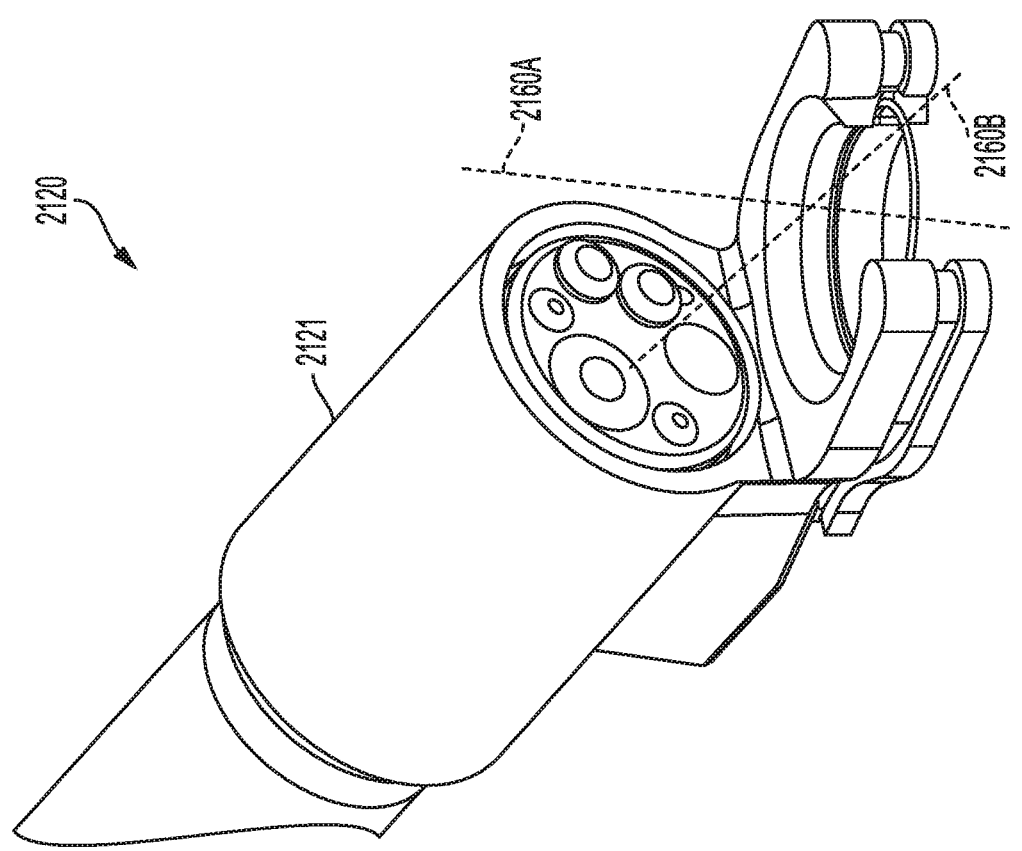

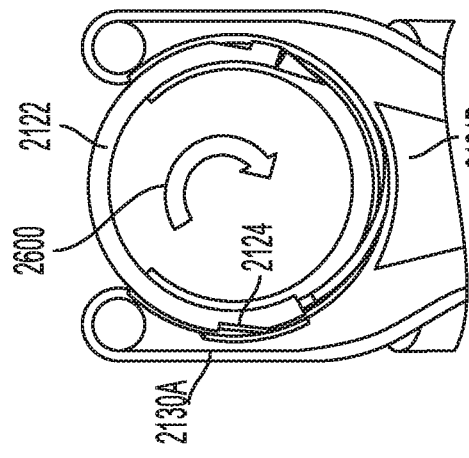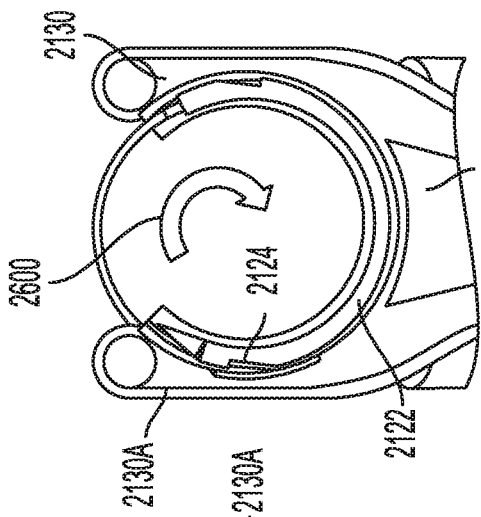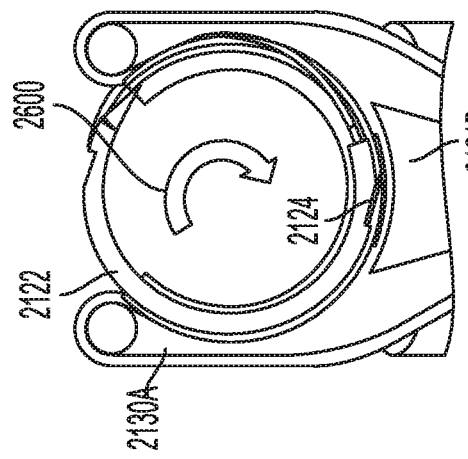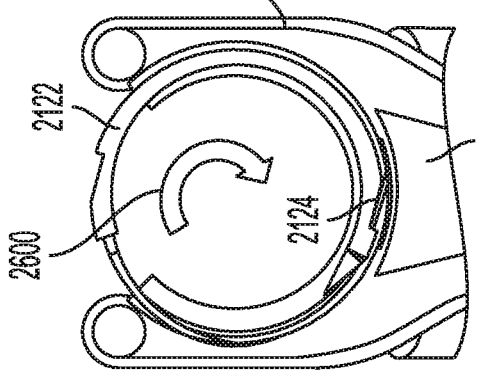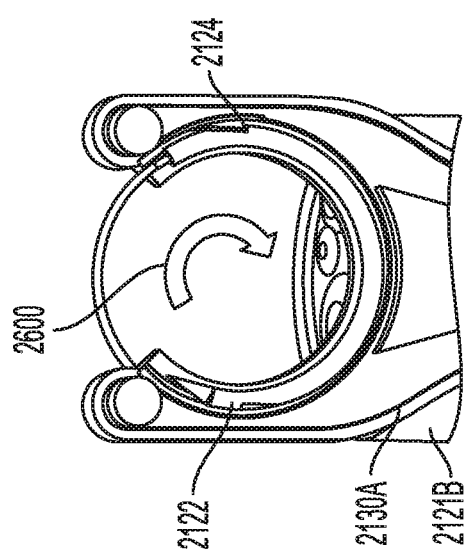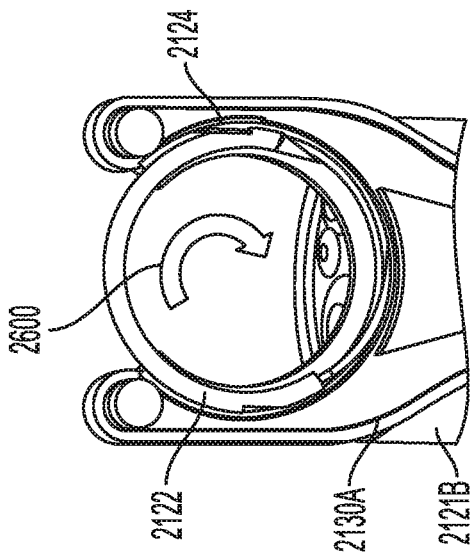

ENDOSCOPIC SUTURING DEVICE WITH CIRCULAR NEEDLE

PRIORITY

This application is a continuation of U.S. application Ser. No. 16/433,710, which claims priority to U.S. Provisional Application No. 62/681,783, filed Jun. 7, 2018, both of which are incorporated herein by reference in their entirety.

BACKGROUND

Full-thickness gastrointestinal defects such as perforation, anastomotic leak, and fistula are severe conditions caused by various types of pathologies. Such conditions are more likely to require intensive care, involve long hospital stays, and have high rates of morbidity and mortality. The currently available advanced endoscopic closing techniques have a major role in the treatment of full-thickness gastrointestinal defects. Endoscopic clips are the most common treatment for the closure of small defects. However, endoscopic clips are less useful for larger defects because of the restricted opening distance between their jaws, low closure force, and inability to accomplish deep-tissue capture.

Innovative endoscopic devices to place full thickness sutures have been an area of interest for closure of large defects. However, most of the suturing devices developed in last two decades are cumbersome and expensive, leaving more and more physicians searching for simple suturing devices. Endoscopic suturing is a minimally invasive technique that can be used for a variety of gastrointestinal indications, such as stoma and gastric reductions, fistula repair, bariatric therapy, stent and graft fixation, and GI bleeds.

SUMMARY

For correct piercing, the tissue must be supported opposite the needle side. Some devices, however, employ a driving mechanism designed such that the needle pierces by moving first sideways, pivoting about 90 degree, and finishes longitudinally from the most distal position proximally to the receiver, which now serves as a support for the pierced tissue. As such, these devices provide no support for the tissue when the needle moves sideways, so the tissue could be pushed away from the needle path before it is completely pierced. Thus, to provide such side support with such devices, a tissue grabber (e.g. grasper, corkscrew), is often required, which is a major shortcoming. Provided herein are devices, apparatus, systems, and methods that actuate an arcuate needle (as used herein, an "arcuate needle" is synonymous with a "circular needle" and is an arced needle that is not fully circular, but travels in a circular path or a substantially circular path) through a c-shaped distal assembly that is non-perpendicularly angled relative to the major axis of the endoscope and having a non-aligned angle relative to the major axis of the endoscope. As such, a tissue grabber is not necessary when using the device to suture, as the device is easily manipulated to seat the tissue between the open ends of the "C" and into the gap formed by the "C" of the c-shaped distal assembly for suturing once in such position without separate support required.

Further, for such current devices, a separate working channel must be provided to bring the grabber into the suturing area. Since one channel is used for the anchor exchange catheter, the scope must have two working channels or one extra working channel by over-tube. The requirement of a special two-channeled scope is another significant shortcoming, which makes the procedure more expensive. To preserve the small overall diameter, the working channels for the grabber must have a small outer diameter. Some current devices employ a grabber that is a long shaft with a helical screw on the tip. This helix, however, often lacks sufficient torsional stiffness to work reliably because of its small diameter and long length. Further, without a screw-in depth limit, potential perforations pose another shortcoming. Additionally, such devices employ a straight needle, which when piercing the tissue travels in a circular motion. Such a motion exposes the needle body to a sideway tissue reaction force, which might cause the needle to deflect and miss the receiver of the exchange catheter. To prevent this, the entire distal mechanisms on such devices require extra bulk to enable additional stiffness. Finally, as a distal part of such devices is positioned such that the scope camera axis lays in the needle operation plane, the tissue in the needle path blocks the camera's view during suturing. Provided herein are devices, apparatus, systems, and methods that actuate an arcuate needle through a c-shaped distal assembly that is non-perpendicularly angled relative to the major axis of the endoscope and having a non-aligned angle relative to the major axis of the endoscope, which allow for ease of vision using the camera of the device. Such distal assemblies are coupled to the distal end of the endoscope without use of the working channel, and in plain view of the camera of the endoscope during use and suturing for ease of maneuvering the needle through the tissue, and for simplicity and accuracy of suturing.

Other currently available devices employ a circular needle that is translated over the gap from exit to entrance in a uniform circular motion. While such devices enable tissue support against the piercing needle, such a needle driving mechanism is too long to be used with a flexible shaft (i.e. a flexible endoscope) without impeding its flexibility and maneuverability. Further, such devices must be rigid to employ both its rack and pinion and crankshaft positioned in-line and longitudinally, and are thus unusable for endoscopic procedures, where flexibility of the scope must not be compromised. Further, as such devices employ a cassette for suture replacement having a needle permanently attached to the suture; such a device would not be suitable for endoscopic procedures. Provided herein are devices, apparatus, systems, and methods that actuate an arcuate needle through a c-shaped distal assembly that is coupled to the distal, non-flexing, end of the scope and use a simple set of wires and shuttle coupled to the wire to manipulate the arcuate needle through the suturing process without loss of scope flexibility.

One aspect provided herein is an endoscopic suturing system comprising: a distal assembly comprising: a first housing comprising an arcuate needle guide, a shuttle guide, and an endoscope fastener, wherein the endoscope fastener couples the first housing to an endoscope; an arcuate needle comprising a notch and a suture attachment, wherein the arcuate needle has a center axis, and wherein the arcuate needle is disposed within the arcuate needle guide; and a shuttle having a pawl, wherein the shuttle is conveyed within the shuttle guide; wherein the notch and the pawl engage when the shuttle translates in a first rotational direction about the center axis, and wherein the notch and the pawl disengage when the shuttle translates opposite the first rotational direction; a proximal assembly comprising: a second housing; an actuator connected to the second housing; and a cable connecting the actuator to the shuttle and configured to translate the shuttle in the first direction and in the second direction in response to an actuation of the actuator.

In some embodiments, the pawl comprises a spring, a flexure, a dual spring gate, a cushion, a piston, a rod, a pin, a tooth, or any combination thereof. In some embodiments, the pawl is engagement biased. In some embodiments, the notch is ramped in a direction opposite the first direction. In some embodiments, the endoscope fastener comprises a tie, a string, a band, a hook and loop fastener, a tape, a strap, a magnet, a cinch, a press fit, a set screw, an adhesive, or any combination thereof.

In some embodiments, the endoscope has a proximal outer diameter of about 5 mm to about 16 mm. In some embodiments, the endoscope has a proximal outer diameter of about 5 mm to about 6 mm, about 5 mm to about 7 mm, about 5 mm to about 8 mm, about 5 mm to about 9 mm, about 5 mm to about 10 mm, about 5 mm to about 11 mm, about 5 mm to about 12 mm, about 5 mm to about 13 mm, about 5 mm to about 14 mm, about 5 mm to about 15 mm, about 5 mm to about 16 mm, about 6 mm to about 7 mm, about 6 mm to about 8 mm, about 6 mm to about 9 mm, about 6 mm to about 10 mm, about 6 mm to about 11 mm, about 6 mm to about 12 mm, about 6 mm to about 13 mm, about 6 mm to about 14 mm, about 6 mm to about 15 mm, about 6 mm to about 16 mm, about 7 mm to about 8 mm, about 7 mm to about 9 mm, about 7 mm to about 10 mm, about 7 mm to about 11 mm, about 7 mm to about 12 mm, about 7 mm to about 13 mm, about 7 mm to about 14 mm, about 7 mm to about 15 mm, about 7 mm to about 16 mm, about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 8 mm to about 16 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 11 mm to about 12 mm, about 11 mm to about 13 mm, about 11 mm to about 14 mm, about 11 mm to about 15 mm, about 11 mm to about 16 mm, about 12 mm to about 13 mm, about 12 mm to about 14 mm, about 12 mm to about 15 mm, about 12 mm to about 16 mm, about 13 mm to about 14 mm, about 13 mm to about 15 mm, about 13 mm to about 16 mm, about 14 mm to about 15 mm, about 14 mm to about 16 mm, or about 15 mm to about 16 mm. In some embodiments, the endoscope has a proximal outer diameter of about 5 mm, about 6 mm, about 7 mm, about 8 mm, about 9 mm, about 10 mm, about 11 mm, about 12 mm, about 13 mm, about 14 mm, about 15 mm, or about 16 mm. In some embodiments, the endoscope has a proximal outer diameter of at least about 5 mm, about 6 mm, about 7 mm, about 8 mm, about 9 mm, about 10 mm, about 11 mm, about 12 mm, about 13 mm, about 14 mm, or about 15 mm. In some embodiments, the endoscope has a proximal outer diameter of at most about 6 mm, about 7 mm, about 8 mm, about 9 mm, about 10 mm, about 11 mm, about 12 mm, about 13 mm, about 14 mm, about 15 mm, or about 16 mm.

In some embodiments, the endoscope fastener has an inner diameter of about 5 mm to about 16 mm. In some embodiments, the endoscope fastener has an inner diameter of about 5 mm to about 6 mm, about 5 mm to about 7 mm, about 5 mm to about 8 mm, about 5 mm to about 9 mm, about 5 mm to about 10 mm, about 5 mm to about 11 mm, about 5 mm to about 12 mm, about 5 mm to about 13 mm, about 5 mm to about 14 mm, about 5 mm to about 15 mm, about 5 mm to about 16 mm, about 6 mm to about 7 mm, about 6 mm to about 8 mm, about 6 mm to about 9 mm, about 6 mm to about 10 mm, about 6 mm to about 11 mm, about 6 mm to about 12 mm, about 6 mm to about 13 mm, about 6 mm to about 14 mm, about 6 mm to about 15 mm, about 6 mm to about 16 mm, about 7 mm to about 8 mm, about 7 mm to about 9 mm, about 7 mm to about 10 mm, about 7 mm to about 11 mm, about 7 mm to about 12 mm, about 7 mm to about 13 mm, about 7 mm to about 14 mm, about 7 mm to about 15 mm, about 7 mm to about 16 mm, about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 8 mm to about 16 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 11 mm to about 12 mm, about 11 mm to about 13 mm, about 11 mm to about 14 mm, about 11 mm to about 15 mm, about 11 mm to about 16 mm, about 12 mm to about 13 mm, about 12 mm to about 14 mm, about 12 mm to about 15 mm, about 12 mm to about 16 mm, about 13 mm to about 14 mm, about 13 mm to about 15 mm, about 13 mm to about 16 mm, about 14 mm to about 15 mm, about 14 mm to about 16 mm, or about 15 mm to about 16 mm. In some embodiments, the endoscope fastener has an inner diameter of about 5 mm, about 6 mm, about 7 mm, about 8 mm, about 9 mm, about 10 mm, about 11 mm, about 12 mm, about 13 mm, about 14 mm, about 15 mm, or about 16 mm. In some embodiments, the endoscope fastener has an inner diameter of at least about 5 mm, about 6 mm, about 7 mm, about 8 mm, about 9 mm, about 10 mm, about 11 mm, about 12 mm, about 13 mm, about 14 mm, or about 15 mm. In some embodiments, the endoscope fastener has an inner diameter of at most about 6 mm, about 7 mm, about 8 mm, about 9 mm, about 10 mm, about 11 mm, about 12 mm, about 13 mm, about 14 mm, about 15 mm, or about 16 mm.

In some embodiments, the system further comprises a cable sheath surrounding at least a portion of the cable. In some embodiments, the system further comprises a cable fastener that removably couples at least a portion of the cable sheath to the endoscope. In some embodiments, the cable fastener comprises a tie, a string, a band, a hook and loop fastener, a tape, a strap, a magnet, a cinch, a press fit, a set screw, an adhesive, or any combination thereof.

In some embodiments, an angle between a center axis of the arcuate needle guide and a proximal axis of the endoscope is about 5 degrees to about 120 degrees. In some embodiments, an angle between a center axis of the arcuate needle guide and a proximal axis of the endoscope is about 5 degrees to about 10 degrees, about 5 degrees to about 20 degrees, about 5 degrees to about 30 degrees, about 5 degrees to about 40 degrees, about 5 degrees to about 50 degrees, about 5 degrees to about 60 degrees, about 5 degrees to about 70 degrees, about 5 degrees to about 80 degrees, about 5 degrees to about 90 degrees, about 5 degrees to about 100 degrees, about 5 degrees to about 120 degrees, about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 70 degrees, about 10 degrees to about 80 degrees, about 10 degrees to about 90 degrees, about 10 degrees to about 100 degrees, about 10 degrees to about 120 degrees, about 20 degrees to about 30 degrees, about 20 degrees to about 40 degrees, about 20 degrees to about 50 degrees, about 20 degrees to about 60 degrees, about 20 degrees to about 70 degrees, about 20 degrees to about 80 degrees, about 20 degrees to about 90 degrees, about 20 degrees to about 100 degrees, about 20 degrees to about 120 degrees, about 30 degrees to about 40 degrees, about 30 degrees to about 50 degrees, about 30 degrees to about 60 degrees, about 30 degrees to about 70 degrees, about 30 degrees to about 80 degrees, about 30 degrees to about 90 degrees, about 30 degrees to about 100 degrees, about 30 degrees to about 120 degrees, about 40 degrees to about 50 degrees, about 40 degrees to about 60 degrees, about 40 degrees to about 70 degrees, about 40 degrees to about 80 degrees, about 40 degrees to about 90 degrees, about 40 degrees to about 100 degrees, about 40 degrees to about 120 degrees, about 50 degrees to about 60 degrees, about 50 degrees to about 70 degrees, about 50 degrees to about 80 degrees, about 50 degrees to about 90 degrees, about 50 degrees to about 100 degrees, about 50 degrees to about 120 degrees, about 60 degrees to about 70 degrees, about 60 degrees to about 80 degrees, about 60 degrees to about 90 degrees, about 60 degrees to about 100 degrees, about 60 degrees to about 120 degrees, about 70 degrees to about 80 degrees, about 70 degrees to about 90 degrees, about 70 degrees to about 100 degrees, about 70 degrees to about 120 degrees, about 80 degrees to about 90 degrees, about 80 degrees to about 100 degrees, about 80 degrees to about 120 degrees, about 90 degrees to about 100 degrees, about 90 degrees to about 120 degrees, or about 100 degrees to about 120 degrees. In some embodiments, an angle between a center axis of the arcuate needle guide and a proximal axis of the endoscope is about 5 degrees, about 10 degrees, about 20 degrees, about 30 degrees, about 40 degrees, about 50 degrees, about 60 degrees, about 70 degrees, about 80 degrees, about 90 degrees, about 100 degrees, or about 120 degrees. In some embodiments, an angle between a center axis of the arcuate needle guide and a proximal axis of the endoscope is at least about 5 degrees, about 10 degrees, about 20 degrees, about 30 degrees, about 40 degrees, about 50 degrees, about 60 degrees, about 70 degrees, about 80 degrees, about 90 degrees, or about 100 degrees. In some embodiments, an angle between a center axis of the arcuate needle guide and a proximal axis of the endoscope is at most about 10 degrees, about 20 degrees, about 30 degrees, about 40 degrees, about 50 degrees, about 60 degrees, about 70 degrees, about 80 degrees, about 90 degrees, about 100 degrees, or about 120 degrees.

In some embodiments, an angle between a center axis adjustable within of the arcuate needle guide and a proximal axis adjustable within of the endoscope is adjustable within about 5 degrees to about 120 degrees. In some embodiments, an angle between a center axis adjustable within of the arcuate needle guide and a proximal axis adjustable within of the endoscope is adjustable within about 5 degrees to about 10 degrees, about 5 degrees to about 20 degrees, about 5 degrees to about 30 degrees, about 5 degrees to about 40 degrees, about 5 degrees to about 50 degrees, about 5 degrees to about 60 degrees, about 5 degrees to about 70 degrees, about 5 degrees to about 80 degrees, about 5 degrees to about 90 degrees, about 5 degrees to about 100 degrees, about 5 degrees to about 120 degrees, about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 70 degrees, about 10 degrees to about 80 degrees, about 10 degrees to about 90 degrees, about 10 degrees to about 100 degrees, about 10 degrees to about 120 degrees, about 20 degrees to about 30 degrees, about 20 degrees to about 40 degrees, about 20 degrees to about 50 degrees, about 20 degrees to about 60 degrees, about 20 degrees to about 70 degrees, about 20 degrees to about 80 degrees, about 20 degrees to about 90 degrees, about 20 degrees to about 100 degrees, about 20 degrees to about 120 degrees, about 30 degrees to about 40 degrees, about 30 degrees to about 50 degrees, about 30 degrees to about 60 degrees, about 30 degrees to about 70 degrees, about 30 degrees to about 80 degrees, about 30 degrees to about 90 degrees, about 30 degrees to about 100 degrees, about 30 degrees to about 120 degrees, about 40 degrees to about 50 degrees, about 40 degrees to about 60 degrees, about 40 degrees to about 70 degrees, about 40 degrees to about 80 degrees, about 40 degrees to about 90 degrees, about 40 degrees to about 100 degrees, about 40 degrees to about 120 degrees, about 50 degrees to about 60 degrees, about 50 degrees to about 70 degrees, about 50 degrees to about 80 degrees, about 50 degrees to about 90 degrees, about 50 degrees to about 100 degrees, about 50 degrees to about 120 degrees, about 60 degrees to about 70 degrees, about 60 degrees to about 80 degrees, about 60 degrees to about 90 degrees, about 60 degrees to about 100 degrees, about 60 degrees to about 120 degrees, about 70 degrees to about 80 degrees, about 70 degrees to about 90 degrees, about 70 degrees to about 100 degrees, about 70 degrees to about 120 degrees, about 80 degrees to about 90 degrees, about 80 degrees to about 100 degrees, about 80 degrees to about 120 degrees, about 90 degrees to about 100 degrees, about 90 degrees to about 120 degrees, or about 100 degrees to about 120 degrees. In some embodiments, an angle between a center axis adjustable within of the arcuate needle guide and a proximal axis adjustable within of the endoscope is adjustable within about 5 degrees, about 10 degrees, about 20 degrees, about 30 degrees, about 40 degrees, about 50 degrees, about 60 degrees, about 70 degrees, about 80 degrees, about 90 degrees, about 100 degrees, or about 120 degrees. In some embodiments, an angle between a center axis adjustable within of the arcuate needle guide and a proximal axis adjustable within of the endoscope is adjustable within at least about 5 degrees, about 10 degrees, about 20 degrees, about 30 degrees, about 40 degrees, about 50 degrees, about 60 degrees, about 70 degrees, about 80 degrees, about 90 degrees, or about 100 degrees. In some embodiments, an angle between a center axis adjustable within of the arcuate needle guide and a proximal axis adjustable within of the endoscope is adjustable within at most about 10 degrees, about 20 degrees, about 30 degrees, about 40 degrees, about 50 degrees, about 60 degrees, about 70 degrees, about 80 degrees, about 90 degrees, about 100 degrees, or about 120 degrees.

In some embodiments, the arcuate needle comprises two or more notches. In some embodiments, at least one of the first housing, the second housing, the arcuate needle, the shuttle, or the actuator are composed of plastic, metal, fiberglass, carbon fiber, wood, or any combination thereof. In some embodiments, the first housing further comprises a cable pulley that guides the cable. In some embodiments, the arcuate needle further comprises a suture attachment fastener. In some embodiments, first housing further comprises a pulley, and wherein the cable is strung around the pulley. In some embodiments, the second housing couples to the endoscope.

Another aspect provided herein is an endoscopic suturing system comprising: a distal assembly comprising: a first housing comprising an arcuate needle guide and an endoscope fastener, wherein the endoscope fastener couples the first housing to an endoscope; an arcuate needle comprising a notch and a suture attachment, wherein the arcuate needle has a center axis, and wherein the arcuate needle is disposed within the arcuate needle guide; and a proximal assembly comprising: a second housing that removably attaches to an endoscope; an actuator connected to the second housing; and a cable having a pawl; wherein the notch and the pawl engage when the cable translates in a first rotational direction about the center axis, and wherein the notch and the pawl disengage when the cable translates opposite the first rotational direction.

In some embodiments, the pawl comprises a spring, a flexure, a dual spring gate, a cushion, a piston, a rod, a pin, a tooth, or any combination thereof. In some embodiments, the pawl is engagement biased. In some embodiments, the notch is ramped in a direction opposite the first direction. In some embodiments, the endoscope fastener comprises a press-fit fastener, a clamp, an adhesive, a tape, a strap, a set screw, a hook and loop fastener, a magnet, or any combination thereof.

In some embodiments, the endoscope has a proximal outer diameter of about 5 mm to about 16 mm. In some embodiments, the endoscope has a proximal outer diameter of about 5 mm to about 6 mm, about 5 mm to about 7 mm, about 5 mm to about 8 mm, about 5 mm to about 9 mm, about 5 mm to about 10 mm, about 5 mm to about 11 mm, about 5 mm to about 12 mm, about 5 mm to about 13 mm, about 5 mm to about 14 mm, about 5 mm to about 15 mm, about 5 mm to about 16 mm, about 6 mm to about 7 mm, about 6 mm to about 8 mm, about 6 mm to about 9 mm, about 6 mm to about 10 mm, about 6 mm to about 11 mm, about 6 mm to about 12 mm, about 6 mm to about 13 mm, about 6 mm to about 14 mm, about 6 mm to about 15 mm, about 6 mm to about 16 mm, about 7 mm to about 8 mm, about 7 mm to about 9 mm, about 7 mm to about 10 mm, about 7 mm to about 11 mm, about 7 mm to about 12 mm, about 7 mm to about 13 mm, about 7 mm to about 14 mm, about 7 mm to about 15 mm, about 7 mm to about 16 mm, about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 8 mm to about 16 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 11 mm to about 12 mm, about 11 mm to about 13 mm, about 11 mm to about 14 mm, about 11 mm to about 15 mm, about 11 mm to about 16 mm, about 12 mm to about 13 mm, about 12 mm to about 14 mm, about 12 mm to about 15 mm, about 12 mm to about 16 mm, about 13 mm to about 14 mm, about 13 mm to about 15 mm, about 13 mm to about 16 mm, about 14 mm to about 15 mm, about 14 mm to about 16 mm, or about 15 mm to about 16 mm. In some embodiments, the endoscope has a proximal outer diameter of about 5 mm, about 6 mm, about 7 mm, about 8 mm, about 9 mm, about 10 mm, about 11 mm, about 12 mm, about 13 mm, about 14 mm, about 15 mm, or about 16 mm. In some embodiments, the endoscope has a proximal outer diameter of at least about 5 mm, about 6 mm, about 7 mm, about 8 mm, about 9 mm, about 10 mm, about 11 mm, about 12 mm, about 13 mm, about 14 mm, or about 15 mm. In some embodiments, the endoscope has a proximal outer diameter of at most about 6 mm, about 7 mm, about 8 mm, about 9 mm, about 10 mm, about 11 mm, about 12 mm, about 13 mm, about 14 mm, about 15 mm, or about 16 mm.

In some embodiments, the endoscope fastener has an inner diameter of about 5 mm to about 16 mm. In some embodiments, the endoscope fastener has an inner diameter of about 5 mm to about 6 mm, about 5 mm to about 7 mm, about 5 mm to about 8 mm, about 5 mm to about 9 mm, about 5 mm to about 10 mm, about 5 mm to about 11 mm, about 5 mm to about 12 mm, about 5 mm to about 13 mm, about 5 mm to about 14 mm, about 5 mm to about 15 mm, about 5 mm to about 16 mm, about 6 mm to about 7 mm, about 6 mm to about 8 mm, about 6 mm to about 9 mm, about 6 mm to about 10 mm, about 6 mm to about 11 mm, about 6 mm to about 12 mm, about 6 mm to about 13 mm, about 6 mm to about 14 mm, about 6 mm to about 15 mm, about 6 mm to about 16 mm, about 7 mm to about 8 mm, about 7 mm to about 9 mm, about 7 mm to about 10 mm, about 7 mm to about 11 mm, about 7 mm to about 12 mm, about 7 mm to about 13 mm, about 7 mm to about 14 mm, about 7 mm to about 15 mm, about 7 mm to about 16 mm, about 8 mm to about 9 mm, about 8 mm to about 10 mm, about 8 mm to about 11 mm, about 8 mm to about 12 mm, about 8 mm to about 13 mm, about 8 mm to about 14 mm, about 8 mm to about 15 mm, about 8 mm to about 16 mm, about 9 mm to about 10 mm, about 9 mm to about 11 mm, about 9 mm to about 12 mm, about 9 mm to about 13 mm, about 9 mm to about 14 mm, about 9 mm to about 15 mm, about 9 mm to about 16 mm, about 10 mm to about 11 mm, about 10 mm to about 12 mm, about 10 mm to about 13 mm, about 10 mm to about 14 mm, about 10 mm to about 15 mm, about 10 mm to about 16 mm, about 11 mm to about 12 mm, about 11 mm to about 13 mm, about 11 mm to about 14 mm, about 11 mm to about 15 mm, about 11 mm to about 16 mm, about 12 mm to about 13 mm, about 12 mm to about 14 mm, about 12 mm to about 15 mm, about 12 mm to about 16 mm, about 13 mm to about 14 mm, about 13 mm to about 15 mm, about 13 mm to about 16 mm, about 14 mm to about 15 mm, about 14 mm to about 16 mm, or about 15 mm to about 16 mm. In some embodiments, the endoscope fastener has an inner diameter of about 5 mm, about 6 mm, about 7 mm, about 8 mm, about 9 mm, about 10 mm, about 11 mm, about 12 mm, about 13 mm, about 14 mm, about 15 mm, or about 16 mm. In some embodiments, the endoscope fastener has an inner diameter of at least about 5 mm, about 6 mm, about 7 mm, about 8 mm, about 9 mm, about 10 mm, about 11 mm, about 12 mm, about 13 mm, about 14 mm, or about 15 mm. In some embodiments, the endoscope fastener has an inner diameter of at most about 6 mm, about 7 mm, about 8 mm, about 9 mm, about 10 mm, about 11 mm, about 12 mm, about 13 mm, about 14 mm, about 15 mm, or about 16 mm.

In some embodiments, the system further comprises a cable sheath surrounding at least a portion of the cable. In some embodiments, the system further comprises a cable fastener that removably couples at least a portion of the cable to the endoscope. In some embodiments, the cable fastener comprises a press-fit fastener, a clamp, an adhesive, a tape, a strap, a set screw, a hook and loop fastener, a magnet, or any combination thereof.

In some embodiments, an angle between a center axis of the arcuate needle guide and a proximal axis of the endoscope is about 5 degrees to about 120 degrees. In some embodiments, an angle between a center axis of the arcuate needle guide and a proximal axis of the endoscope is about 5 degrees to about 10 degrees, about 5 degrees to about 20 degrees, about 5 degrees to about 30 degrees, about 5 degrees to about 40 degrees, about 5 degrees to about 50 degrees, about 5 degrees to about 60 degrees, about 5 degrees to about 70 degrees, about 5 degrees to about 80 degrees, about 5 degrees to about 90 degrees, about 5 degrees to about 100 degrees, about 5 degrees to about 120 degrees, about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 70 degrees, about 10 degrees to about 80 degrees, about 10 degrees to about 90 degrees, about 10 degrees to about 100 degrees, about 10 degrees to about 120 degrees, about 20 degrees to about 30 degrees, about 20 degrees to about 40 degrees, about 20 degrees to about 50 degrees, about 20 degrees to about 60 degrees, about 20 degrees to about 70 degrees, about 20 degrees to about 80 degrees, about 20 degrees to about 90 degrees, about 20 degrees to about 100 degrees, about 20 degrees to about 120 degrees, about 30 degrees to about 40 degrees, about 30 degrees to about 50 degrees, about 30 degrees to about 60 degrees, about 30 degrees to about 70 degrees, about 30 degrees to about 80 degrees, about 30 degrees to about 90 degrees, about 30 degrees to about 100 degrees, about 30 degrees to about 120 degrees, about 40 degrees to about 50 degrees, about 40 degrees to about 60 degrees, about 40 degrees to about 70 degrees, about 40 degrees to about 80 degrees, about 40 degrees to about 90 degrees, about 40 degrees to about 100 degrees, about 40 degrees to about 120 degrees, about 50 degrees to about 60 degrees, about 50 degrees to about 70 degrees, about 50 degrees to about 80 degrees, about 50 degrees to about 90 degrees, about 50 degrees to about 100 degrees, about 50 degrees to about 120 degrees, about 60 degrees to about 70 degrees, about 60 degrees to about 80 degrees, about 60 degrees to about 90 degrees, about 60 degrees to about 100 degrees, about 60 degrees to about 120 degrees, about 70 degrees to about 80 degrees, about 70 degrees to about 90 degrees, about 70 degrees to about 100 degrees, about 70 degrees to about 120 degrees, about 80 degrees to about 90 degrees, about 80 degrees to about 100 degrees, about 80 degrees to about 120 degrees, about 90 degrees to about 100 degrees, about 90 degrees to about 120 degrees, or about 100 degrees to about 120 degrees. In some embodiments, an angle between a center axis of the arcuate needle guide and a proximal axis of the endoscope is about 5 degrees, about 10 degrees, about 20 degrees, about 30 degrees, about 40 degrees, about 50 degrees, about 60 degrees, about 70 degrees, about 80 degrees, about 90 degrees, about 100 degrees, or about 120 degrees. In some embodiments, an angle between a center axis of the arcuate needle guide and a proximal axis of the endoscope is at least about 5 degrees, about 10 degrees, about 20 degrees, about 30 degrees, about 40 degrees, about 50 degrees, about 60 degrees, about 70 degrees, about 80 degrees, about 90 degrees, or about 100 degrees. In some embodiments, an angle between a center axis of the arcuate needle guide and a proximal axis of the endoscope is at most about 10 degrees, about 20 degrees, about 30 degrees, about 40 degrees, about 50 degrees, about 60 degrees, about 70 degrees, about 80 degrees, about 90 degrees, about 100 degrees, or about 120 degrees.

In some embodiments, an angle between a center axis adjustable within of the arcuate needle guide and a proximal axis adjustable within of the endoscope is adjustable within about 5 degrees to about 120 degrees. In some embodiments, an angle between a center axis adjustable within of the arcuate needle guide and a proximal axis adjustable within of the endoscope is adjustable within about 5 degrees to about 10 degrees, about 5 degrees to about 20 degrees, about 5 degrees to about 30 degrees, about 5 degrees to about 40 degrees, about 5 degrees to about 50 degrees, about 5 degrees to about 60 degrees, about 5 degrees to about 70 degrees, about 5 degrees to about 80 degrees, about 5 degrees to about 90 degrees, about 5 degrees to about 100 degrees, about 5 degrees to about 120 degrees, about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 70 degrees, about 10 degrees to about 80 degrees, about 10 degrees to about 90 degrees, about 10 degrees to about 100 degrees, about 10 degrees to about 120 degrees, about 20 degrees to about 30 degrees, about 20 degrees to about 40 degrees, about 20 degrees to about 50 degrees, about 20 degrees to about 60 degrees, about 20 degrees to about 70 degrees, about 20 degrees to about 80 degrees, about 20 degrees to about 90 degrees, about 20 degrees to about 100 degrees, about 20 degrees to about 120 degrees, about 30 degrees to about 40 degrees, about 30 degrees to about 50 degrees, about 30 degrees to about 60 degrees, about 30 degrees to about 70 degrees, about 30 degrees to about 80 degrees, about 30 degrees to about 90 degrees, about 30 degrees to about 100 degrees, about 30 degrees to about 120 degrees, about 40 degrees to about 50 degrees, about 40 degrees to about 60 degrees, about 40 degrees to about 70 degrees, about 40 degrees to about 80 degrees, about 40 degrees to about 90 degrees, about 40 degrees to about 100 degrees, about 40 degrees to about 120 degrees, about 50 degrees to about 60 degrees, about 50 degrees to about 70 degrees, about 50 degrees to about 80 degrees, about 50 degrees to about 90 degrees, about 50 degrees to about 100 degrees, about 50 degrees to about 120 degrees, about 60 degrees to about 70 degrees, about 60 degrees to about 80 degrees, about 60 degrees to about 90 degrees, about 60 degrees to about 100 degrees, about 60 degrees to about 120 degrees, about 70 degrees to about 80 degrees, about 70 degrees to about 90 degrees, about 70 degrees to about 100 degrees, about 70 degrees to about 120 degrees, about 80 degrees to about 90 degrees, about 80 degrees to about 100 degrees, about 80 degrees to about 120 degrees, about 90 degrees to about 100 degrees, about 90 degrees to about 120 degrees, or about 100 degrees to about 120 degrees. In some embodiments, an angle between a center axis adjustable within of the arcuate needle guide and a proximal axis adjustable within of the endoscope is adjustable within about 5 degrees, about 10 degrees, about 20 degrees, about 30 degrees, about 40 degrees, about 50 degrees, about 60 degrees, about 70 degrees, about 80 degrees, about 90 degrees, about 100 degrees, or about 120 degrees. In some embodiments, an angle between a center axis adjustable within of the arcuate needle guide and a proximal axis adjustable within of the endoscope is adjustable within at least about 5 degrees, about 10 degrees, about 20 degrees, about 30 degrees, about 40 degrees, about 50 degrees, about 60 degrees, about 70 degrees, about 80 degrees, about 90 degrees, or about 100 degrees. In some embodiments, an angle between a center axis adjustable within of the arcuate needle guide and a proximal axis adjustable within of the endoscope is adjustable within at most about 10 degrees, about 20 degrees, about 30 degrees, about 40 degrees, about 50 degrees, about 60 degrees, about 70 degrees, about 80 degrees, about 90 degrees, about 100 degrees, or about 120 degrees.

In some embodiments, the arcuate needle comprises two or more notches. In some embodiments, at least one of the first housing, the second housing, the arcuate needle, or the actuator are composed of plastic, metal, fiberglass, carbon fiber, wood, or any combination thereof. In some embodiments, the first housing further comprises a cable pulley that guides the cable. In some embodiments, the arcuate needle further comprises a suture attachment fastener. In some embodiments, first housing further comprises a pulley, and wherein the cable is strung around the pulley. In some embodiments, the second housing couples to the endoscope.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 19A is an exemplary illustration of a shuttle, wherein the pawl is engaged, per an embodiment herein;

FIG. 19B is an exemplary illustration of a shuttle, wherein the pawl is disengaged, per an embodiment herein;

FIG. 20 is a first illustration of an exemplary second proximal assembly coupled to an endoscope, per an embodiment herein;

FIG. 27A is a bottom cross-sectioned illustration of the exemplary second proximal assembly in a first position, per an embodiment herein;

FIG. 27B is a bottom cross-sectioned illustration of the exemplary second proximal assembly in a second position, per an embodiment herein;

FIG. 27C is a bottom cross-sectioned illustration of the exemplary second proximal assembly in a third position, per an embodiment herein;

FIG. 27D is a bottom cross-sectioned illustration of the exemplary second proximal assembly in a fourth position, per an embodiment herein;

FIG. 27E is a bottom cross-sectioned illustration of the exemplary second proximal assembly in a fifth position, per an embodiment herein;

FIG. 27F is a bottom cross-sectioned illustration of the exemplary second proximal assembly in a sixth position, per an embodiment herein;

DETAILED DESCRIPTION

Provided herein are tissue suturing systems, devices, apparatuses, and methods for endoscopic suturing of tissue in the body. In some embodiments, the systems, devices, apparatuses, and methods herein are used in conjunction with a flexible endoscope to suture tissue. The suturing systems, devices, apparatuses and methods described herein are configured to perform full thickness endoscopic suturing for a variety of gastrointestinal indications including, for example, tissue closure, bariatric therapy, stent fixation, and graft fixation. Provided herein are devices, apparatus, and systems that actuate an arcuate needle (as used herein, an "arcuate needle" is synonymous with a "circular needle" and is an arced needle that is not fully circular, but travels in a circular path or a substantially circular path) through a c-shaped portion of a distal assembly, wherein such c-shaped portion of the distal assembly is non-perpendicularly angled relative to the major axis of the endoscope and has a non-aligned angle relative to the major axis of the endoscope (see needle axis 501, elsewhere herein). As such, a tissue grabber is not necessary when suturing using the arcuate needle of the distal assembly, as the distal assembly is easily manipulated to seat the tissue between open ends of the c-shape portion of the distal assembly and into the gap formed by the "C" of the c-shaped portion of the distal assembly for suturing once in such position without separate support required. The alignment and angles of the devices, apparatus, and systems and methods relative to the scope allow for ease of vision using the camera of the device. Such distal assemblies are coupled to the distal end of the endoscope without use of the working channel, and in plain view of the camera of the endoscope during use and suturing for ease of maneuvering the needle through the tissue, and for simplicity and accuracy of suturing. Further, the devices, apparatus, and systems and methods described herein actuate the arcuate needle through a c-shaped distal assembly that is coupled to the distal, non-flexing, end of the scope and use a simple set of wires and shuttle coupled to the wire to manipulate the arcuate needle through the suturing process without loss of scope flexibility.

Endoscopic Suturing System

Figure 1:
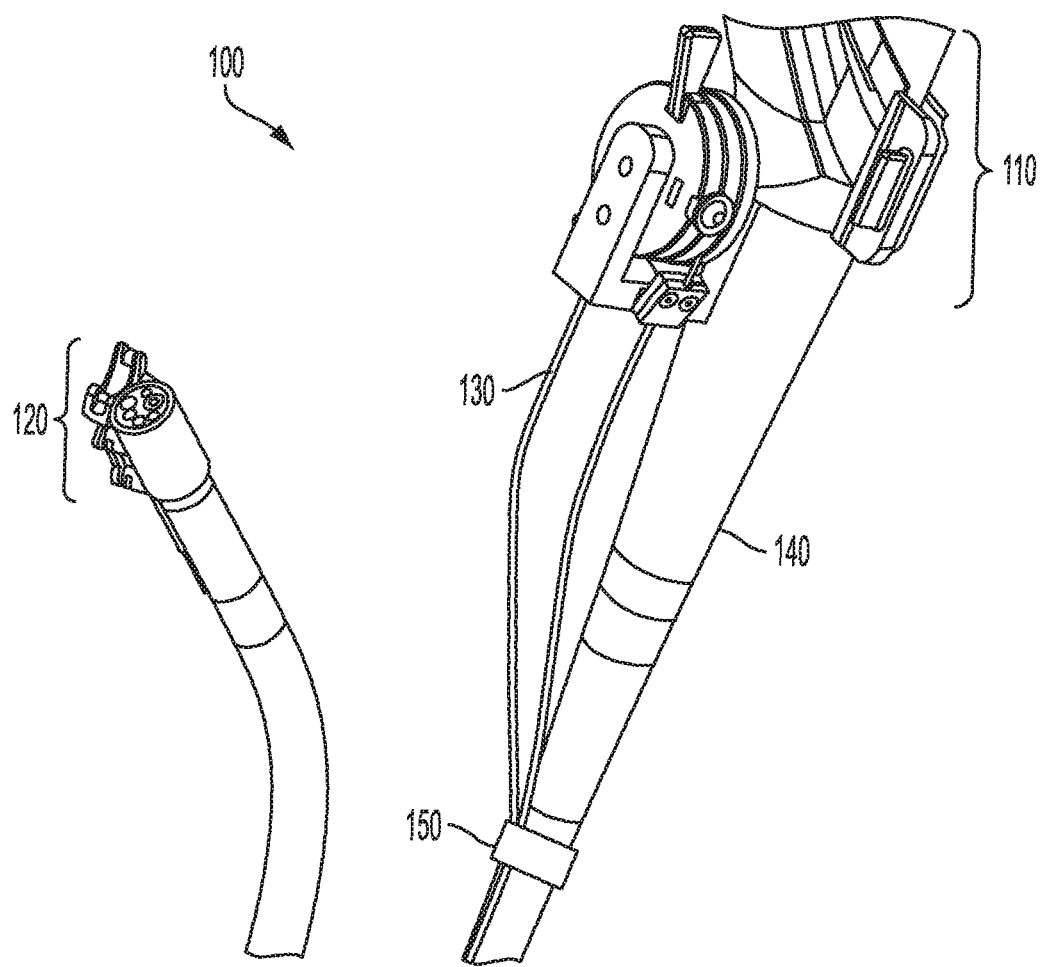
FIG. 1 is an illustration of an exemplary endoscopic suturing system, per an embodiment herein.

FIG. 1 is an illustration of an exemplary endoscopic suturing system 100 configured for use with an endoscope 140. As shown the exemplary endoscopic suturing system 100 comprises a distal assembly 120, a proximal assembly 110, and a cable 130. In some embodiments, the endoscopic suturing system 100 further comprises a cable fastener 150 which couples at least a portion of the cable 130 to the endoscope 140. In some embodiments, the cable fastener 150 removably couples at least a portion of the cable 130 to the endoscope 140. In some embodiments, the cable fastener 150 fastens the cable 130 to the endoscope 140 by wrapping around the cable 130 and the endoscope 140. In some embodiments, the cable fastener 150 fastens the cable 130 to the endoscope 140 by clamping to the cable 130 and the endoscope 140. In some embodiments, the cable fastener 150 fastens the cable 130 to the endoscope 140 by removably adhering the cable 130 to the endoscope 140. In some embodiments, the cable fastener 150 comprises a press-fit fastener, a clamp, an adhesive, a tape, a strap, a set screw, a hook and loop fastener, a magnet, or any combination thereof. In some embodiments, the endoscopic suturing system 100 comprises 1, 2, 3, 4, 5, 6, 7, 8, 9, 10, or more cable fasteners 150.

Proximal Assembly

Figure 2:
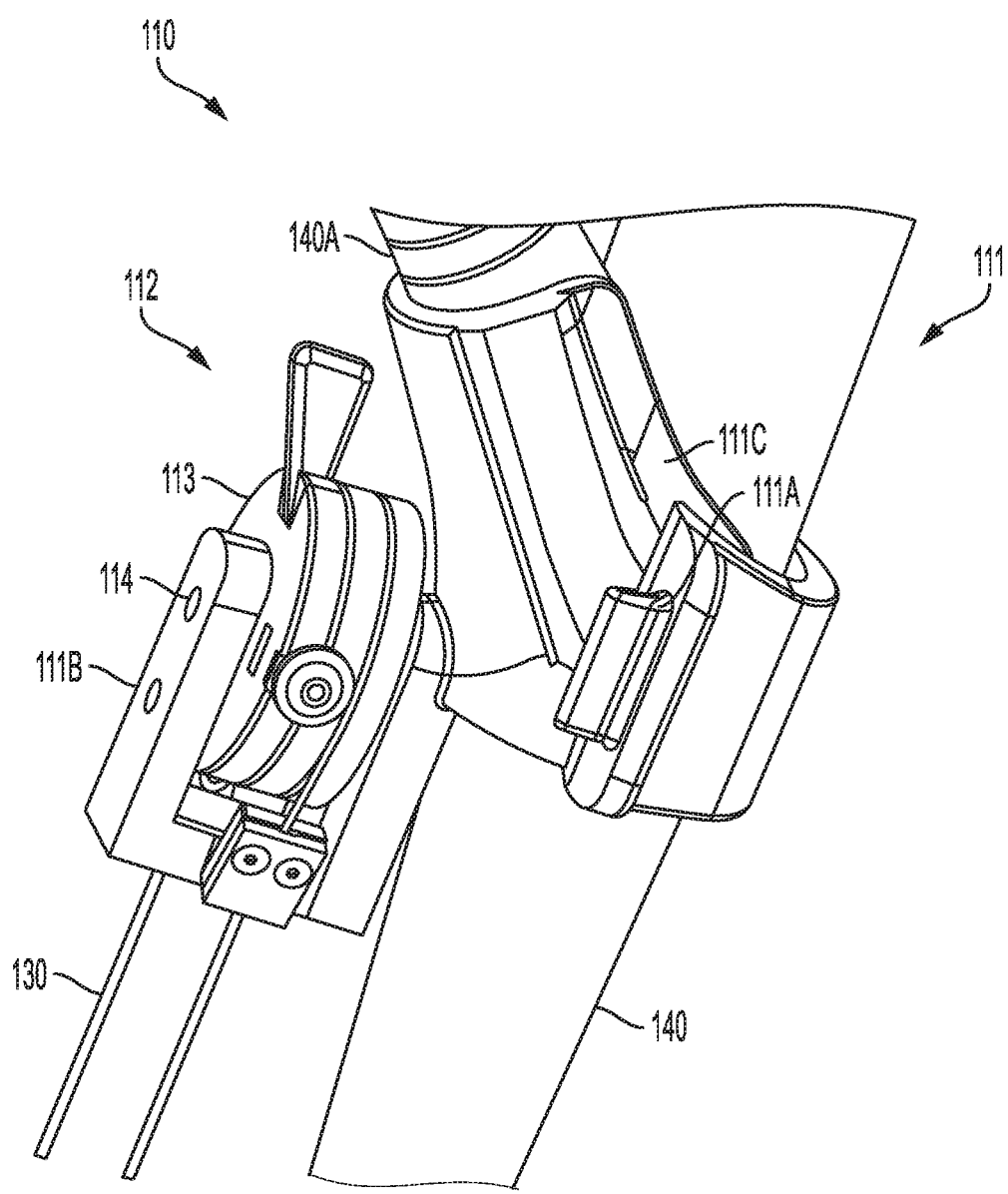
FIG. 2 is an illustration of an exemplary first proximal assembly coupled to an endoscope, per an embodiment herein.
Figure 3:
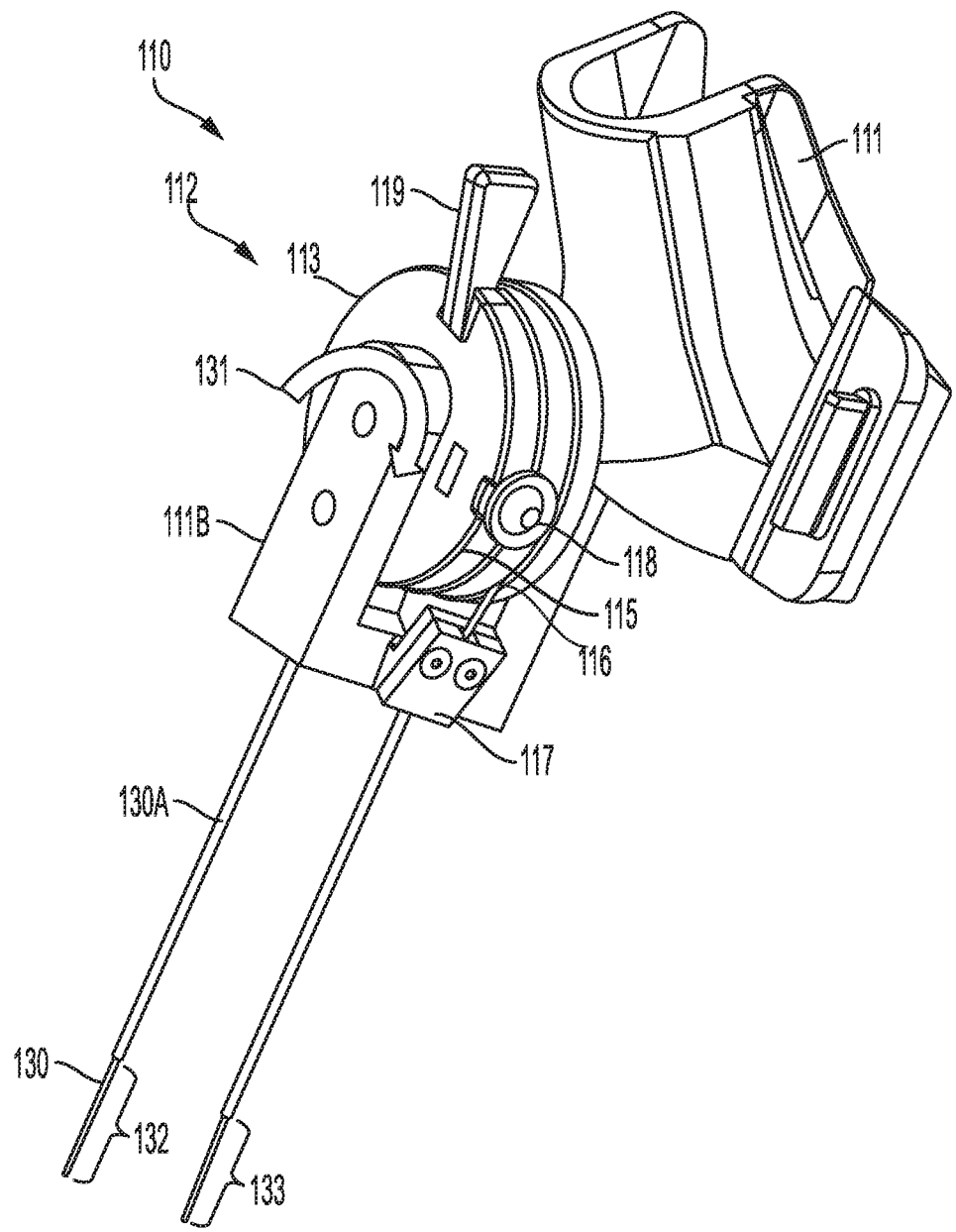
FIG. 3 is an illustration of a second exemplary proximal assembly, per an embodiment herein.

FIGS. 2 and 3 show illustration of an exemplary proximal assembly 110 coupled to an endoscope 140. As shown the exemplary proximal assembly 110 comprises a second housing 111 and an actuator 112. In some embodiments, the second housing 111 comprises a second housing fastener 111A, an actuator support portion 111B, and a main second housing body 111C. In some embodiments, the main second housing body 111C couples the second housing fastener 111A to the actuator support portion 111B. In some embodiments, the proximal assembly 110 has a length of about 10 mm to about 50 mm. In some embodiments, the proximal assembly 110 has a length of at most about 50 mm.

In some embodiments, the second housing 111 couples to the endoscope 140. In some embodiments, the second housing 111 removably couples to the endoscope 140. In some embodiments, the second housing 111 couples to the endoscope 140 and an endoscope biopsy port (or instrument channel port) 140A of the endoscope 140. In some embodiments, the second housing 111 removably couples to the endoscope 140 at a juncture between the endoscope 140 and the endoscope cable 140A. In some embodiments, the second housing 111 surrounds a portion of the endoscope 140, the endoscope cable 140A, or both. In some embodiments, the second housing 111 partially surrounds a portion of the endoscope 140, the endoscope cable 140A, or both. In some embodiments, the coupling of the second housing 111 to both the endoscope 140 and the endoscope cable 140A enables greater stability of the proximal assembly 110 on the endoscope 140.

In some embodiments, the second housing fastener 111A and the main second housing body 111C couple to the endoscope 140. In some embodiments, the second housing fastener 111A and the main second housing body 111C removably couple to the endoscope 140. In some embodiments, the second housing fastener 111A and the main second housing body 111C couple to the endoscope 140 and an endoscope biopsy port (or instrument channel port) 140A of the endoscope 140. In some embodiments, the second housing fastener 111A and the main second housing body 111C removably couple to the endoscope 140 at a juncture between the endoscope 140 and the endoscope cable 140A. In some embodiments, the second housing fastener 111A and the main second housing body 111C surround a portion of the endoscope 140, the endoscope cable 140A, or both. In some embodiments, the second housing fastener 111A and the main second housing body 111C partially surround a portion of the endoscope 140, the endoscope cable 140A, or both. In some embodiments, the coupling of the second housing fastener 111A and the main second housing body 111C to both the endoscope 140 and the endoscope cable 140A enables greater stability of the proximal assembly 110 on the endoscope 140. In some embodiments, the second housing 111A fastener rigidly connects to the endoscope 140 without allowing any relative motion between the endoscope 140 and the second housing 111.

As shown, the main second housing body 111C comprises a first concave portion and a second concave portion. In some embodiments, the first concave surrounds a portion of the endoscope 140. In some embodiments, the second concave surrounds a portion of the endoscope cable 140A. In some embodiments, the first concave portion has an inner diameter equal to or greater than an outer diameter of the endoscope 140. In some embodiments, the inner diameter of the first concave portion is about 5 mm to about 50 mm. In some embodiments, the second concave portion has an inner diameter equal to or greater than an outer diameter of the endoscope cable 140A. In some embodiments, the inner diameter of the second concave portion is about 5 mm to about 50 mm. In some embodiments, an angle between a centerline of the first concave portion and a centerline of a second concave portion is about 30 degrees. In some embodiments, an angle between a centerline of the first concave portion and a centerline of a second concave portion is about 5, 10, 15, 20, 25, 30, 35, 40, 45, 50, 55, 60, 65, 70, 75, 80, 85, 90 degrees including increments therein. In some embodiments, the an angle between a centerline of the first concave portion and a centerline of a second concave portion is from about 5 to about 90 degrees, from about 10 to about 90 degrees, from about 10 to about 80 degrees, from about 20 to about 70 degrees, from about 5 to about 60 degrees, from about 10 to about 60 degrees, from about 20 to about 60 degrees, from about 10 to about 50 degrees, from about 5 to about 45 degrees, from about 10 to about 50 degrees, from about 15 to about 65 degrees, from about 25 to about 65 degrees, from about 30 to about 60 degrees, from 5 to 90 degrees, from 10 to 90 degrees, from 10 to 80 degrees, from 20 to 70 degrees, from 5 to 60 degrees, from 10 to 60 degrees, from 20 to 60 degrees, from 10 to 50 degrees, from 5 to 45 degrees, from 10 to 50 degrees, from 15 to 65 degrees, from 25 to 65 degrees, or from 30 to 60 degrees. In some embodiments, at least one of the first concave portion or the second concave portion of the main second housing body 111C has a uniform thickness.

In some embodiments, the main second housing body 111C comprises a fastening mechanism that couples to the second housing fastener 111A. As shown, the fastening mechanism of the main second housing body 111C comprises a plurality of raised ridges. Alternatively, in some embodiments, the fastening mechanism of the main second housing body 111C comprises a tie, a string, a band, a hook and loop fastener, a tape, a strap, a magnet, a cinch, a press fit, a set screw, an adhesive, or any combination thereof.

In some embodiments, the second housing fastener 111A couples with the fastening mechanism of the main second housing body 111C to secure the proximal assembly 110 to the endoscope 140. As seen the exemplary second housing fastener 111A comprises a strap extending from the main second housing body 111C. In some embodiments, the second housing fastener 111A and the main second housing body 111C are coupled by a hinge (not shown), wherein the second housing fastener 111A rotates about the main second housing body 111C via the hinge. In some embodiments, the second housing fastener 111A comprises a flexible strap that is permanently attached to the main second housing body 111C. In some embodiments, the second housing fastener 111A comprises a flexible strap that is over-molded onto the main second housing body 111C. In some embodiments, at least a portion of the second housing fastener 111A is flexible. Further, as shown, the terminus of the strap of the second housing fastener 111A comprises a hook that engages and disengages with the fastening mechanism of the main second housing body 111C. Additionally, as shown, in some embodiments, the fastening mechanism of the main second housing body 111C comprises an extrusion for gripping by a user during engagement and disengagement with the fastening mechanism of the main second housing body 111C. In some embodiments, the strap of the second housing fastener 111A comprises a hook that engages and disengages with the fastening mechanism of the main second housing body 111C. In some embodiments, the strap of the second housing fastener 111A and the fastening mechanism of the main second housing body 111C enable the second housing 111 to secure to a variety of sizes of endoscopes 140. In some embodiments, the hook of the second housing fastener 111A and the In some embodiments, the second housing 111 comprises 1, 2, 3, 4, 5, 6, 7, 8, 9, 10, or more second housing fasteners 111A. Alternatively, the second housing 111 does not couple to the endoscope 140. In some embodiments, the proximal assembly 110 is configured to be used as a handheld assembly. In some embodiments, the proximal assembly 110 is configured to be mounted to a surface, a rod, a stand, or any combination thereof.

In some embodiments, the wheel 113 is confined to rotate about at least degree of freedom with respect to the second housing 111. In some embodiments, the actuator support portion 111B comprises a hole to house a pin 114. In some embodiments, the actuator support portion 111B encircles at least a portion of the actuator 112. As seen, the exemplary actuator 112 comprises a wheel 113 that rotates about the pin 114 within the second housing 111. In some embodiments, the actuator 112 freely rotates about the pin 114 within the second housing 111. In some embodiments, at least one of the second housing 111, the pin 114, or the wheel 113 comprise a bearing that allows the wheel 113 to rotate about the pin 114 within the second housing 111. In some embodiments, at least one of the wheel 113 or the actuator support portion 111B comprise a lock, wherein rotation of the wheel 113 about the pin 114 is temporarily locked in a single position by the lock. In some embodiments, at least one of the second housing 111, the pin 114, or the wheel 113 comprise a divot, a ridge, a valley, a spring, or any combination thereof, that couple and decouple upon rotation of the wheel 113 about the pin 114 to allow for manually advancement of the wheel 113. In some embodiments, the divot, ridge, valley, spring, or any combination thereof, couple and decouple upon rotation of the wheel 113 about the pin 114 to provides a tactile feedback indicating an incrementation or angle of rotation. Additionally, in some embodiments, the actuator 112 further comprises a spring, a divot, a magnet or any combination thereof to bias the actuator 112 to one or more positions relative to the second housing 111.

Alternatively, in some embodiments, the second housing 111 does not have a pin 114, wherein the wheel 113 rotates about a protrusion in the actuator support portion 111B. In some embodiments, the wheel 113 comprises the pin 114 or an extrusion wherein the wheel 113 and the pin 114 or extrusion rotate about a corresponding hole within the actuator support portion 111B. Alternatively, in some embodiments, the wheel 113 is confined to rotate with respect to the second housing 111 via a circular channel, a spring, a cam, a pin, a screw, a bolt, or any combination thereof. In some embodiments, the pin 114 is removable for cleaning of the wheel 113. As shown in FIG. 3, the wheel 113 is round. In some embodiments, the round wheel 113 has an outer diameter. Alternatively, in some embodiments, the wheel 113 has a shape comprising a triangle, a square, a pentagon, a hexagon, or any other polygon.

As shown the exemplary actuator 112 comprises a knob 119 that allows a user to rotate the wheel 113 about the second housing 111. In some embodiments, the knob 119 further serves as an indicator of the position of the actuator 112 with respect to the second housing 111. In some embodiments, the knob 119 prevents the wheel 113 from rotating more than 360 degrees in a primary direction 131, or rotating more than 360 degrees in a secondary direction opposite the primary direction 131. In some embodiments, the wheel 113 rotates up to about 360 degrees in a primary direction 131, and rotates up to about 360 degrees in a secondary direction opposite the primary direction 131. In some embodiments, the wheel 113 rotates up to about 20 degrees, up to about 30 degrees, up to about 40 degrees, up to about 50 degrees, up to about 60 degrees, up to about 70 degrees, up to about 80 degrees, up to about 90 degrees, up to about 110 degrees, up to about 120 degrees, up to about 130 degrees, up to about 140 degrees, up to about 150 degrees, up to about 160 degrees, up to about 170 degrees, up to about 180 degrees, up to about 190 degrees, up to about 200 degrees, up to about 210 degrees, up to about 220 degrees, up to about 230 degrees, up to about 240 degrees, up to about 250 degrees, up to about 260 degrees, up to about 270 degrees, up to about 280 degrees, up to about 290 degrees, up to about 300 degrees, up to about 310 degrees, up to about 320 degrees, up to about 330 degrees, up to about 340 degrees, up to about 350 degrees, or up to about 360 degrees in a primary direction 131, and rotates up to about 20 degrees, up to about 30 degrees, up to about 40 degrees, up to about 50 degrees, up to about 60 degrees, up to about 70 degrees, up to about 80 degrees, up to about 90 degrees, up to about 110 degrees, up to about 120 degrees, up to about 130 degrees, up to about 140 degrees, up to about 150 degrees, up to about 160 degrees, up to about 170 degrees, up to about 180 degrees, up to about 190 degrees, up to about 200 degrees, up to about 210 degrees, up to about 220 degrees, up to about 230 degrees, up to about 240 degrees, up to about 250 degrees, up to about 260 degrees, up to about 270 degrees, up to about 280 degrees, up to about 290 degrees, up to about 300 degrees, up to about 310 degrees, up to about 320 degrees, up to about 330 degrees, up to about 340 degrees, up to about 350 degrees, or up to about 360 degrees in a secondary direction opposite the primary direction 131. In some embodiments, the actuator 112 further comprises an indicator that indicates its position relative to the second housing 111. Alternatively, in some embodiments, the actuator 112 comprises or further comprises a pulley, a wheel, a clamp, a knot, a post, a gear, a cog, a chain, or any combination thereof.

As shown the exemplary wheel 113 comprises a first channel 115 that receives a first portion of a cable 132 and a second channel 116 that receives a second cable portion 133. In some embodiments, at least one of the first channel 115 or the second channel 116 have a circular cross section. In some embodiments, the wheel 113 does not comprise the second channel 116. In such embodiments, the first channel 115 comprises a single spiral channel. In some embodiments, at least one of the first channel 115 or the second channel 116 have an inner width equal to or greater than a width of the cable 130. In some embodiments, a radius of the first channel 115 is equal to a radius of the second channel 116. In some embodiments, the radius of the first channel 115 is greater than the radius of the second channel 116. In some embodiments, the radius of the first channel 115 is less than the radius of the second channel 116. In some embodiments, a circumference of the first channel 115 is equal to a circumference of the second channel 116. In some embodiments, the circumference of the first channel 115 is greater than the circumference of the second channel 116. In some embodiments, the circumference of the first channel 115 is less than the circumference of the second channel 116. In some embodiments, the first channel 115 and the second channel 116 are concentric. In some embodiments, the first channel 115 and the second channel 116 are not concentric. In some embodiments, the first channel 115 and the second channel 116 overlap.

In some embodiments, the actuator 112 further comprises a first fastener 118 that couples the first cable portion 132 to the wheel 113, and a second fastener (not shown) that couples the second cable portion 130 to the actuator 112. In some embodiments, the first fastener 118 maintains the first cable portion 133 within the first channel 115. In some embodiments, the second fastener maintains the second cable portion 133 within the second channel 116. In some embodiments, the first fastener 118 prevents the wheel 113 from rotating more than 360 degrees in the primary direction 131, or rotating more than 360 degrees in a secondary direction opposite the primary direction 131. In some embodiments, the proximal assembly 110 comprises 1, 2, 3, 4, 5, 6, 7, 8, 9, 10, or more fasteners. In some embodiments, the wheel 113 does not comprise the first fastener 118 or the second fastener. In some embodiments, the wheel 113 comprises a knob, a tie, or an extrusion that couples the first cable portion 132, the second cable portion 133, or both to the wheel 113. In some embodiments, the first cable portion 132 and the second cable portion 133 are connected, whereas the cable 130 comprises one or two components. In some embodiments, cable 130 comprises two or more components In some embodiments, the first cable portion 132 and the second cable portion 133 are not connected, whereas the cable 130 comprises a two or more components. In some embodiments, at least one of the first cable portion 132 or the second cable portion 133 are constantly in tension during rotation of the wheel 113 of the actuator 112. In some embodiments, at least one of the first cable portion 132 or the second cable portion 133 do not have slack during rotation of the wheel 113 of the actuator 112. In some embodiments, at least one of the first cable portion 132 or the second cable portion 133 are in tension when the wheel 113 of the actuator 112 is rotated in the primary direction 131. In some embodiments, at least one of the first cable portion 132 or the second cable portion 133 are in tension when the wheel 113 of the actuator 112 is rotated in the secondary direction opposite the primary direction 131.

In some embodiments, per FIG. 3, when rotated in the primary direction 131, the actuator 112 translates the first cable portion 132 away from the second housing 111 by a first distance, and translates the second cable portion 133 towards the second housing 111 by a second distance. In some embodiments, when rotated in a secondary direction opposite the primary direction 131, the actuator 112 translates the first cable portion 132 towards from the second housing by a third distance, and translates the second cable portion 133 away the second housing 111 by a fourth distance. In some embodiments, the first distance, the second distance, the third distance, and the fourth distance are equal. In some embodiments, at least two of the first distance, the second distance, the third distance, and the fourth distance are equal. In some embodiments, the first distance equals the third distance and the second distance equals the fourth distance.

As seen in FIG. 3, in some embodiments, the endoscopic suturing system 100 further comprises a sheath 130A that surrounds at least a portion of the cable 130. In some embodiments, the cable 130 translates freely back and forth in one direction within the sheath 130A. In some embodiments, the cable 130 and the sheath 130A comprise a Bowden cable. In some embodiments, the cable 130 comprises a multi-strand cable, a single strand cable, a rope, a thread, a string, a wire, or any combination thereof. In some embodiments, the cable 130 comprises 1, 2, 3, 4, 5, 6, 7, 8, 9, 10 or more cables. In some embodiments, at least a portion of the cable 130 is not covered by the cable sheath 130A. In some embodiments, the cable 130 is rigid. In some embodiments, the cable 130 is not elastic. In some embodiments, the cable sheath 130A comprises a hollow tube that protects the cable 130 within. In some embodiments, the cable sheath 130A is rigid. In some embodiments, the cable sheath 130A is not elastic.

As shown, the second housing 111 comprises a proximal sheath fastener 117 that couples the sheath 130A to the second housing 111. As shown, the sheath fastener 117 is connected to the actuator support portion 111B of the second housing 111. Alternatively, in some embodiments, the sheath fastener 117 is connected to any portion of the second housing 111. In some embodiments, the proximal sheath fastener 117 fixes a portion of the sheath 130A with respect to the second housing 111 such that the cable 130 is allowed to travel within the sheath 130A upon rotation of the wheel 113. In some embodiments, the proximal sheath fastener 117 prevents the wheel 113 from rotating more than 360 degrees in the primary direction 131, or rotating more than 360 degrees in a second direction opposite the primary direction 131. As shown, the exemplary proximal sheath fastener 117 comprises a clamp. In some embodiments, the clamp comprises a first plate, a second plate, and one or more screws that compress the cable 130 between the first plate and the second plate. Alternatively in some embodiments, the proximal sheath fastener 117 comprises a screw, a tie, a tape, a bolt, a nut, or any combination thereof. In some embodiments, the proximal assembly 110 comprises at least one proximal sheath fastener 117 for the first cable portion 132, and at least one proximal sheath fastener 117 for the second cable portion 133. In some embodiments, the proximal assembly 110 comprises a single proximal sheath fastener 117 for both the first cable portion 132 and the second cable portion 133. In some embodiments, the proximal assembly 110 comprises 1, 2, 3, 4, 5, 6, 7, 8, 9, 10, or more proximal sheath fasteners 117.

In some embodiments, the cable 130 is composed of fabric, metal, plastic, carbon, or any combination thereof. In some embodiments, at least one of the second housing 111, the actuator 112, the wheel 113, the pin 114, the proximal sheath fastener 117, the first fastener 118, or the sheath 130A are composed of plastic, metal, fiberglass, carbon fiber, wood, or any combination thereof. In some embodiments, the actuator does not comprise at least one of a crank, a gear, a rack, or a pinion.

First Distal Assembly

Figure 4:
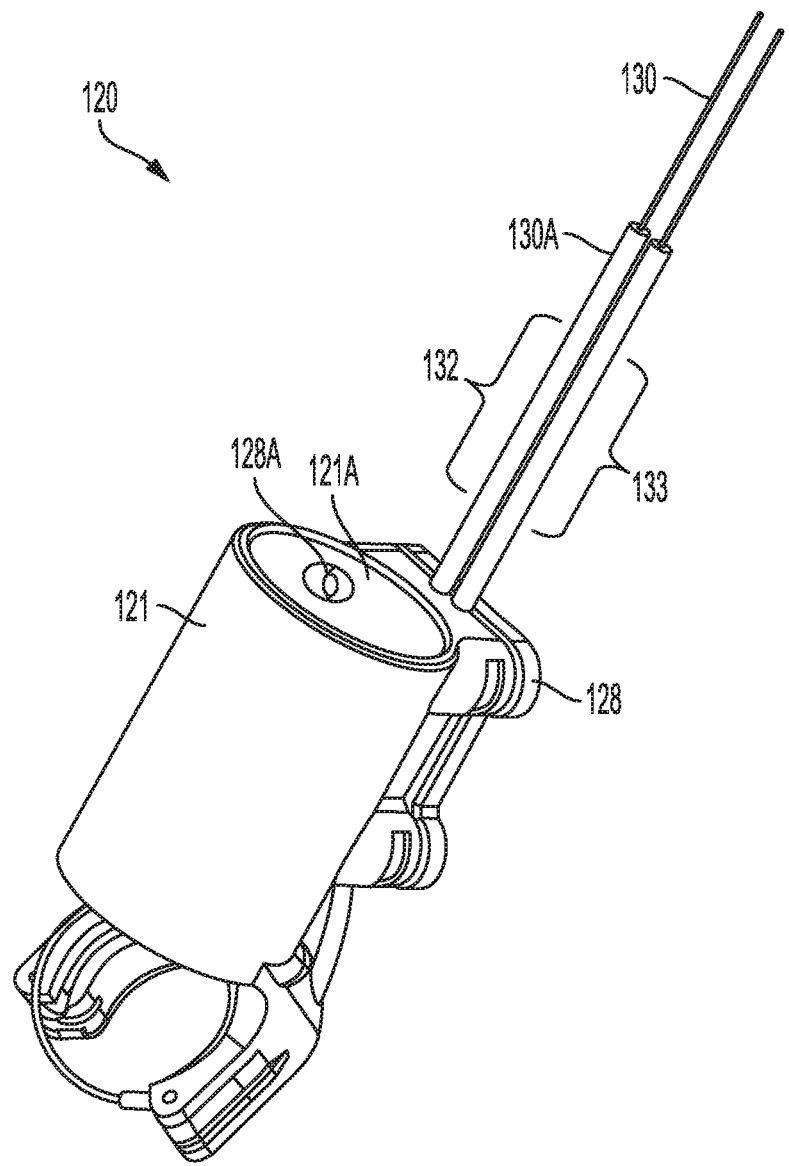
FIG. 4 is an illustration of a third exemplary distal assembly, per an embodiment herein.
Figure 5:
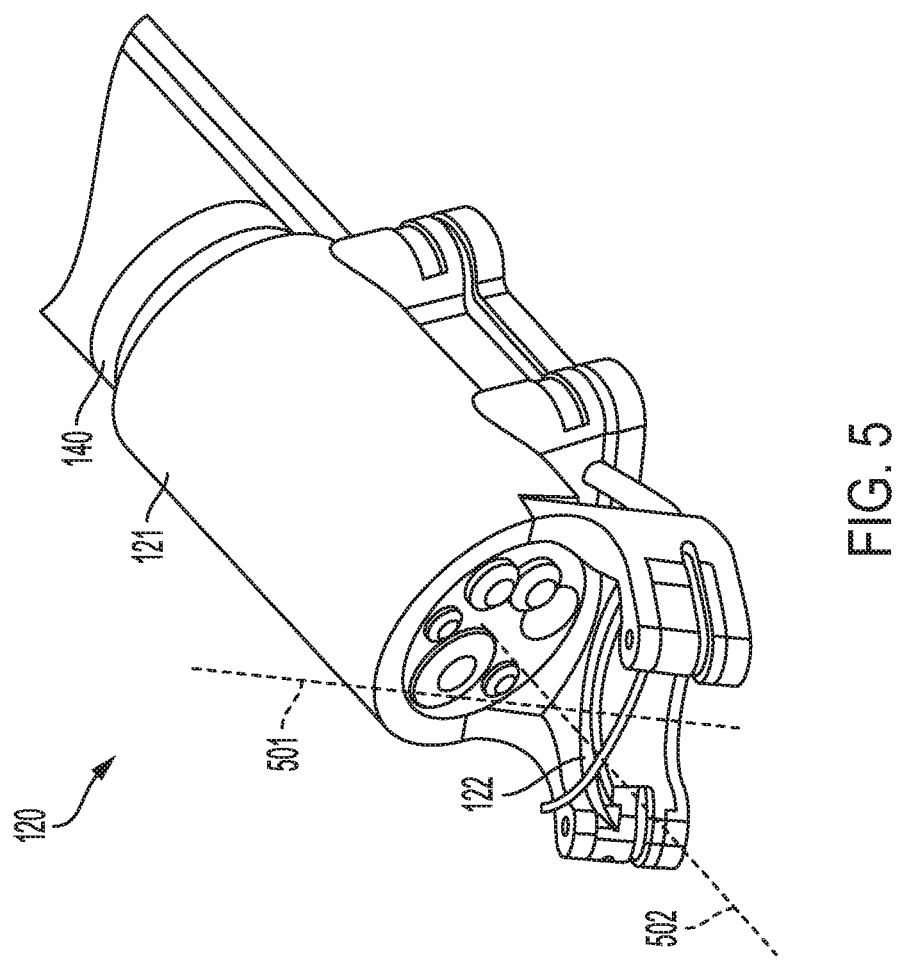
FIG. 5 is an illustration of the exemplary first distal assembly on an endoscope, per an embodiment herein.
Figure 6:
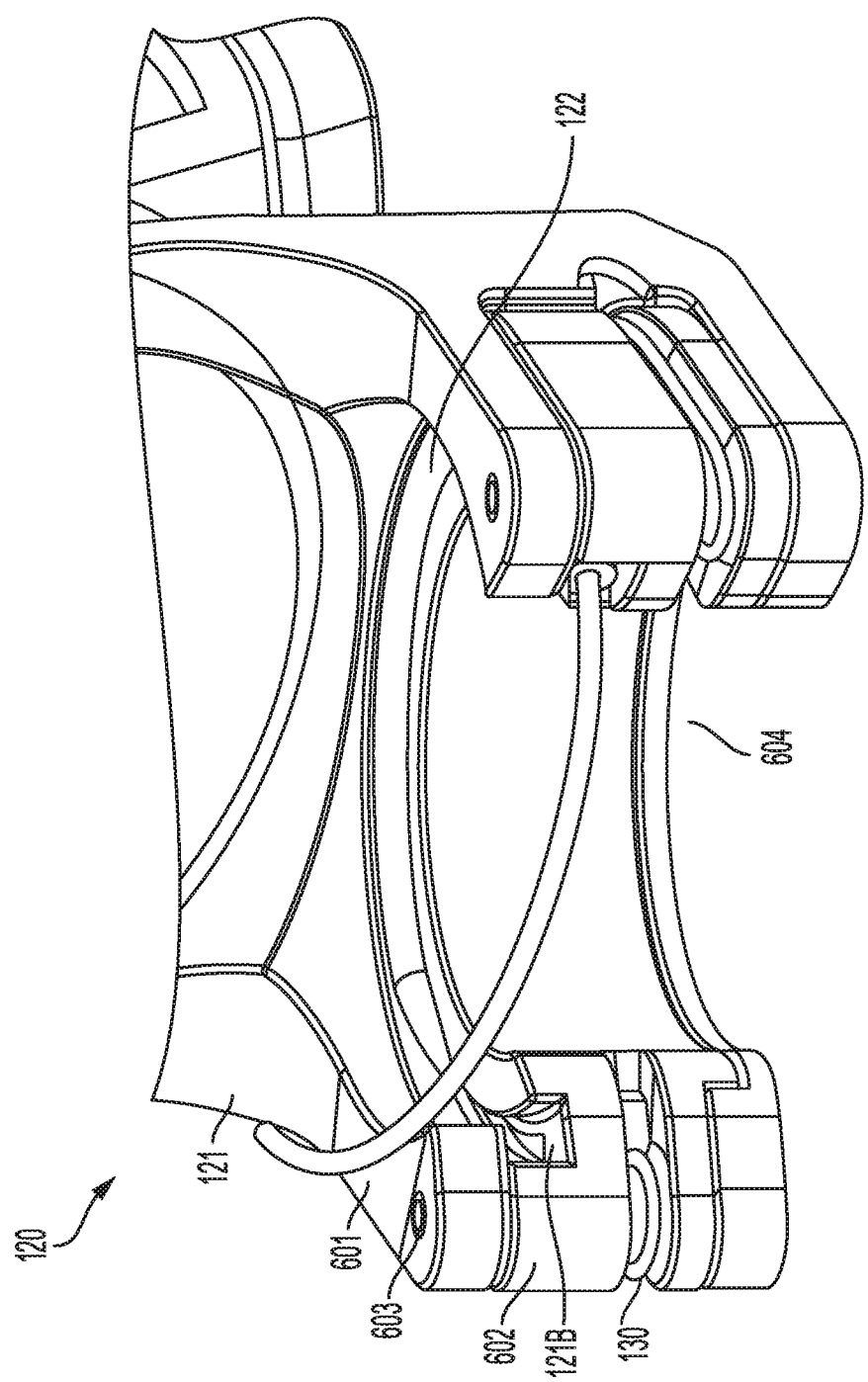
FIG. 6 is a detailed illustration of the exemplary first distal assembly, per an embodiment herein.

FIGS. 4 and 5 show illustrations of an exemplary first distal assembly 120. As shown the exemplary first distal assembly 120 comprises a first housing 121 comprising an endoscope fastener 121A. In some embodiments, the distal assembly is c-shaped, or comprises a c-shaped portion, thus being referred to as being c-shaped. In some embodiments, the distal assembly has an arcuate needle guide 121B that is c-shaped, thus providing the distal assembly a c-shape. In some embodiments the portion of the distal assembly that is c-shaped is the arcuate needle guide, at least. The devices, apparatus, and systems actuate an arcuate needle (as used herein, an "arcuate needle" is synonymous with a "circular needle" and is an arced needle that is not fully circular, but travels in a circular path or a substantially circular path) through the c-shaped portion of a distal assembly, wherein such c-shaped portion of the distal assembly is non-perpendicularly angled relative to the major axis of the endoscope and has a non-aligned angle relative to the major axis 502 of the endoscope (see needle axis 501, elsewhere herein). As such, a tissue grabber is not necessary when suturing using the arcuate needle of the distal assembly, as the distal assembly is easily manipulated to seat the tissue between open ends of the c-shape portion of the distal assembly and into the gap formed by the "C" of the c-shaped portion of the distal assembly for suturing once in such position without separate support required. In some embodiments, the ends of the c-shaped portion of the distal assembly form an angle relative to the needle axis 501 that is less than 180 degrees, is less than about 170 degrees, is less than about 160 degrees, is less than about 150 degrees, is less than about 145 degrees, is less than about 120 degrees, is less than about 100 degrees, is about 20 to about 170 degrees, is about 30 to about 150 degrees, about 40 to about 120 degrees, about 45 to about 110 degrees, about 50 to about 120 degrees, or is about 60 to about 120 degrees. In some embodiments, such angle is measured from the central axis of pulley 2121AA or the equivalent pin thereof, depending on the embodiment. In some embodiments, such angle is measured from the termini of the c-shaped portion that form the minimum angle possible to measure for such angle.

In some embodiments, the endoscope fastener 121A couples the first housing 121 to an endoscope 140. In some embodiments, the endoscope fastener 121A removably couples the first housing 121 to the endoscope 140. As shown, the endoscope fastener 121A comprises a press fit fastener. In some embodiments, the press fit endoscope fastener 121A attaches to the endoscope 140 by firmly pressing the press fit endoscope fastener 121A onto a distal end of the endoscope 140. In some embodiments, the press fit endoscope fastener 121A attaches to the endoscope 140 by firmly pressing and rotating the press fit endoscope fastener 121A onto a distal end of the endoscope 140. In some embodiments, the press fit endoscope fastener 121A detaches from the endoscope 140 by firmly pulling the press fit endoscope fastener 121A off the distal end of the endoscope 140. In some embodiments, the press fit endoscope fastener 121A detaches from the endoscope 140 by firmly pulling and rotating the press fit endoscope fastener 121A off the distal end of the endoscope 140. Alternatively, in some embodiments, the endoscope fastener 121A comprises a clamp, an adhesive, a tape, a strap, a set screw, a hook and loop fastener, a magnet, or any combination thereof. In some embodiments, the first distal assembly 120 comprises 1, 2, 3, 4, 5, 6, 7, 8, 9, 10, or more endoscope fasteners 121A.

As shown, in some embodiments, the endoscope fastener 121A is rounded. In some embodiments, the endoscope 140 has a proximal outer diameter of about 5 mm to about 16 mm. As such, in some embodiments, the endoscope fastener 121A has an inner diameter of about 5 mm to about 16 mm. In some embodiments, the endoscope fastener 121A has an inner diameter of at least about 5 mm. In some embodiments, the endoscope fastener 121A has an inner diameter of at most about 16 mm. In some embodiments, the press fit endoscope fastener 121A has a diameter equal to or lesser than the diameter of the endoscope 140. In some embodiments, the endoscope fastener 121A has a diameter equal to or greater than the diameter of the endoscope 140. In some embodiments, the endoscope fastener 121A is tapered and has a first inner diameter and a second inner diameter, wherein the first inner diameter is distal to the second inner diameter. In some embodiments, the first inner diameter is greater than the second inner diameter. In some embodiments, the second inner diameter is greater than the first inner diameter. In some embodiments, the diameter of the endoscope fastener 121A is measured as a maximum, a minimum, or an average interior width. In some embodiments, the diameter of the endoscope 140 is measured as a maximum, a minimum, or an average exterior width. Alternatively, in some embodiments, the endoscope fastener 121A has a cross sectional shape comprising a triangle, a square, a hexagon, or any other polygon. In some embodiments, the endoscope fastener 121A has an inner length of about 10 mm to about 30 mm. In some embodiments, the inner length of the endoscope fastener 121A is measured as a minimum, a maximum, or an average length from a distal termination of the endoscope fastener 121A to a proximal termination of the endoscope fastener 121A. In some embodiments, the inner length of the endoscope fastener 121A is measured as a minimum, a maximum, or an average normal length from a distal termination of the endoscope fastener 121A to a proximal termination of the endoscope fastener 121A.

As shown in FIG. 4, the exemplary first distal assembly 120 further comprises a distal sheath fastener 128 that couples a portion of the sheath 130A to the first housing 121. As shown, the first housing 121 comprises a distal sheath fastener 117 that couples the sheath 130A to the first housing 121. In some embodiments, the distal sheath fastener 117 fixes a portion of the sheath 130A with respect to the first housing 121, such that the cable 130 is allowed to travel within the sheath 130A upon rotation of the wheel. As shown, the exemplary distal sheath fastener 128 comprises a clamp. In some embodiments, the distal sheath fastener 128 comprises a plate and one or more sheath fastener screws 128A that compress the cable sheath 130A between the plate and the first housing 121. Alternatively in some embodiments, the distal sheath fastener 128 comprises a screw, a tie, a tape, or any combination thereof. In some embodiments, the first housing 112 comprises at least one distal sheath fastener 128 for the first cable portion 132, and at least one distal sheath fastener 128 for the second cable portion 133. In some embodiments, the first housing 112 comprises a distal sheath fastener 128 for both the first cable portion 132 and the second cable portion 133. In some embodiments, a portion of the cable sheath 130A extends past the termination of the distal sheath fastener 128 and into the first housing 121. In some embodiments, the distal assembly 120 comprises 1, 2, 3, 4, 5, 6, 7, 8, 9, 10, or more distal sheath fasteners 128. Alternatively, in some embodiments, the distal sheath fastener 128 comprises a clamp, a tie, a band, a hook and loop fastener, an adhesive, or any combination thereof.

In some embodiments, per FIG. 5, an angle between a needle axis 501 and a proximal axis (or major axis) 502 of the endoscope 140 is about 5 degrees to about 85 degrees. In some embodiments, an angle between a the needle axis 501 and a proximal axis 502 of the endoscope 140 is adjustable within about 5 degrees to about 85 degrees. In some embodiments, a specific angle between the needle axis 501 and a proximal axis 502 of the endoscope 140 allows a camera of the endoscope 140 to view the entrance, the exit, or both of the arcuate needle the tissue that is being sutured. In some embodiments, the needle axis 501 is defined as an axis normal to a plane of symmetry of the arcuate needle 123 and coincident with a centerpoint of the radius of the arcuate needle 123. In some embodiments, the proximal axis 502 of the endoscope 140 is defined as the center axis or major axis of a distal portion of the endoscope 140. In some embodiments, the proximal axis 502 of the endoscope 140 is defined as the center axis of the endoscope fastener 121A of the first housing 112. In some embodiments, the angle between a center axis 501 of the arcuate needle guide 121B and a proximal axis 502 of the endoscope 140 is defined as a maximum, a minimum, or an average angle.

FIGS. 6-9 show detailed illustrations of the exemplary first distal assembly 120. Per FIG. 6, the exemplary first housing 121 comprises a primary first housing portion 601, a secondary first housing portion 602 and a pin fastener 603. In some embodiments, the secondary first housing portion 602 fits within the primary first housing portion 601. In some embodiments, the primary first housing portion 601 and the secondary first housing portion 602 are adjoined by the pin fastener 603. In some embodiments, the primary first housing portion 601 and the secondary first housing portion 602 are removably adjoined by the pin fastener 603. In some embodiments, the primary first housing portion 601 and the secondary first housing portion 602 are made of the same material. In some embodiments, the primary first housing portion 601 and the secondary first housing portion 602 are made of different materials. As shown the exemplary pin fastener 603 comprises a press fit fastener, wherein the press fit fastener has an outer diameter greater than a diameter of a corresponding hole in the primary first housing portion 601 and the secondary first housing portion 602. Alternatively, in some embodiments, the pin fastener 603 comprises a screw, a bolt, a threaded feature, a nut, a rivet, an adhesive, a pulley, a bearing, a weld, or any combination thereof. As shown the exemplary first housing 121 comprises two pin fasteners 603. Alternatively, the exemplary first housing 121 comprises 1, 3, 4, 5, 6, 7, 8, 9, 10 or more pin fasteners 603.

Further, in some embodiments, the first distal assembly 120 comprises an arcuate needle 122 disposed within an arcuate needle guide 121B within the first housing 121. In some embodiments, at least one of the primary first housing portion 601 or the secondary first housing portion 602 comprise the arcuate needle guide 121B. In some embodiments, the arcuate needle 122 slides freely within the arcuate needle guide 121B. In some embodiments, the arcuate needle guide 121B constrains the arcuate needle 122 to rotate within one degree of freedom. In some embodiments, the arcuate needle guide 121B constrains the arcuate needle 122 to rotate within at least one rotational degree of freedom. As seen, the exemplary arcuate needle guide 121B encloses at least a portion of the arcuate needle 122. In some embodiments, the exemplary arcuate needle guide 121B encloses at least a portion of the arcuate needle 122, when it is positioned within the first housing 121. In some embodiments, the arcuate needle guide 121B has an interior width greater than a thickness of the arcuate needle 122. In some embodiments, the arcuate needle guide 121B has a cross sectional shape comprising a circle, a square, a rectangle, or any other polygon. In some embodiments, a gulf 604 is formed between a first termination of the arcuate needle guide 121B and a second opposing termination of the arcuate needle guide 121B within the first distal assembly 120. As seen therein, the arcuate needle guide 121B surrounds about 280 degrees of the cross sectional circumference of the arcuate needle 122. Alternatively, in some embodiments, the arcuate needle guide 121B surrounds about 100, 120, 140, 160, 180, 200, 220, 240, 260, 280, 300, 320 degrees or more of the cross sectional circumference of the arcuate needle 122, including increments therein.

In some embodiments, a gulf 604 is formed between a first pin fastener 603 and a second opposing pin fastener 603 within the first distal assembly 120. In some embodiments, the gulf 604 accepts a tissue for suturing by the arcuate needle 122. In some embodiments, the tissue is supported against the arcuate needle 122 throughout the suturing process. In some embodiments, the first distal assembly 120 does not comprise an anchor exchange catheter. In some embodiments, the first distal assembly 120 does not require a dedicated grabber to keep the tissue against the arcuate needle 122. In some embodiments, lack of a required dedicated grabber enables the use of a standard endoscope 140 without an additional dedicated working channel.

Figure 7:
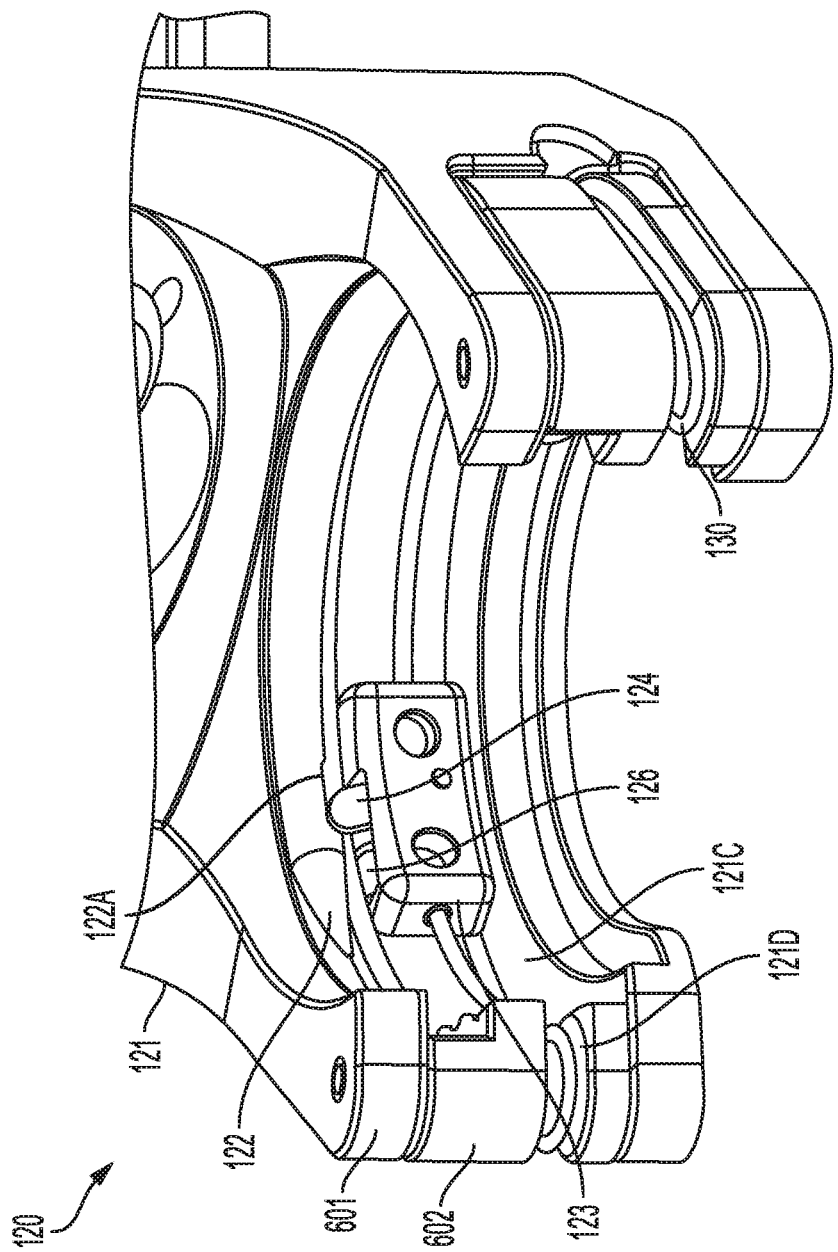
FIG. 7 is a detailed illustration of the exemplary first distal assembly in a first position with a portion of the shuttle guide removed, per an embodiment herein.
Figure 8:
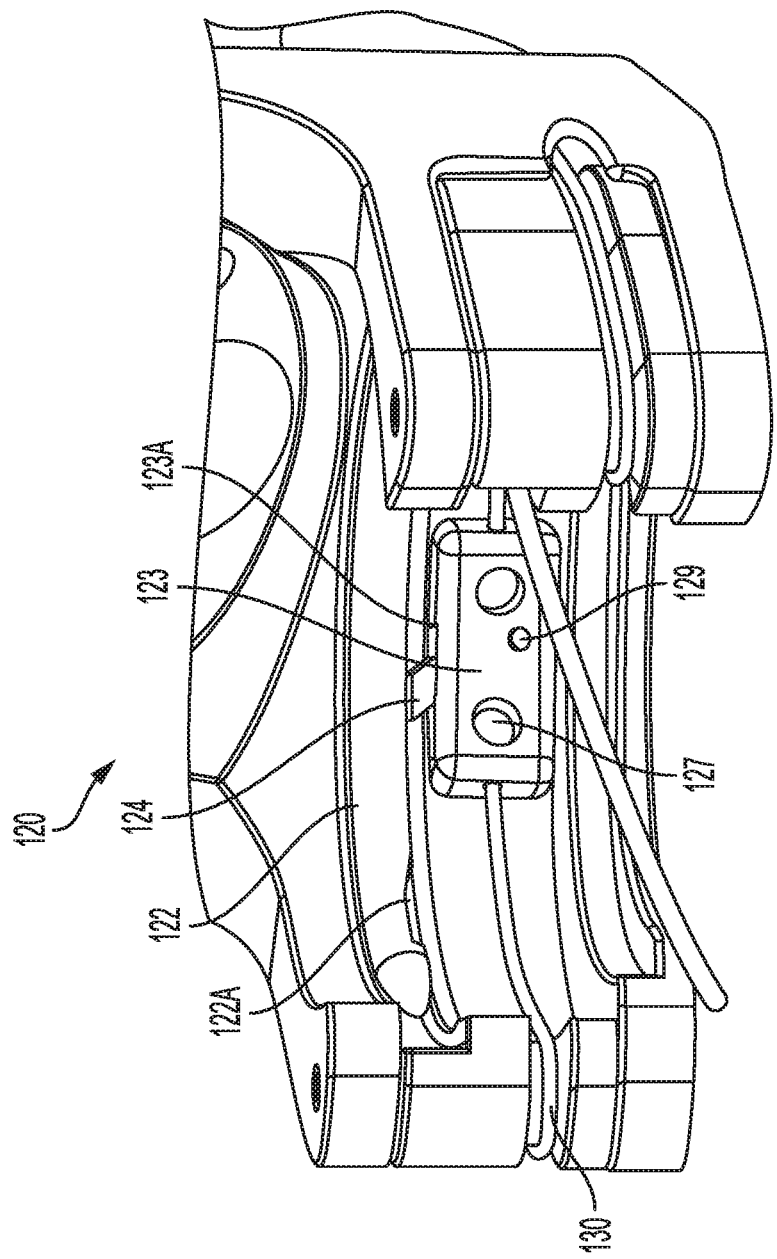
FIG. 8 is a detailed illustration of the exemplary first distal assembly in a second position with a portion of the shuttle guide removed, per an embodiment herein.
Figure 9:
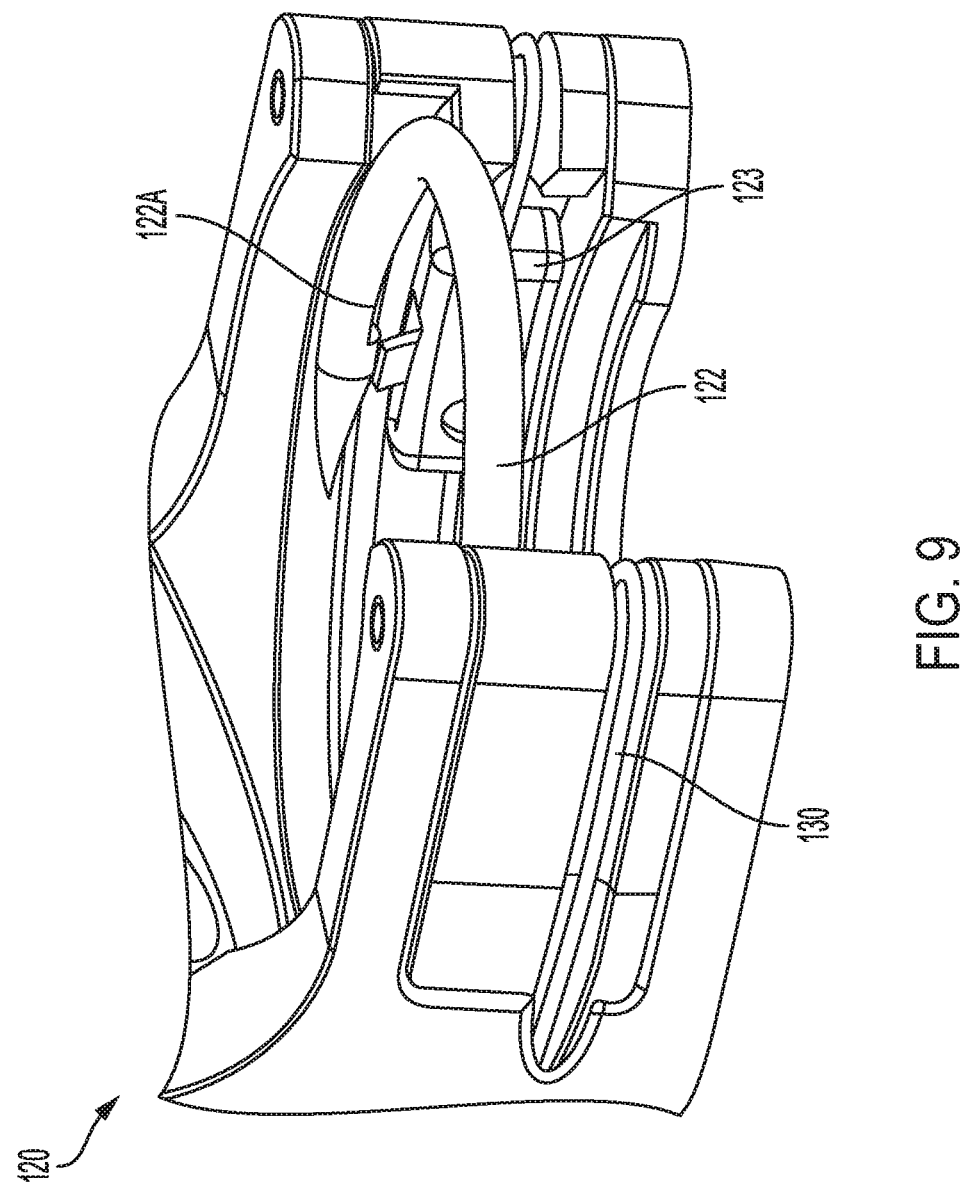
FIG. 9 is a detailed illustration of the exemplary first distal assembly in a third position with a portion of the shuttle guide removed, per an embodiment herein.

Per FIGS. 7-9, the exemplary first distal assembly 120 further comprises a shuttle 123 having a pawl 124. As shown the exemplary shuttle 123 translates within a shuttle guide 121C within the first housing 121. In some embodiments, at least one of the shuttle 123 or the shuttle guide 121C within the first housing 121 is arcuate. In some embodiments, the shuttle 123 slides within the shuttle guide 121C. In some embodiments, the shuttle 123 translates within the shuttle guide 121C about at least one degree of rotation. In some embodiments, the shuttle 123 translates about one degree of rotation within a 270 degree arc within the shuttle guide 121C. In some embodiments, the shuttle 123 translates in an arc about one degree of rotation over 90, 100, 110, 120, 140, 160, 180, 200, 220, 240, 260, 280, 300, 320, or greater degrees within the shuttle guide 121C. In some embodiments, at least one of the shuttle 123 or the shuttle guide 121C has a cross sectional shape comprising a circle, a square, a rectangle, or any other polygon.

In some embodiments, at least one of the primary first housing portion 601 or the secondary first housing portion 602 comprises the shuttle guide 121C. In some embodiments, the shuttle 123 slides within the shuttle guide 121C of the distal assembly 120. As shown, the shuttle 123 is arcuate to slide within the arcuate shuttle guide 121C. In some embodiments, the primary first housing portion 601 constrains a bottom surface of the shuttle 123, wherein the secondary first housing portion 602 constrains an inner surface, an outer surface, and a portion of the top surface of the shuttle 123. Alternatively, in some embodiments, at least one of the primary first housing portion 601 or the secondary first housing portion 602 constrain one or more of the bottom, inner, outer, and top surfaces of the shuttle 123. In some embodiments, the shuttle 123 is constrained by at least one of the primary first housing portion 601 or the secondary first housing portion 602 as it translates within the shuttle guide 121C. As shown, a bottom surface of the shuttle 123 contacts a portion of the primary first housing portion 601, while an inner portion and an outer portion of the shuttle 123 contacts a portion of the secondary first housing portion 602. In some embodiments, the shuttle 123 contacts at least one of the primary first housing portion 601 or the secondary first housing portion 602 as it translates within the shuttle guide 121C. As shown, an arcuate channel between the shuttle guide 121C and the arcuate needle guide 121B provides clearance for the pawl 124 to contact the arcuate needle 122 as the shuttle 123 translates through the shuttle guide 121C. In some embodiments, the arcuate channel has a width greater than a width of the pawl 124 but lesser than a width of the arcuate needle 122.

In some embodiments, the inner surface of the shuttle 123 is defined as a surface of the shuttle 123 that is closest to the needle axis 501. In some embodiments, the outer surface of the shuttle 123 is defined as a surface of the shuttle 123 that is farthest from the needle axis 501. In some embodiments, the top surface of the shuttle 123 is defined as a surface of the shuttle 123 that is closest to the arcuate needle 122. In some embodiments, the bottom surface of the shuttle 123 is defined as a surface of the shuttle 123 that is furthest to the arcuate needle 122.

In some embodiments, the arc length of the shuttle guide 121C is equal to the distance traveled by at least one of the first cable portion or the second cable portion during rotation of the actuation wheel minus a width of the shuttle 123. In some embodiments, the shuttle 123 travels within the shuttle guide 121C a distance traveled by at least one of the first cable portion or the second cable portion during rotation of the actuation wheel. In some embodiments, a ratio between a length of the shuttle 123 and the arc length of the shuttle guide 121C is about 1:3 to about 1:15. In some embodiments, a ratio between a length of the shuttle 123 and an arc length of the shuttle guide 121C is at least about 1:3. In some embodiments, a ratio between a length of the shuttle 123 and an arc length of the shuttle guide 121C is at most about 1:15. In some embodiments, a ratio between the arc length of the shuttle guide 121C and a diameter of at least one of the first channel or the second channel of the wheel of the actuator is about 2:1 to about 1:5. In some embodiments, a ratio between the arc length of the shuttle guide 121C and a diameter of at least one of the first channel or the second channel of the wheel of the actuator is at least about 2:1. In some embodiments, a ratio between the arc length of the shuttle guide 121C and a diameter of at least one of the first channel or the second channel of the wheel of the actuator is at most about 1:5.

Per FIG. 8 the exemplary shuttle 123 further comprises a cable attachment 127 to connect to the cable 130. As shown, the cable attachment 127 comprises a cavity that receives and secures a portion of the cable 130. Alternatively, in some embodiments, the cable attachment 127 comprises a clamp, a hole, a screw, a bolt, a nut, a clip, a pin, or any combination thereof. In some embodiments, the cable attachment 127 comprises a terminal cable attachment, wherein the cable terminates at the cable attachment 127. In some embodiments, the cable attachment 127 comprises a non-terminal cable attachment, wherein the cable passes through and couples to the cable attachment 127. In some embodiments, the shuttle 123 comprises 1, 2, 3, 4, 5, 6, 7, 8, 9, 10 or more cable attachments 127. As seen, the exemplary shuttle 123 is rigidly connected to the cable 130 at the cable attachment 127 such that a tensile force on the cable 130 causes the shuttle 123 to translate in the direction of the tensile force.

In some embodiments, the shuttle 123 comprises a pawl 124, a cushion 126, or both. In some embodiments, the shuttle 123 comprises a cavity 123A that accepts the pawl 124, the cushion 126, or both. In some embodiments, the cavity 123A has an inner width greater than an outer width of the pawl 124, an outer width of the cushion 126, or both. In some embodiments, the cavity 123A has a depth that terminates within the shuttle 123. In some embodiments, the cavity 123A extends through the shuttle 123. In some embodiments, the cavity 123A has a cross-sectional shape comprising a square, a circle, a triangle, a hexagon, or any other polygon.

In some embodiments, the pawl 124 is biased towards engagement with the notch 122A of the arcuate needle 122. In some embodiments, the pawl 124 is biased towards the first direction 1000. In some embodiments, the pawl 124 comprises a pivot 127 to rotate about the shuttle 123. In some embodiments, the pivot 127 comprises a pin extrusion element of the pawl 124. In some embodiments, the pivot 127 comprises a pin that is rigidly attached to the pawl 124, and which rotates about a hole in the shuttle 123. In some embodiments, the pivot 127 comprises a pin that is rigidly attached to shuttle 123, and which rotates about a hole in the pawl 124. Alternatively, in some embodiments, the pivot 127 comprises a divot, a slot, a screw, or any combination thereof within the pawl 124, the shuttle 123, or both.

In some embodiments, the pawl 124 is biased towards engagement by the cushion 126. In some the cushion 126 is elastic. In some the cushion 126 comprises a spring. In some embodiments, the cushion 126 presses against the pawl 124 in a second direction opposite the first rotational direction 1000. In some embodiments, the cushion 126 presses against the pawl 124 to drive the pawl 124 upwards and out of the cavity 123A to engage with the notch 122A of the arcuate needle 122. In some embodiments, a position of the pivot 127 relative to the termination of the cavity 123A, in combination with a position of the cushion 126 enables the pawl to be engagement bias. In some embodiments, when the pawl 124 is engaged, the cushion 126 presses the pawl 124 against the termination of the cavity 123A of the shuttle 123. In some embodiments, when the pawl 124 is disengaged, the arcuate needle 122 presses the pawl 124 against the cushion 126 such that the pawl moves upward into the cavity 123A and away from termination of the cavity 123A of the shuttle 123. In some embodiments, an upper face of the pawl 124 is slanted towards one end of the shuttle 123. In some embodiments, an upper face of the pawl 124 is slanted upwards in a second rotational direction opposite the first rotational direction 1000. In some embodiments, an upper face of the pawl 124 is slanted to engage with the ramp of the arcuate needle. In some embodiments, the pawl 124 further comprises a spring, a flexure, a dual spring gate, a cushion, a piston, a rod, a pin, a tooth, or any combination thereof. In some embodiments, the first distal assembly 120 comprises 1, 2, 3, 4, 5, 6, 7, 8, 9, 10 or more pawls 124.

In some embodiments, the cushion 126 is integrated into the pawl 124. In some embodiments, the cushion 126 is integrated into the shuttle 123. In some embodiments, the cushion 126 is integrated into the cavity 123A of the shuttle 123. In some embodiments, the shuttle 123 does not comprise a cushion 126. In some embodiments, the shuttle 123 does not comprise a cushion 126, wherein the pawl 124 comprises a flexure, a spring, a dual spring gate, a cushion, a piston, a rod, a pin, a tooth, or any combination thereof to bias the pawl 124 against the arcuate needle. In some embodiments, the shuttle 123 does not comprise a pawl 124 or a cushion 126, wherein the shuttle 123 comprises a flexure, a spring, a dual spring gate, a cushion, a piston, a rod, a pin, a tooth, or any combination thereof to engage and disengage with the arcuate needle.

Further, per FIG. 7, the exemplary first housing 121 comprises a cable pulley 121D that guides the cable 130 from the proximal assembly, through the shuttle guide 121C, to the shuttle 123 and out the first housing 121. In some embodiments, at least one of the primary first housing portion 601, the secondary first housing portion 602, or the pin fastener 603 of the first housing 121 comprises the cable pulley 121D. In some embodiments, the first housing 121 comprises 1, 2, 3, 4, 5, 6, 7, 8, 9, 10 or more cable pulleys 121D. In some embodiments, the cable pulley 121D comprises a bearing, a rod, a curved surface, or any combination thereof. In some embodiments, the cable pulley 121D comprises a rigid portion of the first housing 121. Alternatively, in some embodiments, the cable pulley 121D rotates within the first housing 121. Alternatively, in some embodiments, the cable pulley 121D rotates within the primary first housing portion 601, the secondary first housing portion 602, or both. In some embodiments, at least one of the primary first housing portion 601 or the secondary first housing portion 602 further comprise one or more cable guides that direct the cable 130 towards and away from the cable pulley 121D.

FIGS. 10-13 show the progression of the arcuate needle 122 as it is translated by the shuttle 123 and the pawl 124 through the arcuate needle guide 121B. Per FIG. 10, in a first position, the arcuate needle 122 is completely housed within the arcuate needle guide 121B within the first housing 121. As the cable 130 pulls the shuttle 123 within the shuttle guide 121C in a first rotational direction 1000 with respect to the first housing 121, the pawl 124 engages with a notch 122A in the arcuate needle 122, per FIG. 11, causing a portion of the arcuate needle 123 to exit the first housing 121. Once the shuttle 123 cannot move any further within the shuttle guide 121C of the first housing 121 in the first rotational direction 1000, the cable 130 then pulls the shuttle 123 in a second rotational direction opposite the first rotational direction 1000 such that the pawl 124 engages with a suture end 1201 of the arcuate needle 122. The cable 130 is then pulled in the first rotational direction 1000 such that the shuttle 123 translates in the first rotational direction 1000, while the pawl 124 pushes against the suture end 1201 of the arcuate needle 122 to translate the arcuate needle 122, per FIG. 12, such that majority of the arcuate needle 122 exits the first housing 121 and only a portion of a pointed end 1101 and a suture end 1201 of the arcuate needle 122 are within the first housing 121. After the shuttle 123 cannot move any further within the shuttle guide 121C of the first housing 121 in the first rotational direction 1000, the cable 130 pulls the shuttle 123 through the shuttle guide 121C of the first housing 121 in the second rotational direction, per FIG. 13, such that the pawl 124 reengages with the notch 122A in the arcuate needle 122. The cable then 130 pulls the shuttle 123 in the second rotational direction within the shuttle guide 121C of the first housing 121 to translate the arcuate needle 122 in the first rotational direction 1000 and back within the first housing 121 to perform one suture.

As such, a single suturing maneuver comprises, pulling the cable 130 in the first direction 1000, pulling the cable 130 in a second direction opposite the first direction 1000, pulling the cable 130 in the first direction 1000 a second time, pulling the cable 130 in the second direction a second time, pulling the cable 130 in the first direction 1000 a third time, and pulling the cable 130 in the second direction a third time. As shown, the first rotational direction 1000 is counterclockwise with respect to the first housing 121. Alternatively, in some embodiments, the first rotational direction 1000 is clockwise with respect to the first housing 121.

Figure 10:
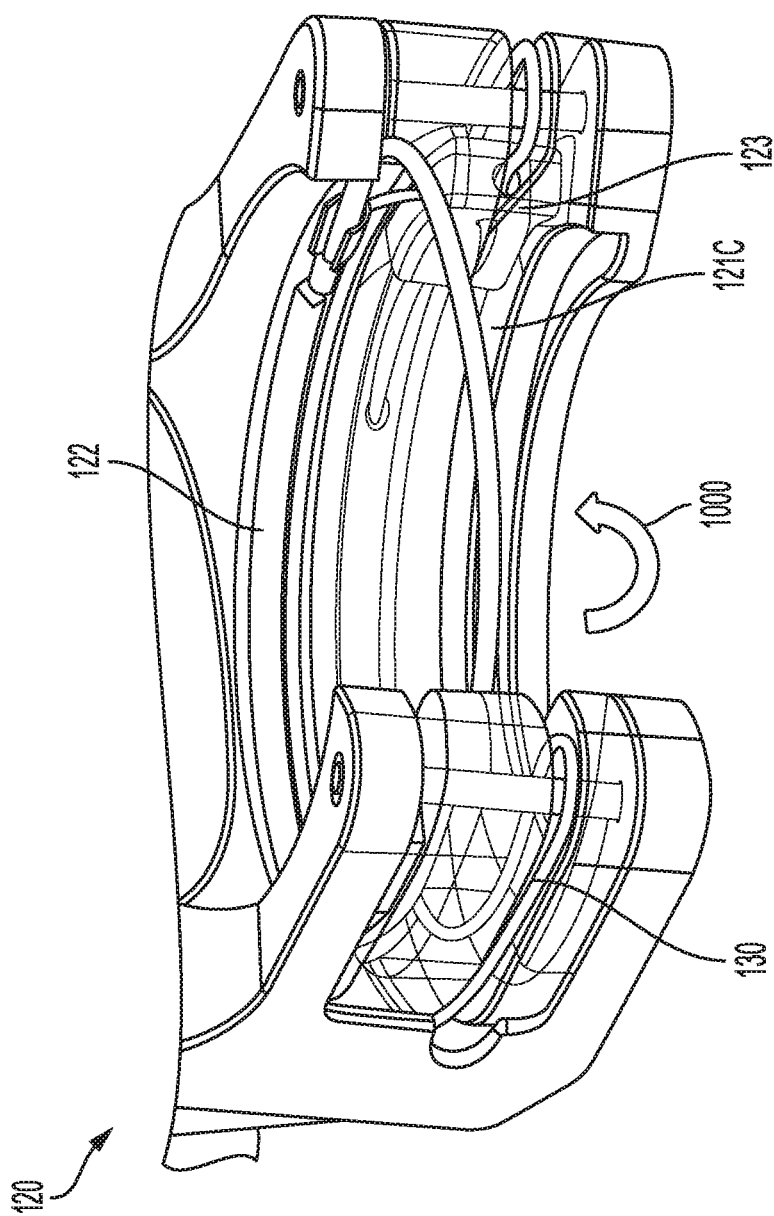
FIG. 10 is a detailed illustration of the exemplary first distal assembly in a fourth position with a portion of the shuttle guide opaque, per an embodiment herein.
Figure 11:
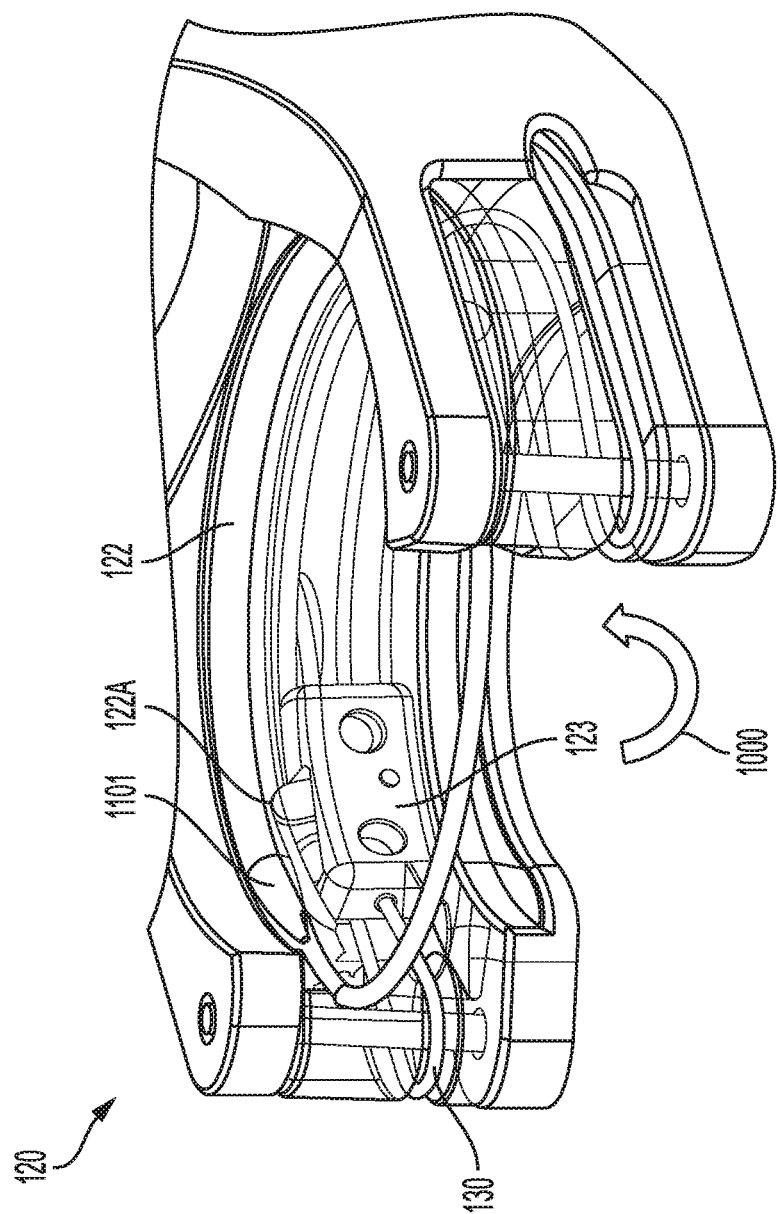
FIG. 11 is a detailed illustration of the exemplary first distal assembly in a fifth position with a portion of the shuttle guide opaque, per an embodiment herein.
Figure 12:
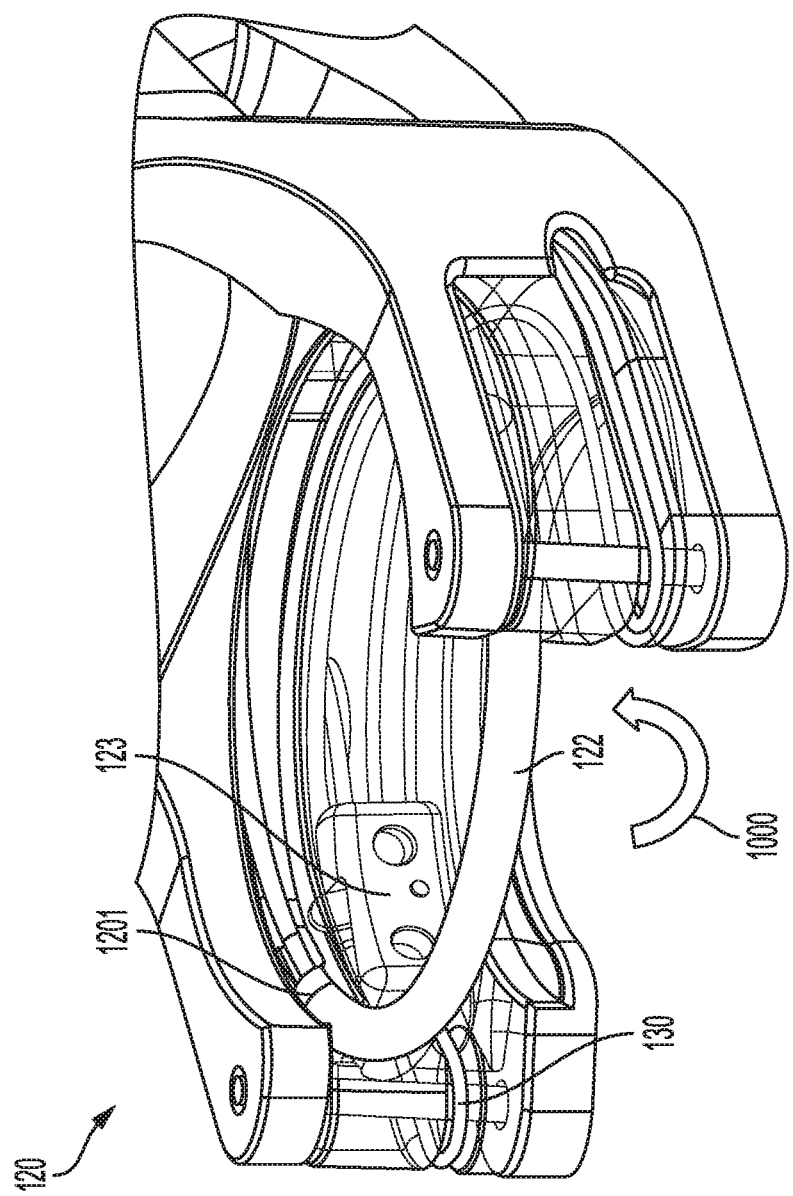
FIG. 12 is a detailed illustration of the exemplary first distal assembly in a sixth position with a portion of the shuttle guide opaque, per an embodiment herein.
Figure 13:
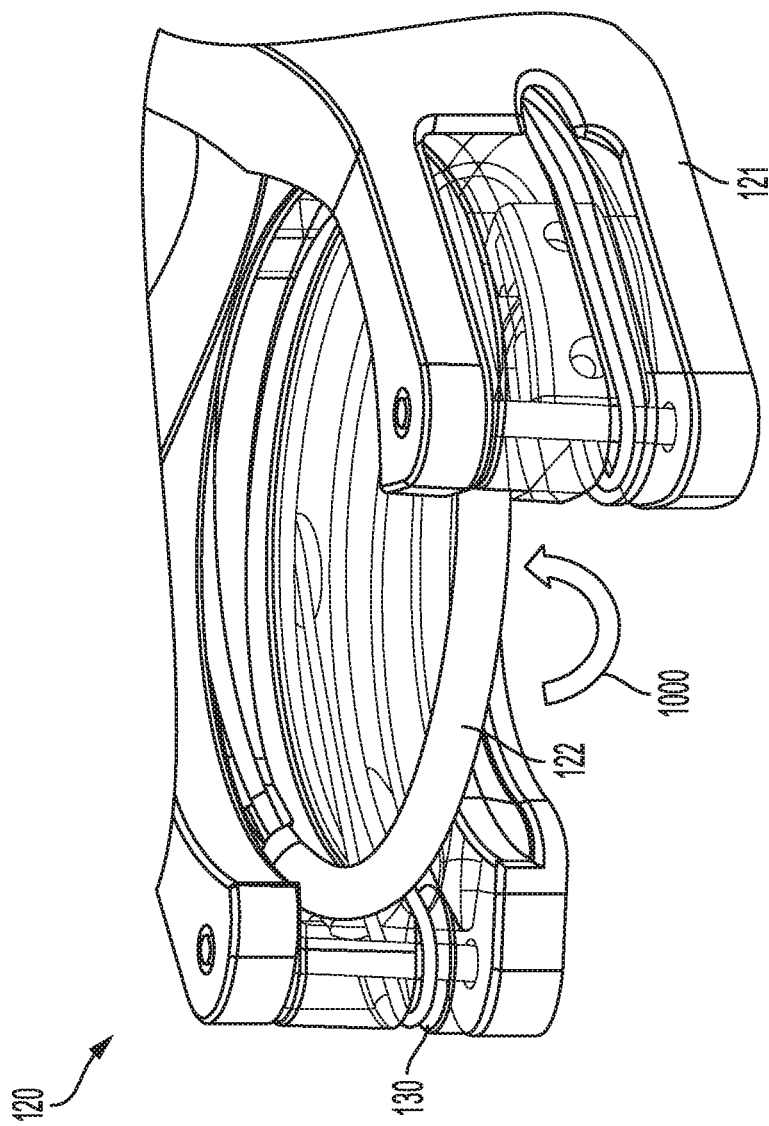
FIG. 13 is a detailed illustration of the exemplary first distal assembly in a seventh position with a portion of the shuttle guide opaque, per an embodiment herein.
Figure 14:
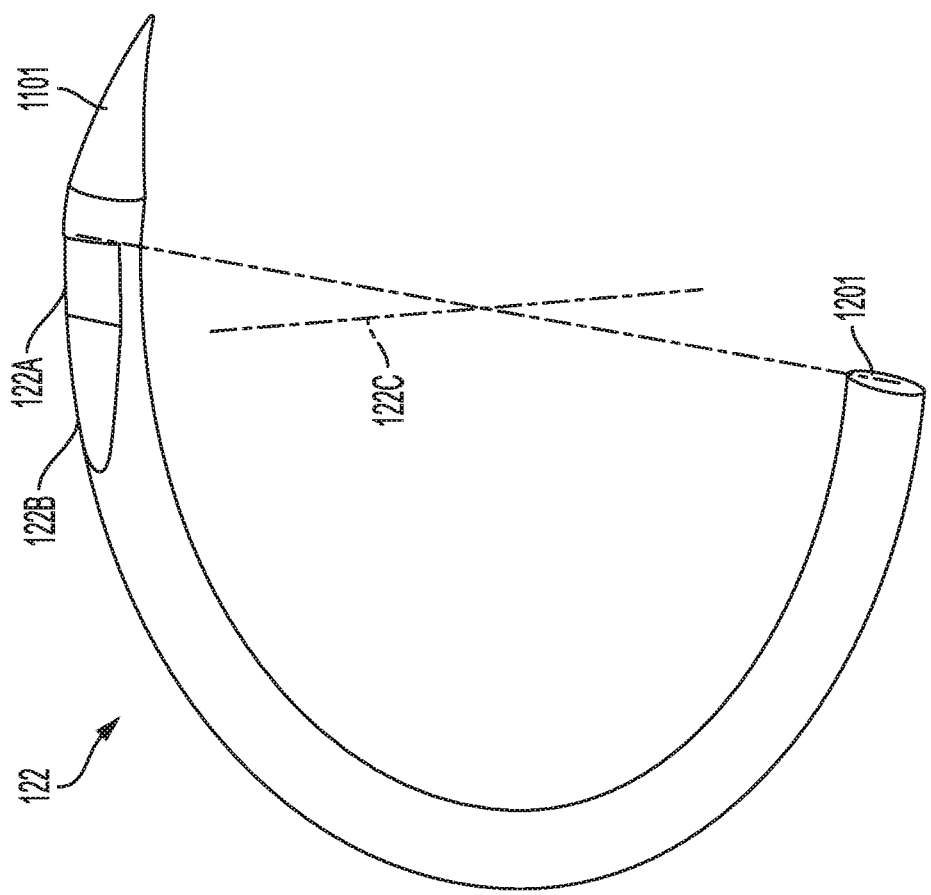
FIG. 14 is an illustration of an exemplary arcuate needle, per an embodiment herein.

In some embodiments, per FIGS. 3, 4 and 10, pulling the cable 130 in the first rotational direction 1000 comprises pulling the primary cable portion 132 towards the second housing 111 of the proximal assembly 110. In some embodiments, pulling the cable 130 in the first rotational direction 1000 comprises rotating the wheel 113 of the actuator 112 in the secondary direction opposite the primary direction 131. In some embodiments, pulling the cable 130 in the second rotational direction opposite the first rotational direction 1000 comprises pulling the secondary cable portion 133 towards the second housing 111 of the proximal assembly 110 In some embodiments, pulling the cable 130 in the second rotational direction opposite the first rotational direction 1000 comprises rotating the wheel 113 of the actuator 112 in the primary direction 131. In some embodiments, translating the shuttle 123 in the first rotational direction 1000 comprises pulling the primary cable portion 132 towards the second housing 111 of the proximal assembly 110. In some embodiments, translating the shuttle 123 in the first rotational direction 1000 comprises rotating the wheel 113 of the actuator 112 in the secondary direction opposite the primary direction 131. In some embodiments, translating the shuttle 123 in the second rotational direction opposite the first rotational direction 1000 comprises pulling the secondary cable portion 133 towards the second housing 111 of the proximal assembly 110. In some embodiments, translating the shuttle 123 in the second rotational direction opposite the first rotational direction 1000 comprises rotating the wheel 113 of the actuator 112 in the primary direction 131.

In some embodiments, when pulled by the cable 130 in the first direction 1000 or the second direction, the shuttle 123 translates about one or more degrees of rotation within the shuttle guide 121C. In some embodiments, when pulled by the cable 130 in the first direction 1000 or the second direction, the shuttle 123 translates about one degree of rotation within a 270 degree arc within the shuttle guide 121C. In some embodiments, when pulled by the cable 130 in the first direction 1000 or the second direction, the shuttle 123 translates about one degree of rotation within a 90, 100, 110, 120, 140, 160, 180, 200, 220, 240, 260, 280, 300, 320 or greater degree arc within the shuttle guide 121C, including increments therein.

In some embodiments, at least one of the first housing 111, the arcuate needle 112, the shuttle 123, the pawl 124, the suture 125, the cushion 126, the primary first housing portion 601, the secondary first housing portion 602, or the pin fastener 603, are composed of plastic, metal, fiberglass, carbon fiber, wood, or any combination thereof.

Arcuate Needle and Suture

FIGS. 14-18 show illustrations of exemplary arcuate needles 122 and sutures 125. Per FIGS. 14 and 15, in some embodiments, the arcuate needle 122 has a notch 122A, a pointed end 1101, and a suture end 1201. In some embodiments, the notch 122A is ramped in a direction opposite the first rotational direction. Alternatively, in some embodiments, the notch 122A is ramped in the first rotational direction. In some embodiments, the notch 122A is ramped at an angle of about 5, 10, 15, 20, 25, 30, 35, 40, 45, 50, 55, 60, 65 or more degrees, including increments therein. In some embodiments, the notch 122A is ramped at an angle of at least about 5 degrees. As shown, an angle between the notch 122A and the suture end 1201 of the exemplary arcuate needle 122 is about 180 degrees. Alternatively, in some embodiments, the angle between the notch 122A and the suture end 1201 of the exemplary arcuate needle 122 is about 90, 100, 120, 140, 160, 180, 200, 220, 240, 260, 2800 degrees or more, including increments therein. In some embodiments, the angle between the notch 122A and the suture end 1201 of the exemplary arcuate needle 122 is at least about 90 degrees.

In some embodiments, an outer diameter of the arcuate needle 122 is about 7 mm to about 20 mm. In some embodiments, an outer diameter of the arcuate needle 122 is at least about 7 mm. In some embodiments, an outer diameter of the arcuate needle 122 is at most about 20 mm. In some embodiments, a thickness 1510 of the arcuate needle 122 is about 0.5 mm to about 2 mm. In some embodiments, a thickness 1510 of the arcuate needle 122 is at least about 0.5 mm. In some embodiments, a thickness 1510 of the arcuate needle 122 is at most about 2 mm. In some embodiments, a ratio between an outer diameter and a thickness 1510 of the arcuate needle 122 is about 3:1 to about 15:1. In some embodiments, a ratio between an outer diameter and a thickness 1510 of the arcuate needle 122 is at least about 3:1. In some embodiments, a ratio between an outer diameter and a thickness 1510 of the arcuate needle 122 is at most about 15:1. In some embodiments, a ratio between an outer diameter and the thickness 1510 of the arcuate needle 122 is about 3:1, 4:1, 5:1, 6:1, 7:1, 8:1, 9:1, 10:1, 11:1, 12:1, 13:1, 14:1, or 15:1. In some embodiments, a ratio between an outer diameter and the thickness 1510 of the arcuate needle 122 is at least about 3:1. In some embodiments, the outer diameter of the arcuate needle 122 is measured as a maximum distance between two points on the surface of the arcuate needle 122. In some embodiments, the outer diameter of the arcuate needle 122 is measured as a maximum outer diameter of the arcuate needle 122. In some embodiments, the width of the arcuate needle 122 is measured as a thickness 1510 of the arcuate needle 122. In some embodiments, the thickness 1510 of the arcuate needle 122 is measured as a thickness 1510 of the arcuate needle 122 that is not within the pointed end 1101, the suture end 1201, or the notch 122A. In some embodiments, the thickness 1510 of the arcuate needle 122 is measured as a maximum, a minimum, or an average thickness 1510 of the arcuate needle 122.

In some embodiments, the pointed end 1101 is pointed at an angle of about 5, 10, 15, 20, 25, 30, 35, 40, 45 degrees or greater, including increments therein. In some embodiments, the pointed end 1101 is pointed at an angle of at least about 5 degrees. As shown, the exemplary suture end 120 is flat. Alternatively, in some embodiments, the suture end 120 is rounded, tapered, or angled.

As shown, in some embodiments, the arcuate needle 122 has two notches 122A. In some embodiments, the arcuate needle 122 has 2, 3, 4, 5, 6, 7, 8, 9, 10 or more notches 122A. In some embodiments, the arcuate needle 122 has two or more notches 122A. As shown, each notch 122A is spaced about the arcuate needle 122 at an angle of about 180 degrees.

In some embodiments, the notches 122A are spaced about the arcuate needle 122 at an angle of about 10 degrees to about 180 degrees. In some embodiments, the notches 122A are spaced about the arcuate needle 122 at an angle of about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 80 degrees, about 10 degrees to about 100 degrees, about 10 degrees to about 120 degrees, about 10 degrees to about 140 degrees, about 10 degrees to about 160 degrees, about 10 degrees to about 180 degrees, about 20 degrees to about 30 degrees, about 20 degrees to about 40 degrees, about 20 degrees to about 50 degrees, about 20 degrees to about 60 degrees, about 20 degrees to about 80 degrees, about 20 degrees to about 100 degrees, about 20 degrees to about 120 degrees, about 20 degrees to about 140 degrees, about 20 degrees to about 160 degrees, about 20 degrees to about 180 degrees, about 30 degrees to about 40 degrees, about 30 degrees to about 50 degrees, about 30 degrees to about 60 degrees, about 30 degrees to about 80 degrees, about 30 degrees to about 100 degrees, about 30 degrees to about 120 degrees, about 30 degrees to about 140 degrees, about 30 degrees to about 160 degrees, about 30 degrees to about 180 degrees, about 40 degrees to about 50 degrees, about 40 degrees to about 60 degrees, about 40 degrees to about 80 degrees, about 40 degrees to about 100 degrees, about 40 degrees to about 120 degrees, about 40 degrees to about 140 degrees, about 40 degrees to about 160 degrees, about 40 degrees to about 180 degrees, about 50 degrees to about 60 degrees, about 50 degrees to about 80 degrees, about 50 degrees to about 100 degrees, about 50 degrees to about 120 degrees, about 50 degrees to about 140 degrees, about 50 degrees to about 160 degrees, about 50 degrees to about 180 degrees, about 60 degrees to about 80 degrees, about 60 degrees to about 100 degrees, about 60 degrees to about 120 degrees, about 60 degrees to about 140 degrees, about 60 degrees to about 160 degrees, about 60 degrees to about 180 degrees, about 80 degrees to about 100 degrees, about 80 degrees to about 120 degrees, about 80 degrees to about 140 degrees, about 80 degrees to about 160 degrees, about 80 degrees to about 180 degrees, about 100 degrees to about 120 degrees, about 100 degrees to about 140 degrees, about 100 degrees to about 160 degrees, about 100 degrees to about 180 degrees, about 120 degrees to about 140 degrees, about 120 degrees to about 160 degrees, about 120 degrees to about 180 degrees, about 140 degrees to about 160 degrees, about 140 degrees to about 180 degrees, or about 160 degrees to about 180 degrees. In some embodiments, the notches 122A are spaced about the arcuate needle 122 at an angle of about 10 degrees, about 20 degrees, about 30 degrees, about 40 degrees, about 50 degrees, about 60 degrees, about 80 degrees, about 100 degrees, about 120 degrees, about 140 degrees, about 160 degrees, or about 180 degrees. In some embodiments, the notches 122A are spaced about the arcuate needle 122 at an angle of at least about 10 degrees, about 20 degrees, about 30 degrees, about 40 degrees, about 50 degrees, about 60 degrees, about 80 degrees, about 100 degrees, about 120 degrees, about 140 degrees, or about 160 degrees. In some embodiments, the notches 122A are spaced about the arcuate needle 122 at an angle of at most about 20 degrees, about 30 degrees, about 40 degrees, about 50 degrees, about 60 degrees, about 80 degrees, about 100 degrees, about 120 degrees, about 140 degrees, about 160 degrees, or about 180 degrees.

Figure 15:
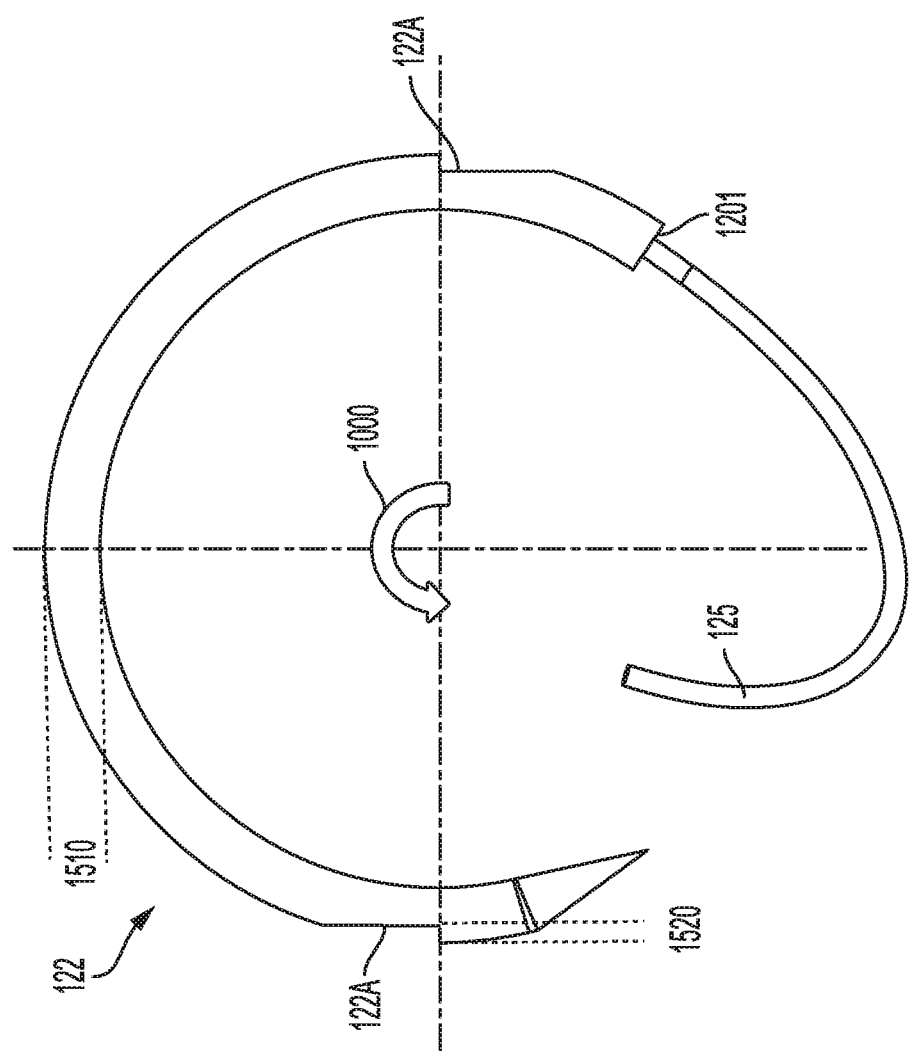
FIG. 15 is an illustration of an exemplary arcuate needle having 2 notches, per an embodiment herein.

In some embodiments, per FIG. 15, a ratio between the thickness 1510 of the arcuate needle 122 and the depth 1520 of the notch 122A is about 2:1 to about 15:1. In some embodiments, a ratio between the thickness 1510 of the arcuate needle 122 and the depth 1520 of the notch 122A is at least about 2:1. In some embodiments, a ratio between the thickness 1510 of the arcuate needle 122 and the depth 1520 of the notch 122A is at most about 15:1. As shown, in some embodiments, the depth 1520 of the notch 122 is measured as a maximum normal distance between a surface of the notch and an outer surface of the arcuate needle 122.

Figure 16:
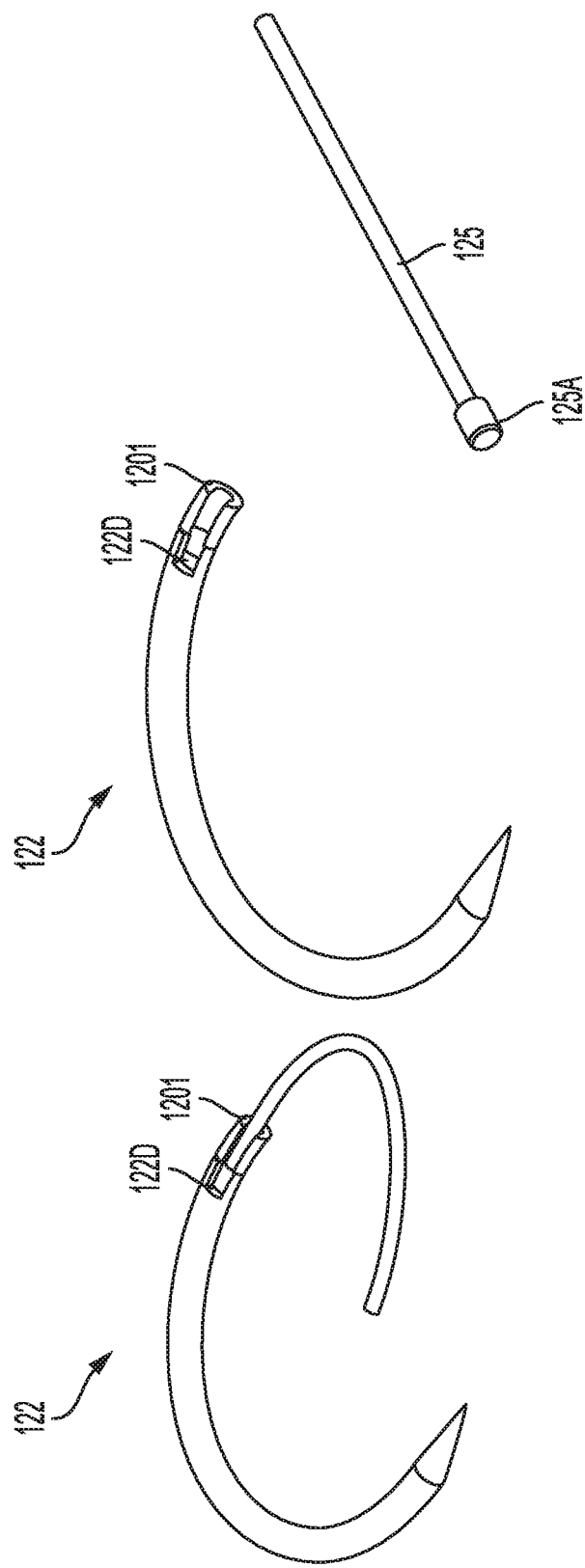
FIG. 16 is an illustration of an exemplary arcuate needle and suture, per an embodiment herein.

In some embodiments, per FIG. 16, the suture end 1201 of the arcuate needle 122 comprises a primary suture attachment 122D that couples the suture 125 to the arcuate needle 122. Further, in some embodiments, the suture 125 comprises a secondary suture attachment 125A that mates with the primary suture attachment 122D. In some embodiments, the primary suture attachment 122D and the secondary suture attachment 125A removably mate. In some embodiments, the primary suture attachment 122D and the secondary suture attachment 125A removably mate such that the suture 125 does not disconnect from the arcuate needle 122 during suturing. In some embodiments, the primary suture attachment 122D and the secondary suture attachment 125A removably connect and/or disconnect in-situ.

As shown the exemplary primary suture attachment 122D comprises an open channel having a first channel portion and a second channel portion, wherein the first channel portion breaches the suture end 1201 of the arcuate needle 122, and wherein the second channel portion is further from the suture end 1201 than the proximal width. As seen, a width of the second channel portion is greater than a width of the first channel portion. In some embodiments, a ratio between the width of the first channel portion and the width of the second channel portion is about 1.1:1 to about 3:1. In some embodiments a ratio between the width of the first channel portion and the width of the second channel portion is at least about 1.1:1. In some embodiments, the proximal width partially encases the suture. In some embodiments, the first channel portion partially encases the secondary suture attachment 125A. In some embodiments, the first channel portion is equal to or greater than a width of the suture 125.

In some embodiments, a center plane of the first channel portion and a center plane of the second channel portion are coplanar. In some embodiments, at least one of the first channel portion or a second channel portion comprises a rounded channel. In some embodiments, a centerpoint of the rounded surface of the first channel portion, a centerpoint of the rounded surface of the rounded second channel portion, or both are aligned with a center arcuate axis of the arcuate needle 122.

As shown the secondary suture attachment 125A comprises a knot or bulb. In some embodiments, a thickness of the suture 125 is less than a thickness of the suture attachment 125A. In some embodiments, a ratio between the thickness of the suture 125 and the thickness of the suture attachment 125A is about 1:1.1 to about 1:3.

Alternatively, exemplary at least one of the primary suture attachment 122D or the secondary suture attachment 125A comprises a tie, a string, a band, a hook and loop fastener, a tape, a strap, a magnet, a cinch, a press fit, a set screw, an adhesive, or any combination thereof.

Figure 17:
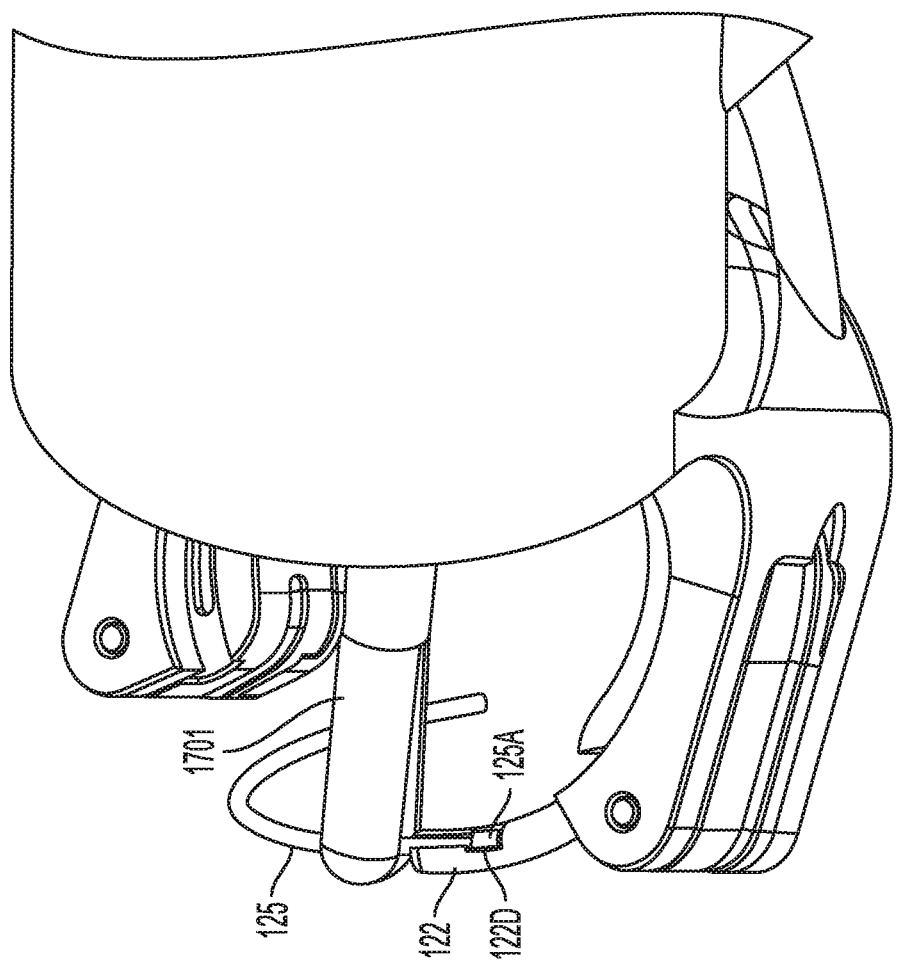
FIG. 17 is the exemplary first illustration of in-situ suture replacement by the exemplary first distal assembly, per an embodiment herein.
Figure 18:
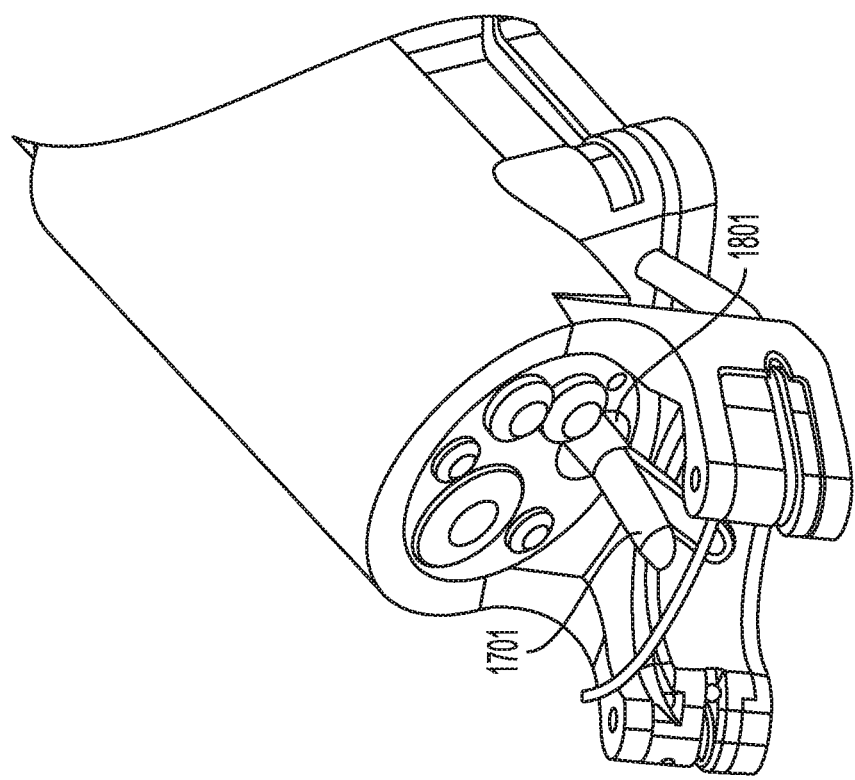
FIG. 18 is a second exemplary illustration of in-situ suture replacement by the exemplary first distal assembly, per an embodiment herein.
Figure 21:
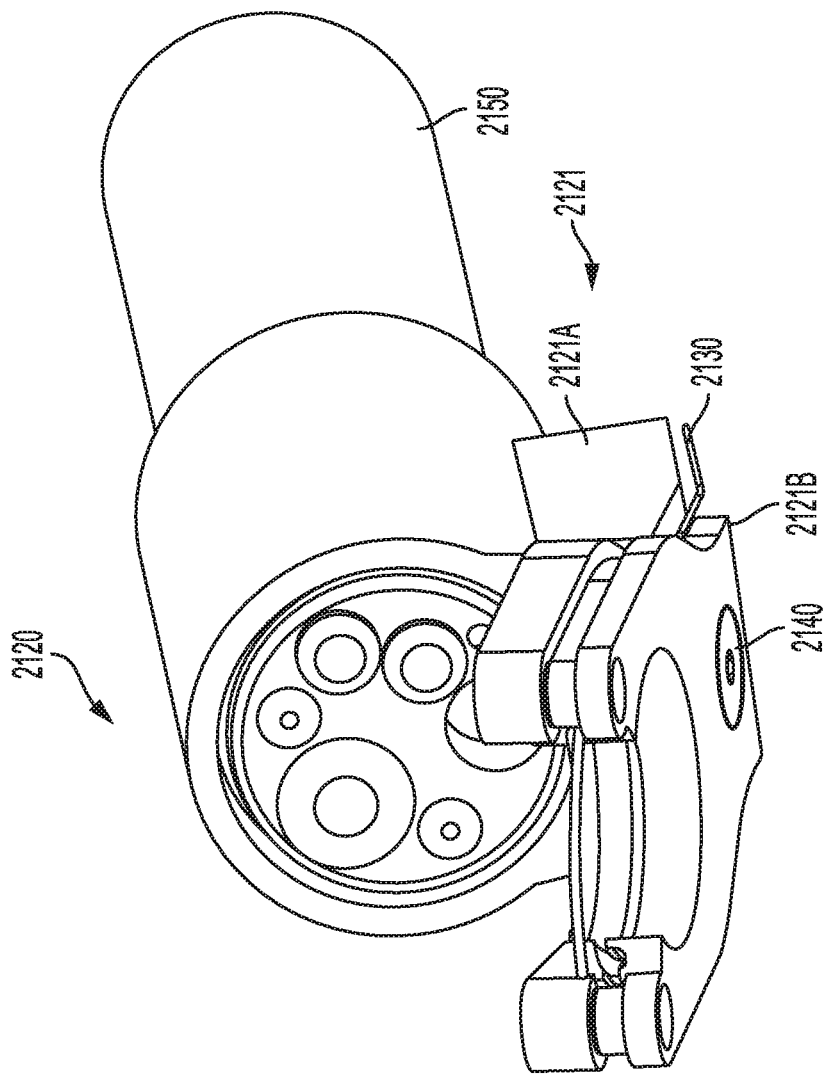
FIG. 21 is a second illustration of the exemplary second proximal assembly coupled to an endoscope, per an embodiment herein.
Figure 22:
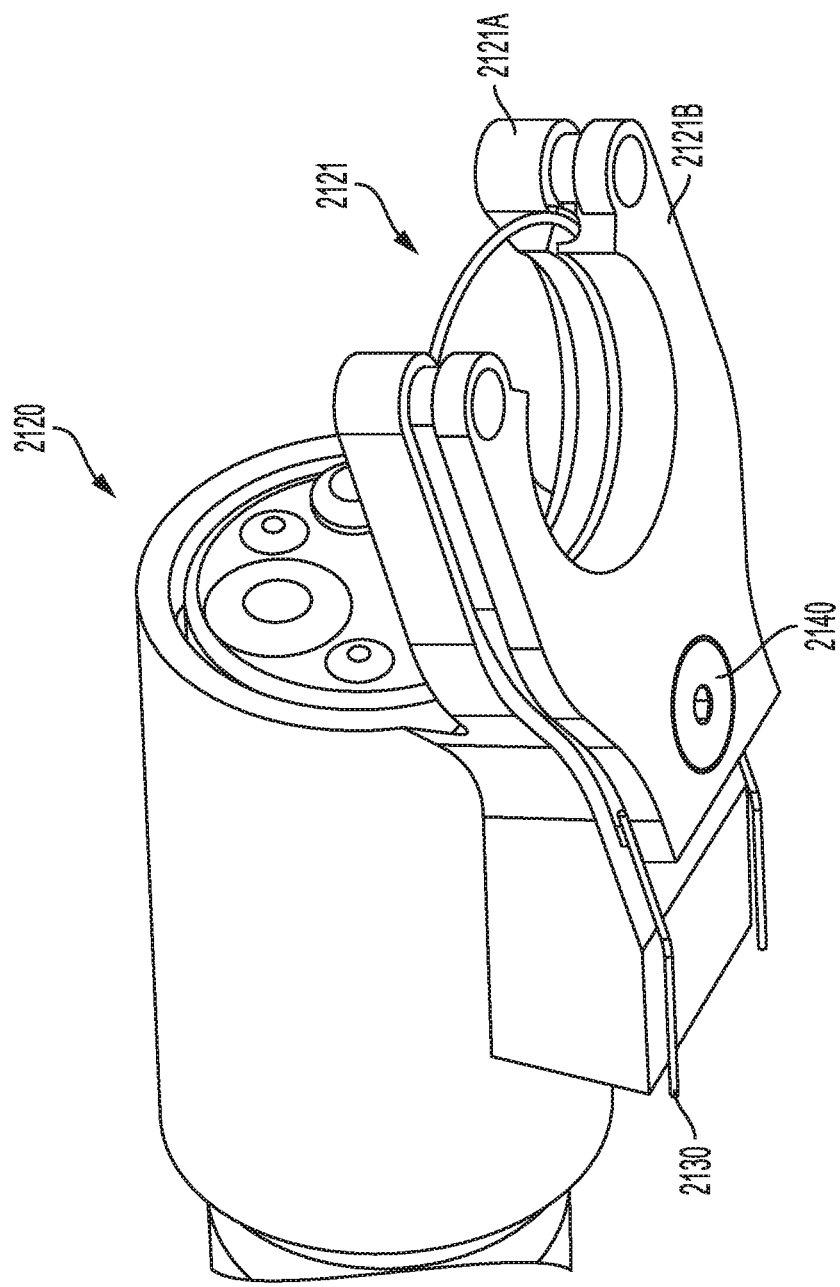
FIG. 22 is a third illustration of the exemplary second proximal assembly coupled to an endoscope, per an embodiment herein.

Per FIGS. 17 and 18, the primary suture attachment 122D within the arcuate needle 122, and the secondary suture attachment 125A of the exemplary suture 125 couple, decouple, or both in-vitro by a pincer 1701 employed in a working channel 1801 of the endoscope. Such a feature enables quick and easy suture 125 exchanges during procedures requiring suturing at more than one location. As shown, the secondary suture attachment 125A is located on an inner surface of the arcuate needle 122 to allow the pincer 1701 to connect and disconnect the suture 125 to the arcuate needle 122.

Shuttle Assembly

FIG. 19A shows an exemplary illustration of the shuttle 123 where the pawl 124 is engaged. FIG. 19B is an exemplary illustration of a shuttle 123 where the pawl 124 is disengaged. Further, as shown the pawl 124 rotates within the shuttle 123 about a pivot 129. In some embodiments, the pawl 124 comprises a spring, a flexure, a dual spring gate, a cushion, a piston, a rod, a pin, a tooth, or any combination thereof. In some embodiments, the first distal assembly 120 comprises 1, 2, 3, 4, 5, 6, 7, 8, 9, 10 or more pawls 124. In some embodiments, the shuttle slides within the shuttle guide of the distal assembly. As seen, the shuttle 123 is arcuate to slide within the shuttle guide.

In some embodiments, the shuttle 123 comprises a pawl 124, a cushion 126, or both. In some embodiments, the pawl 124 rotates about a pivot 127 in the shuttle 123. In some embodiments, the shuttle 123 comprises a cavity that accepts the pawl 124. In some embodiments, the pawl 124 is biased towards engagement. In some embodiments, the pawl 124 is biased towards engagement by a cushion 126. In some embodiments, the cushion 126 presses against the pawl 124 to drive the pawl 124 upwards to engage with the notch 122A of the arcuate needle 122. In some embodiments, a position of the pivot 127 relative to the termination of the cavity 123A, in combination with the cushion 126, enables the pawl to be engagement bias. In some embodiments, when the pawl 124 is engaged, the cushion 126 presses the pawl 124 against the termination of the cavity 123A of the shuttle 123. In some embodiments, when the pawl 124 is disengaged, the arcuate needle 122 presses the pawl 124 against the cushion 126 and away from termination of the cavity 123A of the shuttle 123. In some embodiments, an upper face of the pawl 124 is slanted towards one end of the shuttle 123. In some embodiments, an upper face of the pawl 124 is slanted to engage with the ramp of the arcuate needle.

In some embodiments, the cushion 126 is integrated into the pawl 124. In some embodiments, the cushion 126 is integrated into the shuttle 123. In some embodiments, the shuttle 123 does not comprise a cushion 126. In some embodiments, the shuttle 123 does not comprise a cushion 126, wherein the pawl 124 comprises a flexure, a spring, a dual spring gate, a cushion, a piston, a rod, a pin, a tooth, or any combination thereof to bias the pawl 124. In some embodiments, the shuttle 123 does not comprise a pawl 124 or a cushion 126, wherein the shuttle 123 comprises a flexure, a spring, a dual spring gate, a cushion, a piston, a rod, a pin, a tooth, or any combination thereof to engage and disengage with the arcuate needle.

In some embodiments, the exemplary shuttle 123 further comprises a cable attachment 127 to connect to the cable. In some embodiments, the cable attachment 127 comprises a clamp, a hole, a screw, a bolt, a nut, a clip, a pin, or any combination thereof. In some embodiments, the cable attachment 127 comprises a terminal cable attachment, wherein the cable terminates at the cable attachment 127. In some embodiments, the cable attachment 127 comprises a non-terminal cable attachment, wherein the cable passes through and couples to the cable attachment 127. In some embodiments, the shuttle 123 comprises 1, 2, 3, 4, 5, 6, 7, 8, 9, 10 or more cable attachments 127. In some embodiments, the shuttle 123 slides within the shuttle guide of the distal assembly. As seen, the shuttle 123 is arcuate to slide within the shuttle guide.

Second Distal Assembly

FIGS. 20-30B show illustrations of an exemplary second proximal assembly 2120 and a cable 2130 having a pawl 2124. In some embodiments, the second proximal assembly 2120 comprises an arcuate needle 2122 having a notch 2122A and a first housing 2121 comprising a primary housing portion 2121A and a secondary housing portion 2121B. In some embodiments, the cable 2130 comprises a sheath surrounding at least a portion of the cable 2130.

As seen in FIGS. 21-25 and 28, the primary housing portion 2121A and the secondary housing portion 2121B are connected by a housing fastener 2140. In some embodiments, the primary housing portion 2121A and the secondary housing portion 2121B are connected by 1, 2, 3, 4, 5, 6, 7, 8, 9, 10, or more housing fasteners 2140. As shown the housing fastener 2140 comprises a screw which passes through a clearance hole within the secondary housing portion 2121B and fastens to a threaded feature 2140A within the primary housing portion 2121A. Alternatively, in some embodiments, the housing fastener 2140 comprises a bolt, a rivet, a nut, a weld, an adhesive, or any combination thereof within at least one of the primary housing portion 2121A or the secondary housing portion 2121B. In some embodiments, the first housing 2121 does not comprise the primary housing portion 2121A or the secondary housing portion 2121B. In some embodiments, the first housing 2121 further comprises a tertiary housing portion or more housing portions. In some embodiments, at least one of the primary housing portion 2121A or the secondary housing portion 2121B comprises one or more cable guides that direct the cable 2130 towards and away from the first housing 2121. In some embodiments, the primary housing portion 2121A and the secondary housing portion 2121B are made of the same material. In some embodiments, the primary housing portion 2121A and the secondary housing portion 2121B are made of different materials.

In some embodiments, at least one of the primary housing portion 2121A or the secondary housing portion 2121B comprises an endoscope fastener 2401 that couples the second proximal assembly 2120 to an endoscope 2150. In some embodiments, the endoscope fastener 2401 removably couples the first housing 121 to the endoscope 2150. As shown, the endoscope fastener 2401 comprises a press fit fastener. In some embodiments, the press fit endoscope fastener 2401 couples to the endoscope 2150 by firmly pressing the press fit endoscope fastener 2401 onto a distal end of the endoscope 2150. In some embodiments, the press fit endoscope fastener 2401 couples to the endoscope 2150 by firmly pressing and rotating the press fit endoscope fastener 2401 onto a distal end of the endoscope 2150. In some embodiments, the press fit endoscope fastener 2401 detaches from the endoscope 2150 by firmly pulling the press fit endoscope fastener 2401 off the distal end of the endoscope 2150. In some embodiments, the press fit endoscope fastener 2401 detaches from the endoscope 2150 by firmly pulling and twisting the press fit endoscope fastener 2401 off the distal end of the endoscope 2150.

As shown, in some embodiments, the endoscope fastener 2401 is rounded. In some embodiments, the endoscope 2150 has a proximal outer diameter of about 5 mm to about 16 mm. As such, in some embodiments, the endoscope fastener 2401 has an inner diameter of about 5 mm to about 16 mm. In some embodiments, the endoscope fastener 2401 has an inner diameter of at least about 5 mm. In some embodiments, the endoscope fastener 2401 has an inner diameter of at most about 16 mm. In some embodiments, the press fit endoscope fastener 2401 has a diameter equal to or lesser than the diameter of the endoscope 2150. In some embodiments, the endoscope fastener 2401 has a diameter equal to or greater than the diameter of the endoscope 2150. In some embodiments, the endoscope fastener 2401 is tapered and has a first inner diameter and a second inner diameter, wherein the first inner diameter is distal to the second inner diameter. In some embodiments, the first inner diameter is greater than the second inner diameter. In some embodiments, the second inner diameter is greater than the first inner diameter. In some embodiments, the diameter of the endoscope fastener 2401 is measured as a maximum, a minimum, or an average interior width. In some embodiments, the diameter of the endoscope 2150 is measured as a maximum, a minimum, or an average exterior width. Alternatively, in some embodiments, the endoscope fastener 2401 has a cross sectional shape comprising a triangle, a square, a hexagon, or any other polygon. Alternatively, in some embodiments, the endoscope fastener 2401 comprises a clamp, an adhesive, a tape, a strap, a set screw, a hook and loop fastener, a magnet, or any combination thereof. In some embodiments, the first distal assembly 120 comprises 1, 2, 3, 4, 5, 6, 7, 8, 9, 10, or more endoscope fasteners 2401.

Figure 28:
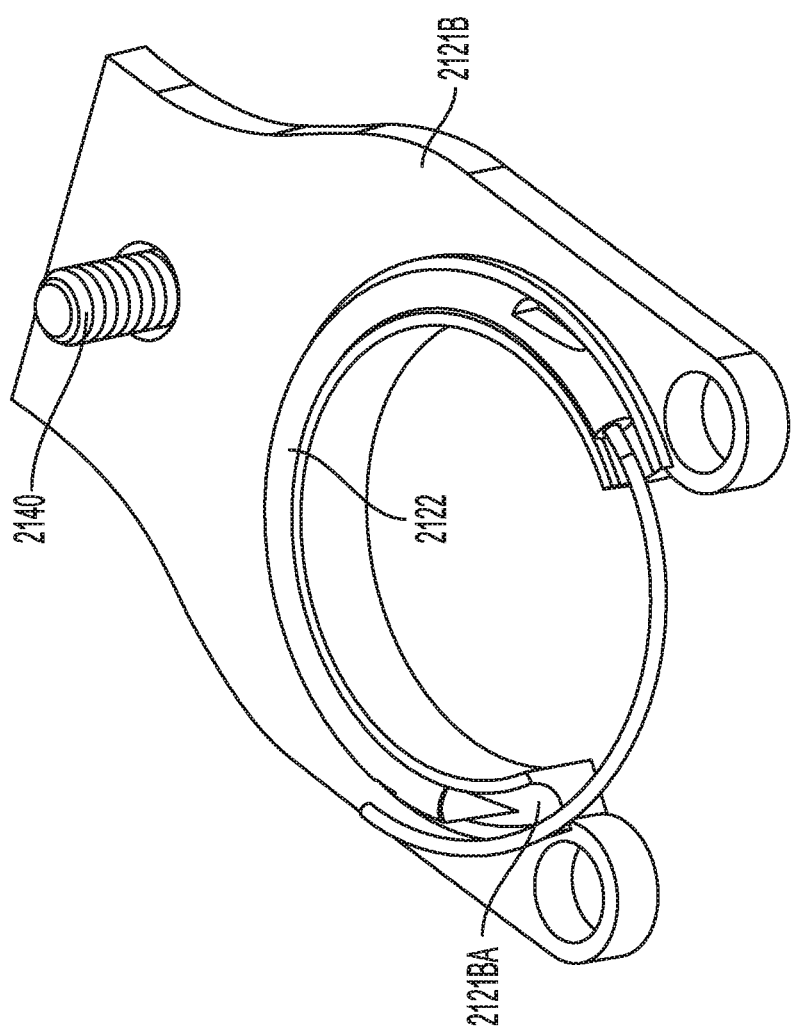
FIG. 28 is a top perspective view illustration of an exemplary removable first housing bottom, per an embodiment herein.

In some embodiments, per FIGS. 20 and 28, an angle between a needle axis 2160A and a proximal axis of the endoscope 2160B is about 5 degrees to about 85 degrees. In some embodiments, an angle between a center axis of the arcuate needle guide 2121BA and a proximal axis of the endoscope 2160B is adjustable within about 5 degrees to about 85 degrees. In some embodiments, the needle axis 2160A is defined as an axis normal to a plane of symmetry of the arcuate needle 123 and coincident with a centerpoint of the radius of the arcuate needle 123. In some embodiments, the proximal axis of the endoscope 2160B is defined as the center axis of a distal portion of the endoscope 2150. In some embodiments, the proximal axis of the endoscope 2160B is defined as the center axis of the endoscope fastener 2140 of the first housing 2121A. In some embodiments, the angle between a center axis of the arcuate needle guide 2160A and a proximal axis of the endoscope 2160B is defined as a maximum, a minimum, or an average angle.

Figure 25:
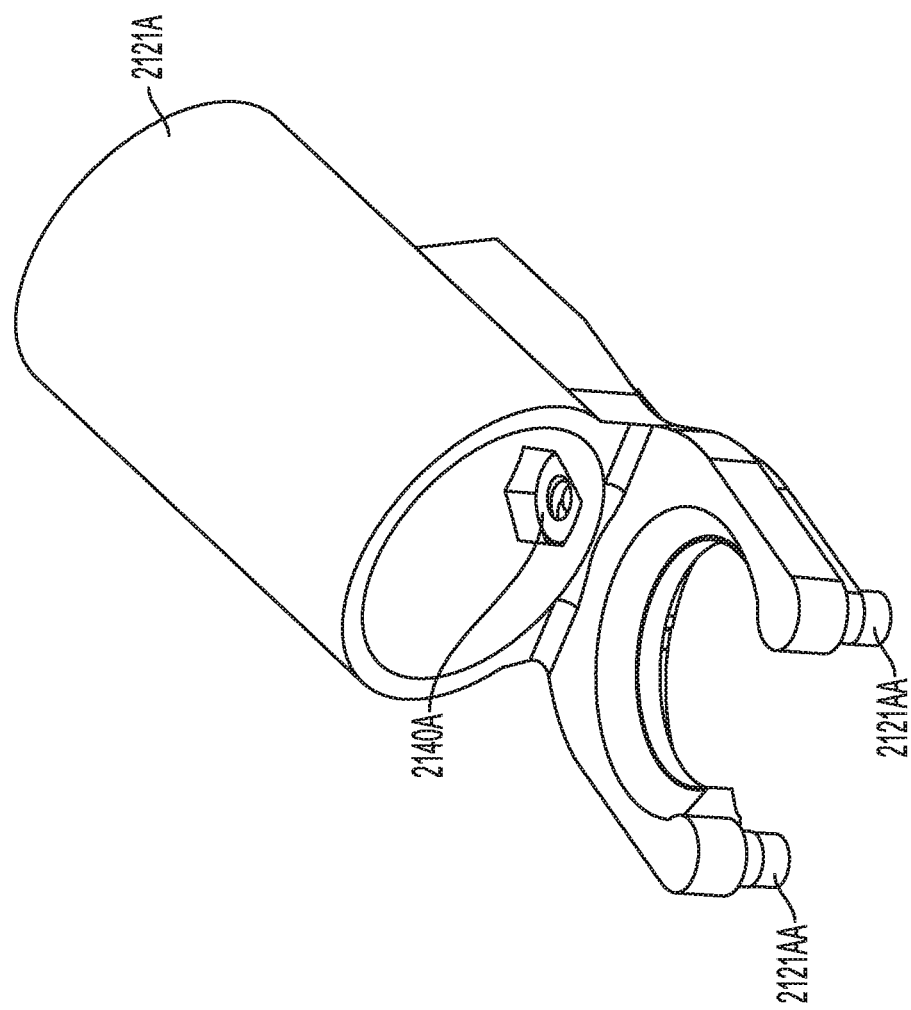
FIG. 25 is an illustration of an exemplary first housing of the second proximal assembly, per an embodiment herein.
Figure 26:
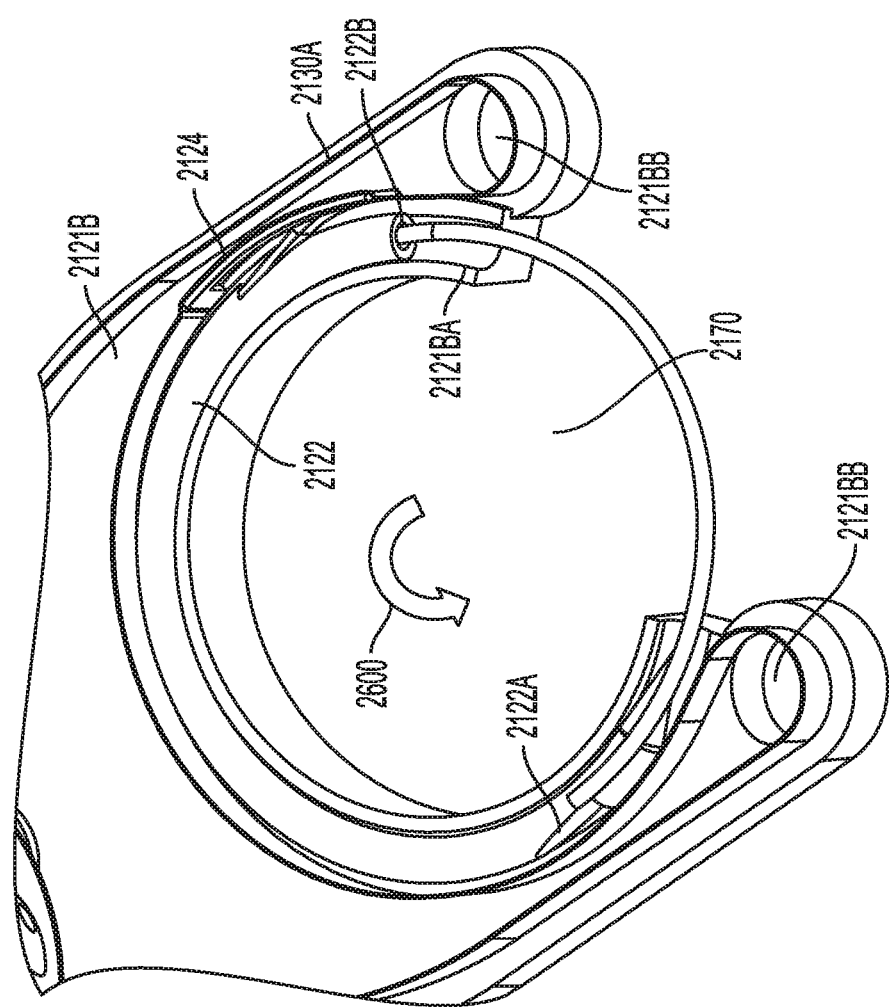
FIG. 26 is a cross-sectioned illustration of the exemplary second proximal assembly, per an embodiment herein.

As shown, in some embodiments, per FIGS. 25 and 26, the primary housing portion 2121A comprises a pulley 2121AA and the secondary housing portion 2121B comprises a pulley hole 2121BB. Alternatively, the secondary housing portion 2121B comprises the pulley 2121AA and the primary housing portion 2121A comprises the pulley hole 2121BB. As shown, the primary housing portion 2121A comprises two pulleys 2121AA. Alternatively, in some embodiments, at least one of the primary housing portion 2121A or the secondary housing portion 2121B comprises more than two pulleys 2121AA. In some embodiments, the pulley 2121AA supports and directs the cable 2130 as it travels through the first housing 2121. In some embodiments, at least a portion of the pulley 2121AA fits within the pulley hole 2121BB. In some embodiments, at least a portion of the pulley 2121AA press fits within the pulley hole 2121BB. In some embodiments, at least a portion of the pulley 2121AA fits within the pulley hole 2121BB to align the primary housing portion 2121A with respect to the secondary housing portion 2121B. As shown, the pulley 2121AA and the pulley hole 2121BB have a cross sectional shape comprising a circle. Alternatively, in some embodiments, at least one of the pulley 2121AA or the pulley hole 2121BB have a cross sectional shape comprising a triangle, a square, a pentagon, a hexagon, or any other polygon. In some embodiments, the pulley 2121AA rotates with respect to at least one of the primary housing portion 2121A or the secondary housing portion 2121B. In some embodiments, the pulley 2121AA is fixed with respect to at least one of the primary housing portion 2121A or the secondary housing portion 2121B. In some embodiments, the pulley 2121AA comprises a bearing, a rod, a curved surface, or any combination thereof.

As shown, the first housing 2121 comprises a distal sheath fastener that couples the sheath to the first housing 2121. In some embodiments, at least one of the primary housing portion 2121A or the secondary housing portion 2121B further comprises a distal sheath fastener that couples a portion of the sheath to the first housing 2121. In some embodiments, the distal sheath fastener fixes a portion of the sheath with respect to the first housing 2121, such that the cable 130 is allowed to travel within the sheath upon rotation of the wheel. As shown, the exemplary distal sheath fastener comprises a clamp. In some embodiments, the distal sheath fastener comprises a plate and one or more sheath fastener screws that compress the cable sheath between the plate and the first housing 2121. Alternatively in some embodiments, the distal sheath fastener comprises a screw, a tie, a tape, or any combination thereof. In some embodiments, the first housing 2121 comprises at least one distal sheath fastener for the first cable portion, and at least one distal sheath fastener for the second cable portion. In some embodiments, the first housing 2121 comprises a single distal sheath fastener for both the first cable portion and the second cable portion. In some embodiments, a portion of the cable sheath extends past the termination of the distal sheath fastener and into the first housing 2121. In some embodiments, the first housing 2121 comprises 1, 2, 3, 4, 5, 6, 7, 8, 9, 10, or more distal sheath fasteners. Alternatively, in some embodiments, the distal sheath fastener comprises a clamp, a tie, a band, a hook and loop fastener, an adhesive, or any combination thereof.

In some embodiments, the first housing 2121 has an arcuate needle guide 2121BA. In some embodiments, at least one of the primary housing portion 2121A or the secondary housing portion 2121B has the arcuate needle guide 2121BA. In some embodiments, the arcuate needle 2122 slides freely within the arcuate needle guide 2121BA. In some embodiments, the arcuate needle guide 2121BA constrains the arcuate needle 2122 to rotate within one degree of freedom. In some embodiments, the arcuate needle guide 2121BA constrains the arcuate needle 2122 to rotate within at least one rotational degree of freedom. As seen, the exemplary arcuate needle guide 2121BA encloses at least a portion of the arcuate needle 122. In some embodiments, the arcuate needle guide 2121BA has an interior width greater than a thickness 1510 of the arcuate needle 2122. In some embodiments, at least one of the arcuate needle 2122 or the arcuate needle guide 2121BA has a cross sectional shape comprising a circle, a square, a rectangle, or any other polygon.

In some embodiments, a gulf 2170 is formed between a first termination of the arcuate needle guide 2121BA and a second opposing termination of the arcuate needle guide 2121BA within the second proximal assembly 2120. In some embodiments, a gulf 2170 is formed between a first pulley hole 2121BB and a second opposing pulley hole 2121BB within the first distal assembly second proximal assembly 2120. In some embodiments, the gulf 2170 accepts a tissue for suturing by the arcuate needle 2122. In some embodiments, the tissue is supported against the arcuate needle 2122 throughout the suturing process. In some embodiments, the second proximal assembly 2120 does not comprise an anchor exchange catheter.

Per FIG. 26 in some embodiments, the arcuate needle 2122 has a notch 2122A. In some embodiments, the arcuate needle 2122 has 2, 3, 4, 5, 6, 7, 8, 9, 10 or more notches 2122A. In some embodiments, the notch 2122A and the pawl 2124 engage when the cable 2130 translates in a first rotational direction 2600 about the first housing portion 2121A, the second housing portion 2121B, or both. In some embodiments, the notch 2122A and the pawl 2124 disengage when the cable 2130 translates opposite the first rotational direction 2600. In some embodiments, the notch 2130 is ramped in a direction opposite the first rotational direction 2600. In some embodiments, the ramped notch 2130 ensures that the second pawl portion 2124B properly seats within the notch 2130. In some embodiments, the notch 2130 is ramped at an angle of about 5, 10, 15, 20, 25, 30, 35, 40, 45, 50, 55, 60, 65 or more degrees, including increments therein. As shown, in some embodiments, the arcuate needle 2122 has two notches 2122A, wherein each notch 2122A is spaced about the arcuate needle 2122 at an angle of about 180 degrees.

In some embodiments, an outer diameter of the arcuate needle 2122 is about 7 mm to about 20 mm. In some embodiments, an outer diameter of the arcuate needle 2122 is at least about 7 mm. In some embodiments, an outer diameter of the arcuate needle 2122 is at most about 20 mm. In some embodiments, a thickness 1510 of the arcuate needle 2122 is about 0.5 mm to about 2 mm. In some embodiments, a thickness 1510 of the arcuate needle 2122 is at least about 0.5 mm. In some embodiments, a thickness 1510 of the arcuate needle 2122 is at most about 2 mm. In some embodiments, a ratio between an outer diameter and a thickness 1510 of the arcuate needle 2122 is about 3:1 to about 15:1. In some embodiments, a ratio between an outer diameter and the thickness 1510 of the arcuate needle 2122 is about 3:1, 4:1, 5:1, 6:1, 7:1, 8:1, 9:1, 10:1, 11:1, 12:1, 13:1, 14:1, or 15:1, including increments therein. In some embodiments, a ratio between an outer diameter and the thickness 1510 of the arcuate needle 2122 is at least about 3:1. In some embodiments, the outer diameter of the arcuate needle 2122 is measured as a maximum distance between two points on the surface of the arcuate needle 2122. In some embodiments, the outer diameter of the arcuate needle 2122 is measured as a maximum outer diameter of the arcuate needle 2122. In some embodiments, the width of the arcuate needle 2122 is measured as a thickness 1510 of the arcuate needle 2122. In some embodiments, the width of the arcuate needle 2122 is measured as a thickness 1510 of the arcuate needle 2122 that is not within the pointed end, the suture end, or the notch 2122A. In some embodiments, the width of the arcuate needle 2122 is measured as a maximum, a minimum or an average thickness 1510 of the arcuate needle 2122.

In some embodiments, the notches 2122A are spaced about the arcuate needle 2122 at an angle of about 10 degrees to about 180 degrees. In some embodiments, the notches 2122A are spaced about the arcuate needle 2122 at an angle of about 10 degrees to about 20 degrees, about 10 degrees to about 30 degrees, about 10 degrees to about 40 degrees, about 10 degrees to about 50 degrees, about 10 degrees to about 60 degrees, about 10 degrees to about 80 degrees, about 10 degrees to about 100 degrees, about 10 degrees to about 120 degrees, about 10 degrees to about 140 degrees, about 10 degrees to about 160 degrees, about 10 degrees to about 180 degrees, about 20 degrees to about 30 degrees, about 20 degrees to about 40 degrees, about 20 degrees to about 50 degrees, about 20 degrees to about 60 degrees, about 20 degrees to about 80 degrees, about 20 degrees to about 100 degrees, about 20 degrees to about 120 degrees, about 20 degrees to about 140 degrees, about 20 degrees to about 160 degrees, about 20 degrees to about 180 degrees, about 30 degrees to about 40 degrees, about 30 degrees to about 50 degrees, about 30 degrees to about 60 degrees, about 30 degrees to about 80 degrees, about 30 degrees to about 100 degrees, about 30 degrees to about 120 degrees, about 30 degrees to about 140 degrees, about 30 degrees to about 160 degrees, about 30 degrees to about 180 degrees, about 40 degrees to about 50 degrees, about 40 degrees to about 60 degrees, about 40 degrees to about 80 degrees, about 40 degrees to about 100 degrees, about 40 degrees to about 120 degrees, about 40 degrees to about 140 degrees, about 40 degrees to about 160 degrees, about 40 degrees to about 180 degrees, about 50 degrees to about 60 degrees, about 50 degrees to about 80 degrees, about 50 degrees to about 100 degrees, about 50 degrees to about 120 degrees, about 50 degrees to about 140 degrees, about 50 degrees to about 160 degrees, about 50 degrees to about 180 degrees, about 60 degrees to about 80 degrees, about 60 degrees to about 100 degrees, about 60 degrees to about 120 degrees, about 60 degrees to about 140 degrees, about 60 degrees to about 160 degrees, about 60 degrees to about 180 degrees, about 80 degrees to about 100 degrees, about 80 degrees to about 120 degrees, about 80 degrees to about 140 degrees, about 80 degrees to about 160 degrees, about 80 degrees to about 180 degrees, about 100 degrees to about 120 degrees, about 100 degrees to about 140 degrees, about 100 degrees to about 160 degrees, about 100 degrees to about 180 degrees, about 120 degrees to about 140 degrees, about 120 degrees to about 160 degrees, about 120 degrees to about 180 degrees, about 140 degrees to about 160 degrees, about 140 degrees to about 180 degrees, or about 160 degrees to about 180 degrees. In some embodiments, the notches 2122A are spaced about the arcuate needle 2122 at an angle of about 10 degrees, about 20 degrees, about 30 degrees, about 40 degrees, about 50 degrees, about 60 degrees, about 80 degrees, about 100 degrees, about 120 degrees, about 140 degrees, about 160 degrees, or about 180 degrees. In some embodiments, the notches 2122A are spaced about the arcuate needle 2122 at an angle of at least about 10 degrees, about 20 degrees, about 30 degrees, about 40 degrees, about 50 degrees, about 60 degrees, about 80 degrees, about 100 degrees, about 120 degrees, about 140 degrees, or about 160 degrees. In some embodiments, the notches 2122A are spaced about the arcuate needle 2122 at an angle of at most about 20 degrees, about 30 degrees, about 40 degrees, about 50 degrees, about 60 degrees, about 80 degrees, about 100 degrees, about 120 degrees, about 140 degrees, about 160 degrees, or about 180 degrees.

Figure 23:
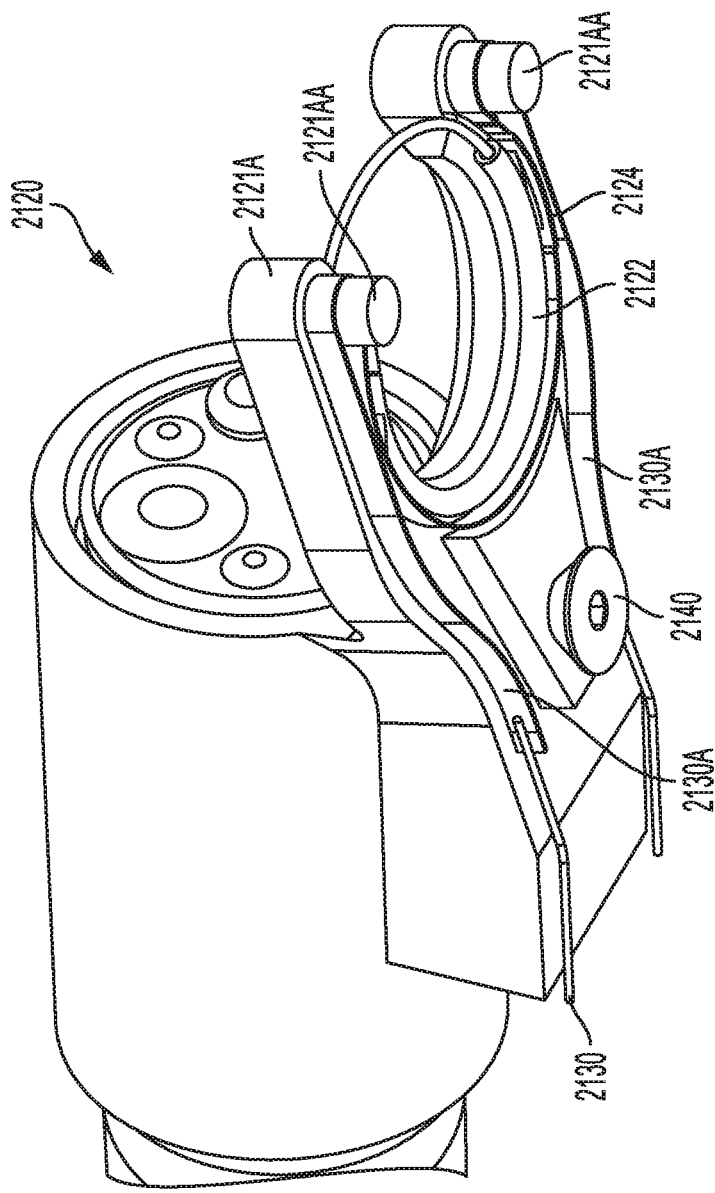
FIG. 23 is a first bottom perspective illustration of the exemplary second proximal assembly without a bottom plate, per an embodiment herein.
Figure 24:
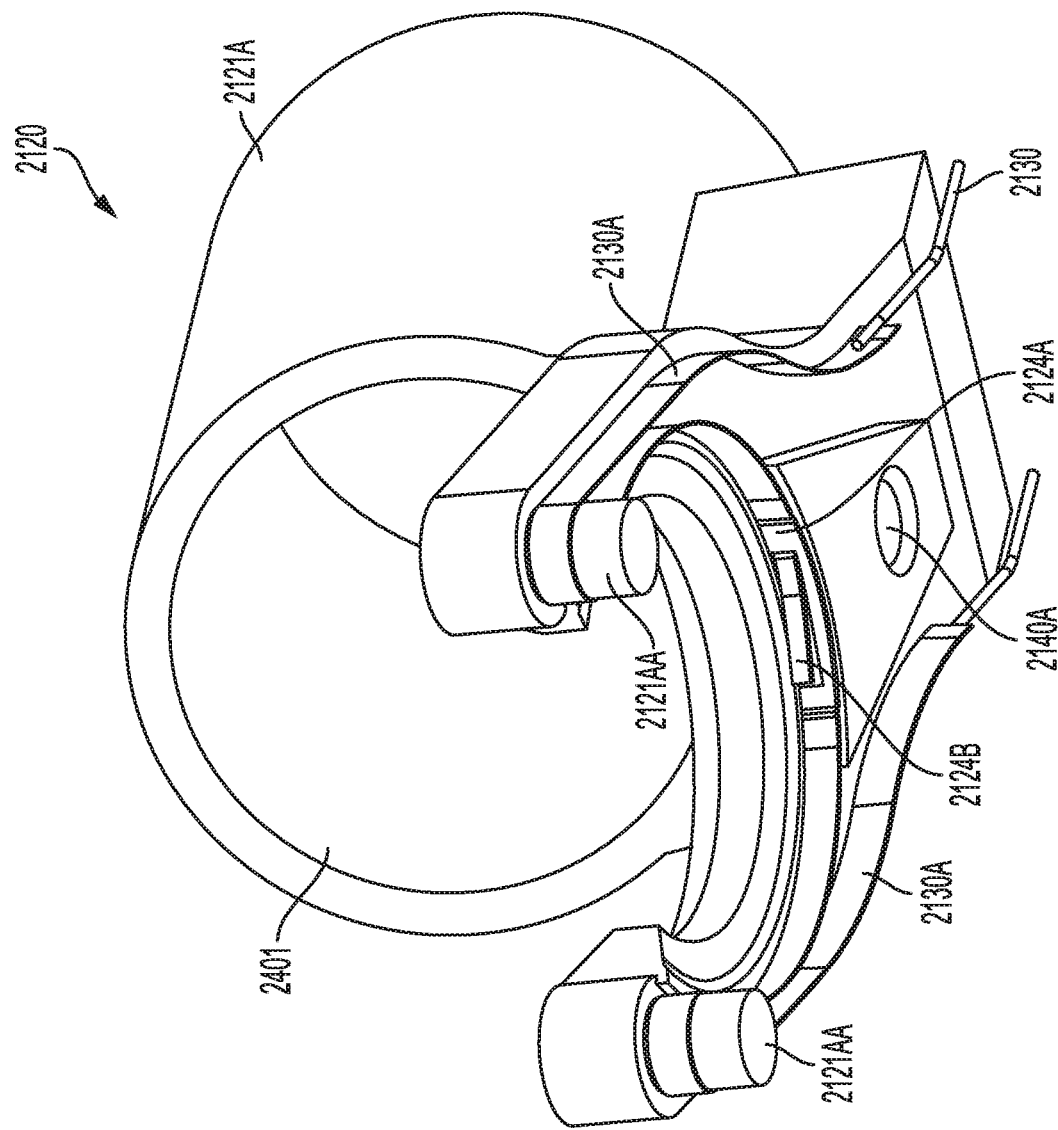
FIG. 24 is a second bottom perspective illustration of the exemplary second proximal assembly without a bottom plate, per an embodiment herein.

As shown in FIGS. 23-25 (without the second housing portion 2121B) the cable 2130 having a pawl 2124 enters the first housing 2121, wrap around a first pulley 2121AA, around the arcuate needle 2122, around a second pulley 2121AA, and passes out the first housing 2121. As shown, the cable 2130 comprises a flattened portion 2130A. In some embodiments, the flattened portion 2130A increases stability of the cable 2130 as it wraps around the pulley 2121AA. Further, in some embodiments, the pawl 2124 is located on the flattened portion of the cable 2130A. In some embodiments, the flattened portion of the cable 2130A is manufactured by mechanically flattening a portion of the cable 2130A, or by adhering a flattened material to the cable 2130. In some embodiments, the pawl 2124 is attached to the cable 2130. In some embodiments, the pawl 2124 is coupled to the flattened portion of the cable 2130A.

As shown per FIG. 24, the pawl 2124 comprises a first pawl portion 2124A and a second pawl portion 2124B, wherein the first pawl portion 2124A is attached to the cable 2130 or the flattened a portion of the cable 2130A, and wherein the second pawl portion 2124B is not coupled to the cable 2130 and the flattened a portion of the cable 2130A. In some embodiments, the pawl 2124 comprises a flexure. In some embodiments, the second pawl portion 2124B is bent inwards towards the arcuate needle 2122, at rest, and flexes about an intersection between the second pawl portion 2124B and the first pawl portion 2124A. In some embodiments, the second pawl portion 2124B bends outward and away from the arcuate needle 2122 about an intersection between the second pawl portion 2124B and the first pawl portion 2124A when the arcuate needle 2122 contacts the second pawl portion 2124B. As shown in FIG. 26, a terminal end of the second pawl portion 2124B contacts and presses against the notch 2122A of the arcuate needle 2122 to translate the arcuate needle 2122 in the first direction 2600. Additionally or alternatively, the terminal end of the second pawl portion 2124B contacts and presses against the suture end 2122B of the arcuate needle 2122 to translate the arcuate needle 2122 in the first direction 2600. Alternatively, in some embodiments, the pawl 2124 comprises a spring, a dual spring gate, a cushion, a piston, a rod, a pin, a tooth, or any combination thereof. In some embodiments, the pawl 2124 is engagement biased.

FIGS. 27A-F show the exemplary second proximal assembly in a first, second, third, fourth, fifth, and sixth position, respectively. Per FIG. 27A, suturing with the second proximal assembly comprises translating the cable 2130 such that the pawl 2124 travels to a terminal position of a second rotational direction opposite the first rotational direction 2600 within the secondary housing portion 2121B (the position of the pawl 2124 shown in FIG. 27A) while the arcuate needle 2122 is fully enclosed within the secondary housing portion 2121B. When the pawl 2124 and arcuate needle 2122 are in this position, the pawl 2124 automatically engages with a first notch within the arcuate needle 2122, as shown. Thereafter, per FIGS. 27B-C the cable 2130 is translated such that the engaged arcuate needle 2122 and pawl 2124 travel in the first rotational direction 2600 to the terminal position of the pawl 2124 in the first rotational direction 2600 within the secondary housing portion 2121B. The translation of the cable 2300 and pawl 2124 thereby moves a portion of the arcuate needle 2122 out of the secondary housing portion 2121B to perform a first suture. Per FIG. 27D, the cable 2130 is then be translated back to its terminal position in the second rotational direction within the secondary housing portion 2121B to automatically engage a second notch within the arcuate needle 2122. As seen in FIGS. 27E-F, translation of the cable 2130 and the pawl 2124 in the first direction 2600 thereafter, returns the arcuate needle 2122 to its original position within the secondary housing portion 2121B, whereas further translation of the cable 2130 and the pawl 2124 in the second direction returns the pawl to its terminal position of a second rotational direction within the secondary housing portion 2121B per FIG. 27A. Therefore, translation of the cable 2130 in the first direction 2600, a second direction opposite the first direction 2600, the first direction 2600, and then the second direction completes a single suture, whereas repeating this process enables repetitive suturing.

Figure 29:
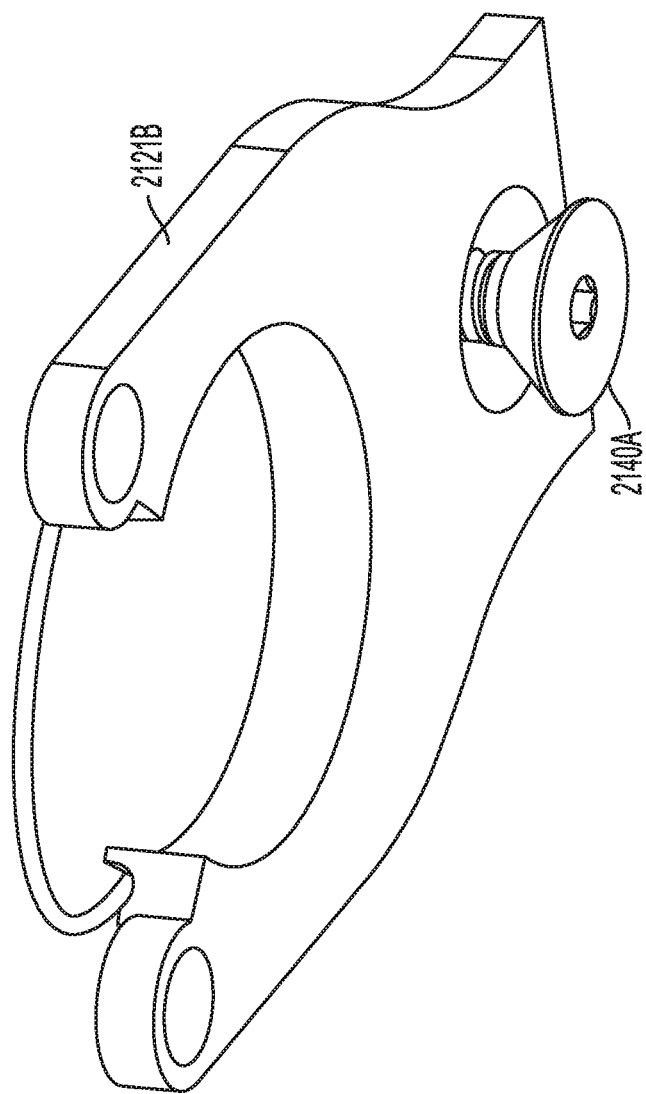
FIG. 29 is a bottom perspective view illustration of an exemplary removable first housing bottom, per an embodiment herein.

FIG. 29 shows the arcuate needle 2122 within the arcuate needle guide 2121BA of the secondary housing portion 2121B. As shown per FIG. 28, the arcuate needle guide 2121BA surrounds a portion of the arcuate needle 2122. As seen therein, the arcuate needle guide 2121BA surrounds about 280 degrees of the cross sectional circumference of the arcuate needle 2122. Alternatively, in some embodiments, the arcuate needle guide 2121BA surrounds about 100, 120, 140, 160, 180, 200, 220, 240, 260, 280, 300, 320 degrees or more of the cross sectional circumference of the arcuate needle 2122, including increments therein.

Figure 30A:
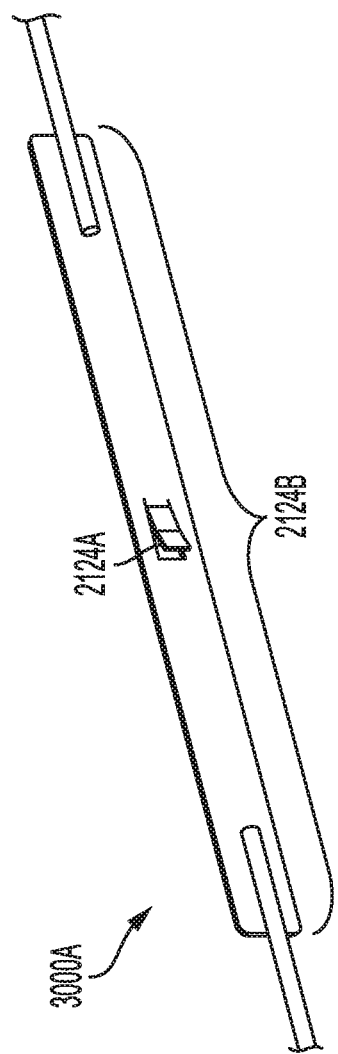
FIG. 30A is an illustration of an exemplary first cable and pawl combination, per an embodiment herein.
Figure 30B:
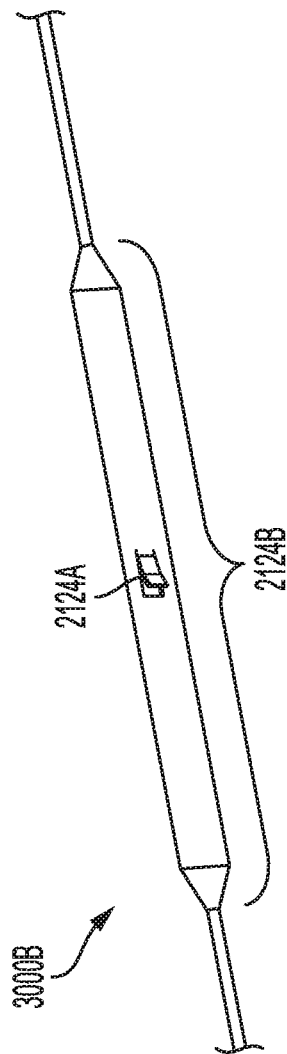
FIG. 30B is an illustration of an exemplary second cable and pawl combination, per an embodiment herein.
Figure 30C:
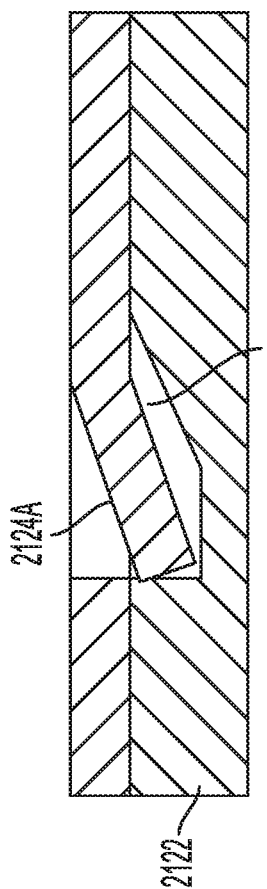
FIG. 30C is an illustration of an exemplary engaged cable and pawl combination, per an embodiment herein.

In some embodiments, per FIGS. 30A-C the cable and the pawl comprise a single cable pawl 3000A 3000B comprising a flattened portion 2124B having a tab 2124A. As shown, the tab 2124A comprises a flexure. Alternatively, in some embodiments, the 2124A comprises an indent, a spring, or any combination thereof. In some embodiments, the tab 2124A engages and disengages with the notch of the arcuate needle in the same way as the pawl. As shown, in some embodiments, the tab 2124A has an expanded position where the tab 2124A is at rest and projects at an angle from the flattened portion 2124B. In some embodiments, the tab 2124A projects at an angle from the flattened portion 2124B of about 5, 10, 15, 20, 25, 30, 35, 40, 45, 50, 55, 60 or more degrees including increments therein. As shown in FIG. 30C, in some embodiments the tab 2124A engages with the notch 2122A of the arcuate needle 2122 when in the expanded position. In some embodiments, a distal tip of the tab 2124A presses against the notch 2122A of the arcuate needle 2122 when engaged. In some embodiments, the tab 2124A has a collapsed position, where the tab 2124A and the flattened portion 2124B are generally coplanar. In some embodiments, in the collapsed position, the tab 2124A is compressed against the flattened portion 2124B by the arcuate needle 2122. In some embodiments, the tab 2124A disengages with the notch 2122A of the arcuate needle 2122 when in the collapsed position. In some embodiments, the tab 2124A is configured to be repeatedly compressed and released to disengage and engage with a notch of the arcuate needle, repeatedly. In some embodiments, per FIG. 30A the cable pawl 3000A is formed within a sheet of material that is adhered to the cable 2130A. Alternatively, in some embodiments, per FIG. 30B, the cable pawl 3000A is formed from a single continuous piece of material.

In some embodiments, at least one of the primary housing portion 2121A, the pulley 2121AA, the secondary housing portion 2121B, the cable 2130, the pawl 2124, the tab 2124A, or the single cable pawl 3000A, 300B is composed of metal, plastic, wood, carbon fiber, ceramic, or any combination thereof.

Tilting First Housing

FIGS. 31A-36 show illustrations of an exemplary tilting first housing 3120 comprising a primary tilting housing 3121A, a secondary tilting housing 3121B, and a tertiary tilting housing 3121C. In some embodiments, the tilting first housing 3120 further comprises a fourth or more tilt housings. As shown the secondary tilting housing 3121B and the tertiary tilting housing 3121C are rigidly attached to each other, wherein the secondary tilting housing 3121B and the tertiary tilting housing 3121C rotate with respect to the primary tilt housing 3121A about a tilt axis 3151. In some embodiments, the secondary tilting housing 3121B, and the tertiary tilting housing 3121C are a single component. In some embodiments, the tilt axis 3151 is perpendicular to a proximal endoscope axis 3152. In some embodiments, the tilt axis 3151 does not intersect the proximal endoscope axis 3152. In some embodiments, the secondary tilting housing 3121B and the tertiary tilting housing 3121C are rigidly attached to each other by a fastener. In some embodiments, the fastener comprises a press fit fastener, a screw, a nut, a bolt, a hook and loop fastener, an adhesive, a weld, or any combination thereof.

Figure 31A:
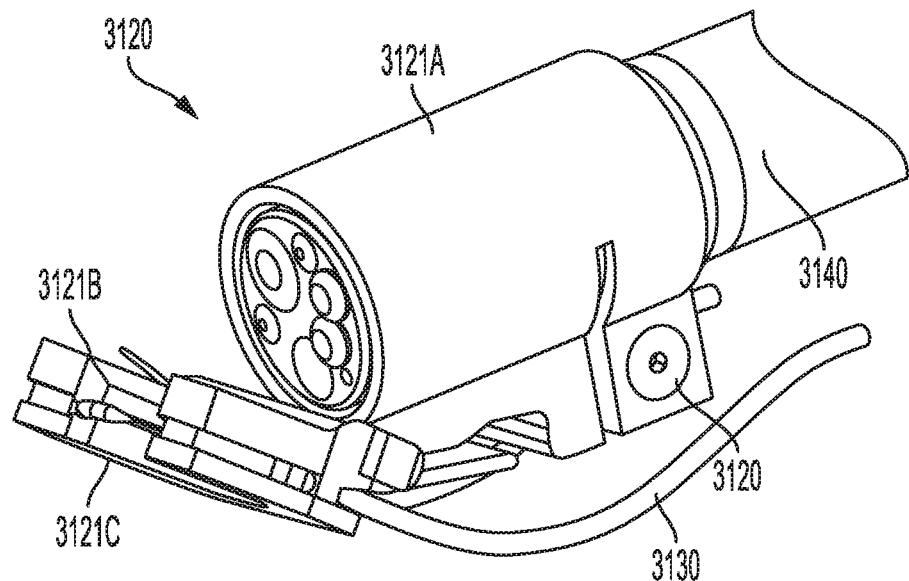
FIG. 31A is an illustration of an exemplary third distal assembly in a first position, per an embodiment herein.
Figure 31B:
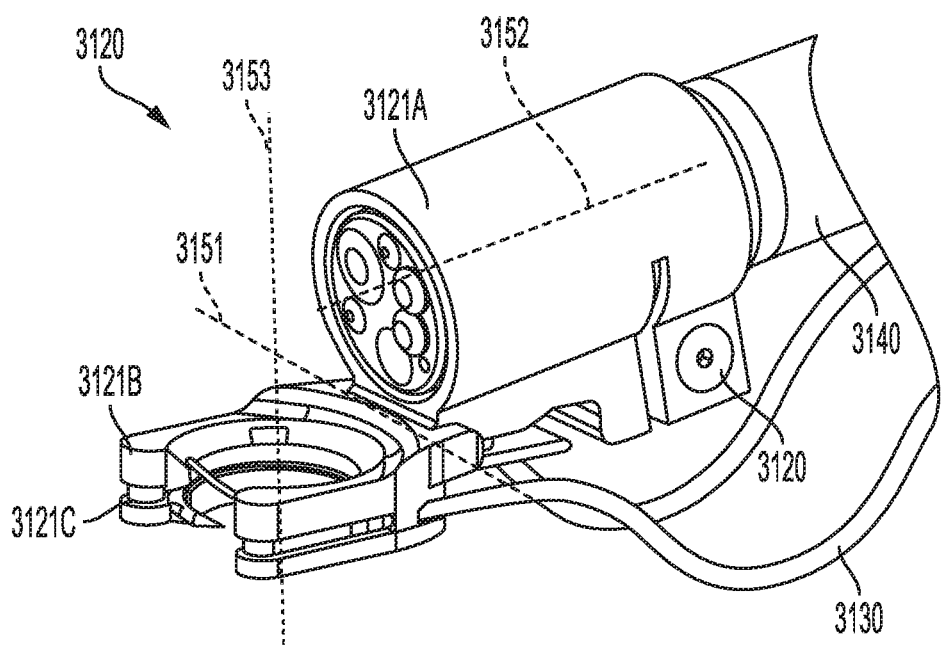
FIG. 31B is an illustration of the exemplary third distal assembly in a second position, per an embodiment herein.
Figure 32:
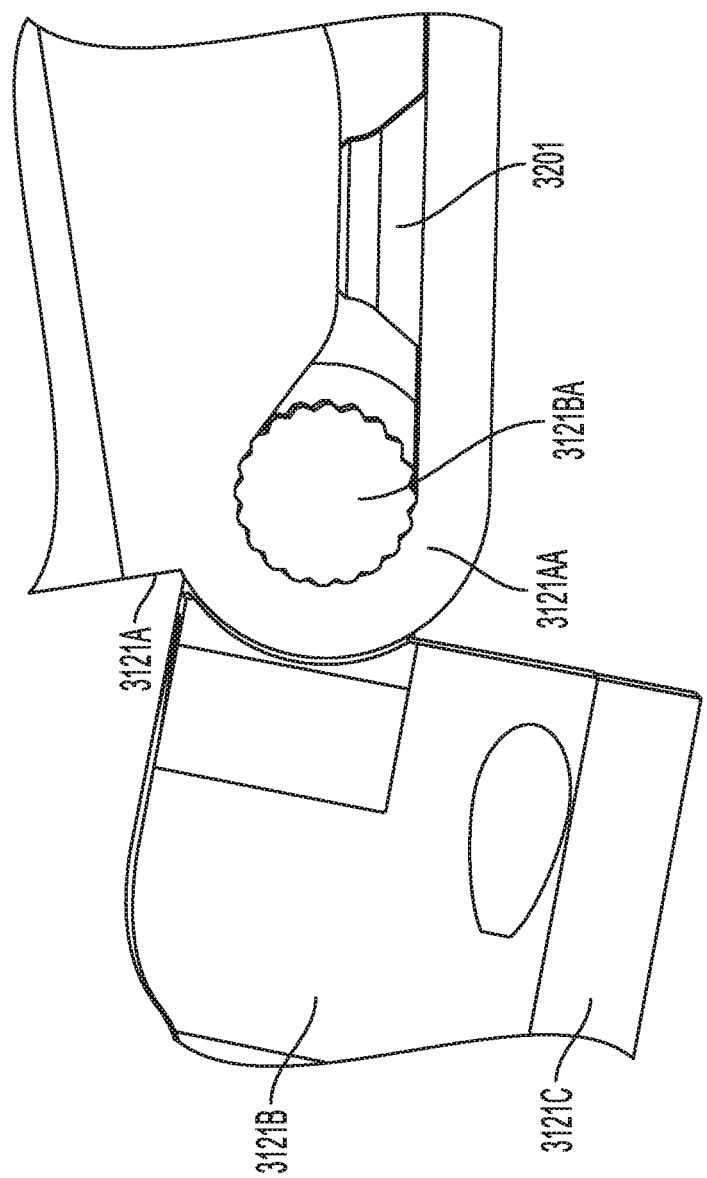
FIG. 32 is another illustration of the exemplary third distal assembly in a second position, per an embodiment herein.
Figure 33:
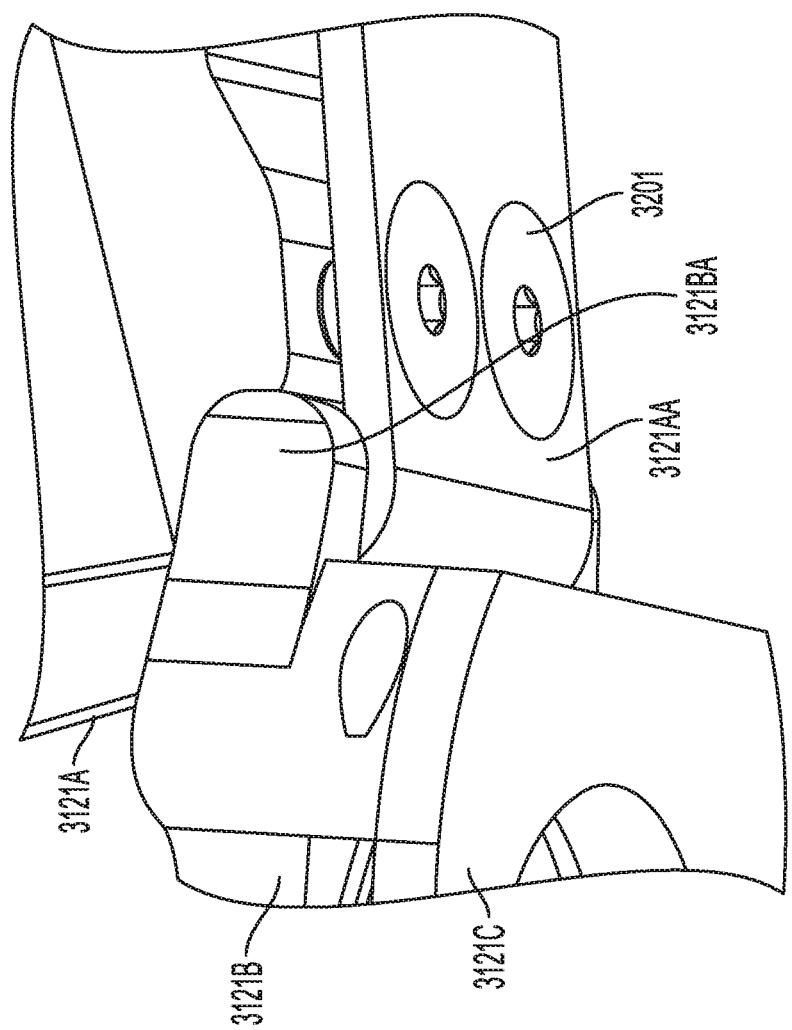
FIG. 33 is another illustration of the exemplary third distal assembly in a second position, per an embodiment herein.
Figure 34:
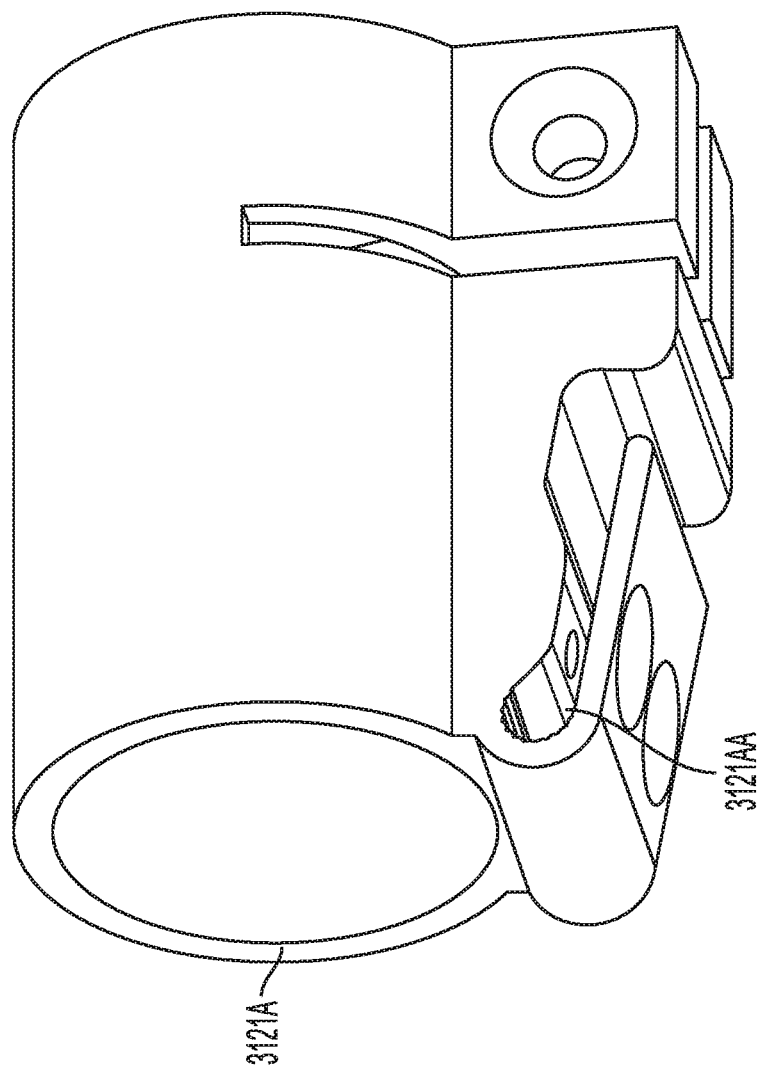
FIG. 34 is an illustration of an exemplary first portion of the first housing of the exemplary third distal assembly in a second position, per an embodiment herein.

As shown in FIGS. 31A-B, the primary tilting housing 3121A comprises an endoscope fastener 3120 that couples the primary tilting housing 3121A to the endoscope 3140. In some embodiments, the endoscope fastener 3120 removably couples the primary tilting housing 3121A to the endoscope 3140. As shown, the endoscope fastener 3120 comprises a screw, wherein the primary tilting housing 3121A comprises a threaded feature or threaded insert that accepts the screw, such that the endoscope fastener 3120 and the threaded feature or threaded insert within the primary tilting housing 3121A clamp around a distal end of the endoscope 3140 to secure the primary tilting housing 3121A to the endoscope 3140. As shown, the primary tilting housing 3121A comprises a slot configured to separate the endoscope fastener 3120 from the remainder of the tilting housing 3121A such that the tilting housing 3121A can deform when the screw is tightened. Alternatively, in some embodiments, the primary tilting housing 3121A does not comprise the slot.

As shown, in some embodiments, the endoscope fastener 3120 is rounded. In some embodiments, the endoscope 3140 has a proximal outer diameter of about 5 mm to about 16 mm. As such, in some embodiments, the endoscope fastener 3120 has an inner diameter of about 5 mm to about 16 mm. In some embodiments, the endoscope fastener 3120 has an inner diameter of at least about 5 mm. In some embodiments, the endoscope fastener 3120 has an inner diameter of at most about 16 mm. In some embodiments, the press fit endoscope fastener 3120. In some embodiments, the press fit endoscope fastener 3120 has a diameter equal to or lesser than the diameter of the endoscope 3140. In some embodiments, the endoscope fastener 3120 has a diameter equal to or greater than the diameter of the endoscope 3140. In some embodiments, the endoscope fastener 3120 is tapered and has a first inner diameter and a second inner diameter, wherein the first inner diameter is distal to the second inner diameter. In some embodiments, the first inner diameter is greater than the second inner diameter. In some embodiments, the second inner diameter is greater than the first inner diameter. In some embodiments, the diameter of the endoscope fastener 3120 is measured as a maximum, a minimum, or an average interior width. In some embodiments, the diameter of the endoscope 3140 is measured as a maximum, a minimum, or an average exterior width. Alternatively, in some embodiments, the endoscope fastener 3120 has a cross sectional shape comprising a triangle, a square, a hexagon, or any other polygon.

Alternatively, in some embodiments, the endoscope fastener 3120 comprises a press fit fastener. In some embodiments, the press fit endoscope fastener 3120 attaches to the endoscope 3140 by firmly pressing the press fit endoscope fastener 3120 onto a distal end of the endoscope 3140. In some embodiments, the press fit endoscope fastener 3120 attaches to the endoscope 3140 by firmly pressing and rotating the press fit endoscope fastener 3120 onto a distal end of the endoscope 3140. In some embodiments, the press fit endoscope fastener 3120 detaches from the endoscope 3140 by firmly pulling the press fit endoscope fastener 3120 off the distal end of the endoscope 3140. Alternatively, in some embodiments, the endoscope fastener 3120 comprises a clamp, an adhesive, a tape, a strap, a set screw, a hook and loop fastener, a magnet, or any combination thereof. In some embodiments, the first distal assembly 120 comprises 1, 2, 3, 4, 5, 6, 7, 8, 9, 10, or more endoscope fasteners 3120.

Further, as shown, at least one of the secondary tilting housing 3121B or the tertiary tilting housing 3121C secure the cable sheath of the cable 3130. In some embodiments, at least one of the secondary tilting housing 3121B or the tertiary tilting housing 3121C comprise a hole that accepts the cable sheath of the cable 3130. In some embodiments, the cable sheath of the cable 3130 is clamped between the secondary tilting housing 3121B and the tertiary tilting housing 3121C. Alternatively, in some embodiments, the cable sheath of the cable 3130 is coupled to at least one of the secondary tilting housing 3121B or the tertiary tilting housing 3121C by an adhesive, a clamp, a tie, a hook and loop fastener, or any combination thereof.

Per FIGS. 32-36, the exemplary primary tilting housing 3121A comprises a primary tilt mechanism 3121AA and the exemplary secondary tilting housing 3121B comprises a secondary tilt mechanism 3121BA, wherein the primary tilt mechanism 3121AA and the secondary tilt mechanism 3121BA couple the primary tilting housing 3121A and the secondary tilting housing 3121B. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A about the tilt axis 3151. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A about 300 degrees about the tilt axis 3151. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A such that an angle between an arcuate needle axis 3153 and the proximal endoscope axis 3152 increases from about 0 degrees (where arcuate needle axis 3153 and the proximal endoscope axis 3152 are parallel) to about 300 degrees. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A such that an angle between an arcuate needle axis 3153 and the proximal endoscope axis 3152 increases continuously from about 0 degrees to about 300 degrees. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A such that an angle between an arcuate needle axis 3153 and the proximal endoscope axis 3152 increases in discrete increments from about 0 degrees to about 300 degrees. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A such that an angle between an arcuate needle axis 3153 and the proximal endoscope axis 3152 increases in discrete increments of about 1, 2, 5, 10, 15, 20, 25, 30, 35, 40, 45, 50, 55, 60 or more degrees. In some embodiments, the primary tilt mechanism 3121AA and the secondary tilt mechanism 3121BA enable at least one of the secondary tilting housing 3121B or the tertiary tilting housing 3121C to rotate with respect to the primary tilting housing 3121A such that an angle between an arcuate needle axis 3153 and the proximal endoscope axis 3152 increases in discrete increments of at least about 1 degree. In some embodiments, the arcuate needle axis 3153 and the proximal endoscope axis 3152 are coincident. In some embodiments, the arcuate needle axis 3153 and the proximal endoscope axis 3152 are not coincident.

Figure 35:
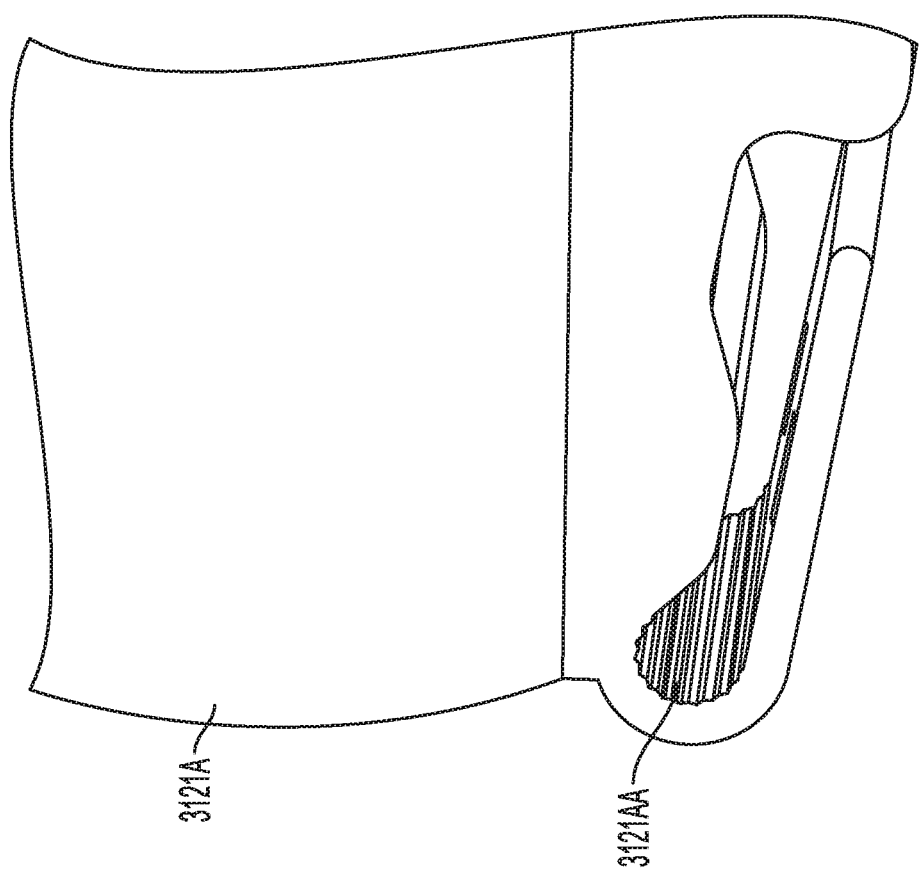
FIG. 35 is a detailed view illustration of the exemplary first portion of the first housing of the exemplary third distal assembly, per an embodiment herein.
Figure 36:
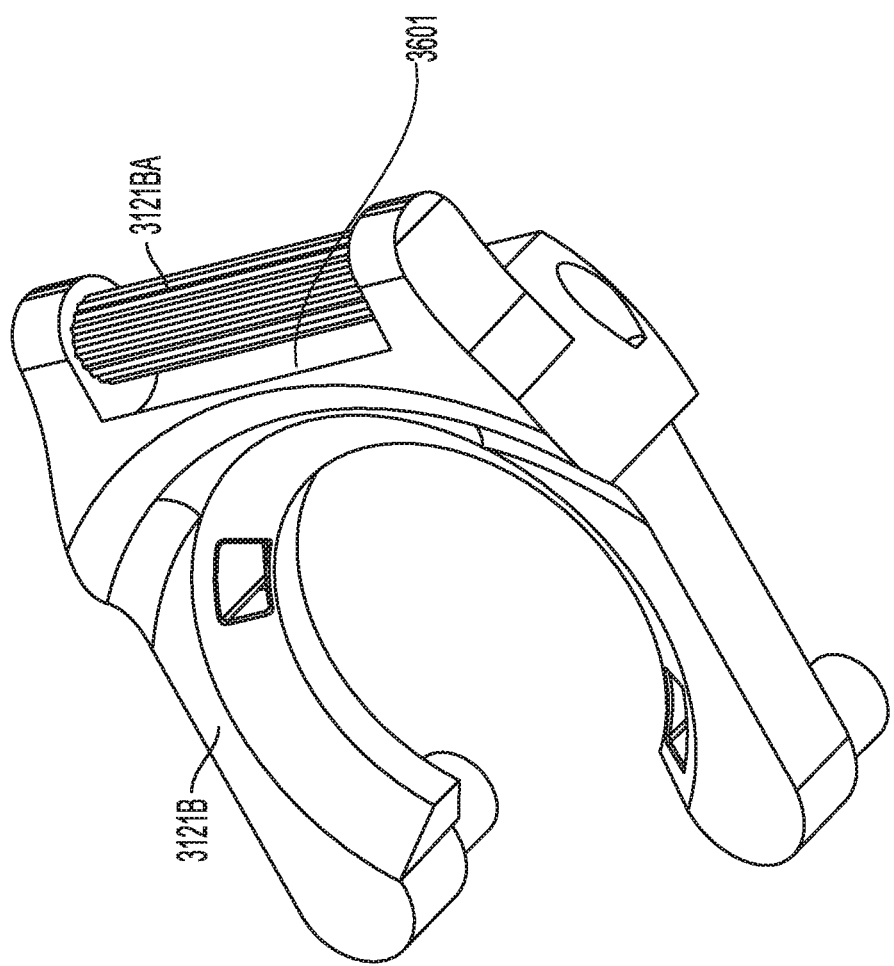
FIG. 36 is a detailed view illustration of an exemplary second portion of the first housing of the exemplary third distal assembly, per an embodiment herein.

As seen per FIGS. 35 and 36, in one example, the primary tilt mechanism 3121AA comprises a clamp having a knurled interior surface and the secondary tilt mechanism 3121BA comprises a knob having a knurled exterior surface. As shown, the secondary tilt mechanism 3121BA comprises 19 knurls and valleys, such that engagement of one knurl of the primary tilt mechanism 3121AA with one valley of the secondary tilt mechanism 3121BA defines a specific angle between the arcuate needle axis 3153 and the proximal endoscope axis 3152. As shown, the primary tilt mechanism 3121AA comprises 13 knurls and valleys, such that engagement of one knurl of the secondary tilt mechanism 3121BA with one valley of the primary tilt mechanism 3121AA defines a specific angle between the arcuate needle axis 3153 and the proximal endoscope axis 3152. Alternatively, in some embodiments, at least one of the primary tilt mechanism 3121AA or the secondary tilt mechanism 3121BA comprises 10, 11, 12, 13, 14, 15, 16, 17, 18, 20, 21, 22, 23, 24, 25 or more knurls and valleys. Alternatively, in some embodiments, the primary tilt mechanism 3121AA does not comprise the primary tilt housing 3121A. Alternatively, in some embodiments, the secondary tilt housing 3121B does not comprise the secondary tilt mechanism 3121BA.

In some embodiments, the clamp of the primary tilt mechanism 3121AA is tightened by fastening a screw 3151 to compress the clamp and prevent rotation of the secondary tilting housing 3121B with respect to the primary tilt housing 3121A about the tilt axis 3151. In some embodiments, the clamp of the primary tilt mechanism 3121AA is released by unscrewing a screw 3151 to decompress the clamp and allow rotation of the secondary tilting housing 3121B with respect to the primary tilt housing 3121A about the tilt axis 3151. In some embodiments, the clamp of the primary tilt mechanism 3121AA is tightened during surgical use. Alternatively, in some embodiments, the rotation between the primary tilting housing 3121A and the secondary tilting housing 3121B is achieved through a clamp, a pin, a screw, a knob, a tie, a band, a magnet, or any combination thereof.

As seen the secondary tilting housing 3121B comprises a gap 3601 between the secondary tilt mechanism 3121BA and the remainder of the secondary tilting housing 3121B. In some embodiments, the gap 3601 accepts a portion of the primary tilting housing 3121A as the secondary tilting housing 3121B rotates about the primary tilting housing 3121A. In some embodiments, a width of the gap 3601 is greater than a thickness of the primary tilt mechanism 3121AA.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the term "arcuate" refers to an arc of a circle or a portion of a circle.

What is claimed is:

1. A method of suturing, the method comprising
providing an endoscopic suture system, the endoscopic suture system having:
a needle configured to rotate in a first rotational direction, the needle being coupled with a suture, and
a cable configured to move in a first direction and a second direction, the cable and the needle configured to movably couple and uncouple,
such that, when the cable and the needle are coupled, movement of the cable in the first direction causes rotation of the needle in the first rotational direction;
pulling the cable in the second direction, without rotating the needle, to cause coupling of the cable with the needle;
pulling the cable in the first direction, after the needle and the cable are coupled, to rotate the needle;
pulling the cable in the second direction, without rotating the needle, to cause coupling of the cable with the needle; and
pulling the cable in the first direction, after the needle and the cable are coupled, to rotate the needle.

2. The method as defined by claim 1, wherein the cable includes a pawl.

3. The method as defined by claim 1, wherein the needle includes a notch.

4. The method as defined by claim 1, wherein the needle includes a plurality of notches.

5. The method as defined by claim 1, wherein the first rotational direction is counterclockwise and the second rotational direction is clockwise.

6. The method as defined by claim 1, wherein the endoscopic suture system is positioned with a distal housing configured to couple with the distal end of an endoscope.

7. The method as defined by claim 1, further comprising repeating the steps of
pulling the cable in the second direction, without rotating the needle, to cause coupling of the cable with the needle;
pulling the cable in the first direction, after the needle and the cable are coupled, to rotate the needle.

8. The method as defined by claim 1, wherein pulling the cable in a first direction to cause the needle to rotate in the first rotational direction comprises pulling the cable until the cable can no longer move in the first direction.

9. The method as defined by claim 1, wherein pulling the cable in the second direction until the needle and the cable are movably coupled comprises pulling the cable until the cable can no longer move in the second direction.

10. The method as defined by claim 1, wherein the cable extends to a proximal assembly coupled with an endoscope.

11. A method of suturing, the method comprising
providing an endoscopic suture system, the endoscopic suture system having:
a needle configured to rotate in a first rotational direction, the needle being coupled with a suture, and
a cable configured to move in a first direction and a second direction, the cable and the needle configured to be movably couple and uncouple,
such that, when the cable and the needle are coupled, movement of the cable in the first direction causes rotation of the needle in the first rotational direction;
pulling the cable in the first direction to rotate the needle; and
pulling the cable in the second direction to recouple the cable with the needle.

12. The method as defined by claim 11, further comprising repeating the steps of:
pulling the cable in the first direction to rotate the needle; and
pulling the cable in the second direction to recouple the cable with the needle.

13. The method as defined by claim 11, wherein the needle includes a plurality of notches.

14. The method as defined by claim 11, wherein the cable includes a pawl.

15. The method as defined by claim 11, wherein the first rotational direction is counterclockwise.

16. A method of suturing, the method comprising
providing an endoscopic suture system, the endoscopic suture system having:
a needle configured to rotate in a first rotational direction, the needle being coupled with a suture, and
a cable configured to move in a first direction and a second direction, the cable and the needle configured to be movably couple and uncouple,
such that, when the cable and the needle are coupled, movement of the cable in the first direction causes rotation of the needle in the first rotational direction;
movably coupling the needle and the cable;

pulling the cable in the first direction to cause the needle to rotate;
pulling the cable in the second direction until the needle and the cable are movably coupled; and
pulling the cable in the first direction to cause the needle to rotate.

17. The method as defined by claim 16, wherein the first rotational direction clockwise.

18. The method as defined by claim 16, wherein movably coupling the needle with the cable comprises engaging a pawl of the cable with a notch of the needle.

19. The method as defined by claim 16, further comprising providing an arcuate needle guide.

\* \* \* \* \*